United States Patent
Yee et al.

(10) Patent No.: US 11,696,933 B2
(45) Date of Patent: Jul. 11, 2023

(54) HLA-RESTRICTED VCX/Y PEPTIDES AND T CELL RECEPTORS AND USE THEREOF

(71) Applicant: Board of Regents, The University of Texas System, Austin, TX (US)

(72) Inventors: Cassian Yee, Houston, TX (US); Ke Pan, Houston, TX (US)

(73) Assignee: BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 933 days.

(21) Appl. No.: 16/474,665

(22) PCT Filed: Dec. 28, 2017

(86) PCT No.: PCT/US2017/068701
§ 371 (c)(1),
(2) Date: Jun. 28, 2019

(87) PCT Pub. No.: WO2018/126002
PCT Pub. Date: Jul. 5, 2018

(65) Prior Publication Data
US 2020/0147161 A1  May 14, 2020

Related U.S. Application Data

(60) Provisional application No. 62/595,422, filed on Dec. 6, 2017, provisional application No. 62/440,233, filed on Dec. 29, 2016.

(51) Int. Cl.
| | | |
|---|---|---|
| *C07K 14/725* | (2006.01) | |
| *A61K 36/17* | (2006.01) | |
| *A61P 35/00* | (2006.01) | |
| *A61K 9/127* | (2006.01) | |
| *C07K 14/74* | (2006.01) | |
| *C07K 16/28* | (2006.01) | |
| *C12N 15/85* | (2006.01) | |
| *A61K 45/06* | (2006.01) | |

(52) U.S. Cl.
CPC ............ *A61K 36/17* (2013.01); *A61K 9/1271* (2013.01); *A61P 35/00* (2018.01); *C07K 14/7051* (2013.01); *C07K 14/70539* (2013.01); *C07K 16/2818* (2013.01); *C12N 15/85* (2013.01); *A61K 45/06* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | |
|---|---|---|
| 7,910,109 B2 | 3/2011 | Carroll et al. |
| 2016/0024174 A1 | 1/2016 | Odunsi et al. |
| 2016/0280760 A1* | 9/2016 | Mahr ............... A61P 39/00 |

FOREIGN PATENT DOCUMENTS

| | | |
|---|---|---|
| CN | 1508142 | 6/2004 |
| CN | 110352067 | 10/2019 |
| WO | 2016/156202 A1 | 10/2016 |
| WO | 2021067687 | 4/2021 |

OTHER PUBLICATIONS

Haen et al: "The repertoire of human tumor-associated epitopes—identification and selection of antigens and their application in clinical trials", Current Opinion in Immunology, vol. 25, No. 2, Apr. 1, 2013 (Apr. 1, 2013), pp. 277-283.
Pan et al: "Identification of HLA-A0201 restricted epitope of novel cancer/testis antigens VCX/Y and generation of antigen-specific T-cell receptor engineered T cells for treatment of solid tumor malignancies", Journal of Clinical Oncology, vo 1 . 36, No. 5 supp 1 , Feb. 10, 2018 (Feb. 10, 2018), pp. 160-160.
Taguchi et al: "A Search for Novel Cancer/Testis Antigens in Lung Cancer Identifies VCX/Y Genes, Expanding the Repertoire of Potential Immunotherapeutic Targets", Cancer Research, vol. 74, No. 17, Jun. 26, 201 (Jun. 26, 2014), pp. 4694-4705.
Wälchli et al: "A Practical Approach to T-Cell Receptor Cloning and Expression", Plos One, vol. 6, No. 11, Nov. 21, 2011 (Nov. 21, 2011), p. e27930.
Yee: "Adoptive T cell therapy: Addressing challenges in cancer immunotherapy", Journal of Translational Medicine, Biomed Central, vol. 3, No. 1, Apr. 28, 2005 (Apr. 28, 2005), p. 17.
Chinese Office Action and Search Report issued in Chinese Patent Application No. 201780087568.3 dated.
NCBI—Variable charge X-linked protein 3B [*Homo sapiens*], Accession: NP_001001888.3; Jul. 4, 2004.
Zou SW et al., Expression and localization of VCX/Y proteins and their possible involvement in regulation of ribosome assembly during spermatogenesis, *Cell Research*, No. 3., Jun. 30, 2003.
Zou SW, Preliminary study on the function of encoding protein of human testicular specific gene expression family VCX/Y; *Chinese Doctoral Dissertations Full-text Database Basic Science*; Nov. 15, 2006. (English abstract pp. 5 and 6).

* cited by examiner

*Primary Examiner* — Laura B Goddard
(74) *Attorney, Agent, or Firm* — Norton Rose Fulbright US LLP

(57) ABSTRACT

Provided herein are tumor-antigen VCX/Y specific peptides and engineered VCX/Y specific T cell receptors. Also provided herein are methods of generating VCX/Y-specific immune cells and their use for the treatment of cancer. In addition, the VCX/Y-specific peptides may be used as a vaccine.

34 Claims, 28 Drawing Sheets
Specification includes a Sequence Listing.

TRAV-14
Result Summary: Productive TRA rearranged sequence (no stop codon and in-frame junction)

V-GENE and allele  Homsap TRAV14/DV4*03 (F)  score = 1375  identity = 100.00% (276/276 nt)

J-GENE and allele  Homsap TRAJ37*01 F  score = 283  identity = 95.16% (59/62 nt)

FR-IMGT lengths, CDR-IMGT lengths and AA JUNCTION  [26.17.34.11]  [7.8.12]  CAMITSGNTGKLIF

TRAV-13.1
Result Summary: Unproductive TRA rearranged sequence (stop codons, out-of-frame junction) (a)

V-GENE and allele  Homsap TRAV13-1*02 (F)  score = 1345  identity = 99.63% (269/270 nt)

J-GENE and allele  Homsap TRAJ26*01 F  score = 282  identity = 96.67% (58/60 nt)

FR-IMGT lengths, CDR-IMGT lengths and AA JUNCTION  [26.17.34.11]  [6.7.X]  WG#DNYGQNFVF (2nd-CYS 104 not identified)

*FIG. 8*

TRBV-13

| Result Summary: | Productive TRB rearranged sequence (no stop codon and in-frame junction) | | |
|---|---|---|---|
| V-GENE and allele | Homsap TRBV13*01 F | score = 1360 | identity = 100.00% (273/273 nt) |
| J-GENE and allele | Homsap TRBJ1-1*01 F | score = 204 | identity = 91.67% (44/48 nt) |
| D-GENE and allele by IMGT/JunctionAnalysis | Homsap TRBD2*01 F | D-REGION is in reading frame 1 | |
| FR-IMGT lengths, CDR-IMGT lengths and AA JUNCTION | [26.17.37.10] | [5.6.13] | CASSPPGGGRTEAFF |

*FIG. 8 (Cont'd)*

SEQUENCE LISTING

<160> NUMBER OF SEQ ID NOS: 20

<210> SEQ ID NO 1
<211> LENGTH: 9
<212> TYPE: PRT
<213> ORGANISM: Artificial Sequence
<220> FEATURE:
<223> OTHER INFORMATION: VCX54 peptide

<400> SEQUENCE: 1

Gly Ala Ala Thr Lys Met Ala Ala Val
1               5

<210> SEQ ID NO 2
<211> LENGTH: 14
<212> TYPE: PRT
<213> ORGANISM: Artificial Sequence
<220> FEATURE:
<223> OTHER INFORMATION: VCX54 TCR alpha chain CDR3

<400> SEQUENCE: 2

Cys Ala Met Ile Thr Ser Gly Asn Thr Gly Lys Leu Ile Phe
1               5                   10

<210> SEQ ID NO 3
<211> LENGTH: 15
<212> TYPE: PRT
<213> ORGANISM: Artificial Sequence
<220> FEATURE:
<223> OTHER INFORMATION: VCX54 TCR beta chain CDR3

<400> SEQUENCE: 3

Cys Ala Ser Ser Pro Pro Gly Gly Gly Arg Thr Glu Ala Phe Phe
1               5                   10                  15

<210> SEQ ID NO 4
<211> LENGTH: 831
<212> TYPE: DNA
<213> ORGANISM: Artificial Sequence
<220> FEATURE:
<223> OTHER INFORMATION: VCX54 CTL Clone-7 TCR Alpha chain

<400> SEQUENCE: 4
atgtcacttt ctagcctgct gaaggtggtc acagcttcac tgtggctagg acctggcatt      60
gcccagaaga taactcaaac ccaaccagga atgttcgtgc aggaaaagga ggctgtgact     120
ctggactgca catatgacac cagtgatcca agttatggtc tattctggta caagcagccc     180
agcagtgggg aaatgatttt tcttatttat cagggggtctt atgaccagca aaatgcaaca     240
gaaggtcgct actcattgaa tttccagaag gcaagaaaat ccgccaacct tgtcatctcc     300
gcttcacaac tggggactc agcaatgtat ttctgtgcaa tgataacctc tggcaacaca      360
ggcaaactaa tctttgggca agggacaact ttacaagtaa accagatat ccagaaccct      420 gaccctgccg tgtaccagct gagagactct aaatccagtg acaagtctgt ctgcctattc     480
accgattttg attctcaaac aaatgtgtca caaagtaagg attctgatgt gtatatcaca     540
gacaaaactg tgctagacat gaggtctatg gacttcaaga gcaacagtgc tgtggcctgg     600
agcaacaaat ctgactttgc atgtgcaaac gccttcaaca cagcattat tccagaagac      660 accttcttcc ccagcccaga aagttcctgt gatgtcaagc tggtcgagaa aagctttgaa     720
acagatacga acctaaactt tcaaaaacctg tcagtgattg gttccgaat cctcctcctg      780 aaagtggccg ggtttaatct gctcatgacg ctgcggctgt ggtccagctg a               831

<210> SEQ ID NO 5
<211> LENGTH: 276
<212> TYPE: PRT
<213> ORGANISM: Artificial Sequence
<220> FEATURE:
<223> OTHER INFORMATION: VCX54 CTL Clone-7 TCR Alpha chain

<400> SEQUENCE: 5

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe

```
                    20                  25                  30
Val Gln Glu Lys Glu Ala Val Thr Leu Asp Cys Thr Tyr Asp Thr Ser
                35                  40                  45

Asp Pro Ser Tyr Gly Leu Phe Trp Tyr Lys Gln Pro Ser Ser Gly Glu
            50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Ile Thr Ser Gly Asn Thr Gly Lys Leu Ile Phe Gly Gln Gly
            115                 120                 125

Thr Thr Leu Gln Val Lys Pro Asp Ile Gln Asn Pro Asp Pro Ala Val
            130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
            195                 200                 205

Ala Asn Ala Phe Asn Asn Ser Ile Ile Pro Glu Asp Thr Phe Phe Pro
            210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275

<210> SEQ ID NO 6
<211> LENGTH: 963
<212> TYPE: DNA
<213> ORGANISM: Artificial Sequence
<220> FEATURE:
<223> OTHER INFORMATION: VCX54 CTL Clone-7 TCR Beta chain

<400> SEQUENCE: 6
atgcttagtc ctgacctgcc tgactctgcc tggaacacca ggctcctctg ccgtgtcatg      60
ctttgtctcc tgggagcagg ttcagtggct gctggagtca tccagtcccc aagacatctg     120
atcaaagaaa gagggaaac agccactctg aaatgctatc ctatccctag acacgacact     180
gtctactggt accagcaggg tccaggtcag gaccccagt cctcatttc gttttatgaa      240 aagatgcaga gcgataaagg aagcatccct gatcgattct cagctcaaca gttcagtgac     300
tatcattctg aactgaacat gagctccttg gagctggggg actcagccct gtacttctgt     360
gccagcagcc ccccgggcgg ggggcggact gaagctttct ttggacaagg caccagactc     420
acagttgtag aggacctgaa caaggtgttc ccacccgagg tcgctgtgtt tgagccatca     480
gaagcagaga tctcccacac ccaaaaggcc acactggtgt gcctggccac aggcttcttc     540
cctgaccacg tggagctgag ctggtgggtg aatgggaagg aggtgcacag tggggtcagc     600
```

```
acggacccgc agcccctcaa ggagcagccc gccctcaatg actccagata ctgcctgagc    660
agccgcctga gggtctcggc caccttctgg cagaaccccc gcaaccactt ccgctgtcaa    720
gtccagttct acgggctctc ggagaatgac gagtggaccc aggatagggc caaacccgtc    780
acccagatcg tcagcgccga ggcctggggt agagcagact gtggctttac ctcggtgtcc    840
taccagcaag gggtcctgtc tgccaccatc tctatgaga tcctgctagg gaaggccacc     900
ctgtatgctg tgctggtcag cgccttgtg ttgatggcca tggtcaagag aaaggatttc     960
tag                                                                  963
```

<210> SEQ ID NO 7
<211> LENGTH: 320
<212> TYPE: PRT
<213> ORGANISM: Artificial Sequence
<220> FEATURE:
<223> OTHER INFORMATION: VCX54 CTL Clone-7 TCR Beta chain

<400> SEQUENCE: 7

```
Met Leu Ser Pro Asp Leu Pro Asp Ser Ala Trp Asn Thr Arg Leu Leu
1               5                   10                  15

Cys Arg Val Met Leu Cys Leu Leu Gly Ala Gly Ser Val Ala Ala Gly
            20                  25                  30

Val Ile Gln Ser Pro Arg His Leu Ile Lys Glu Lys Arg Glu Thr Ala
        35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Pro Pro Gly Gly Gly
        115                 120                 125

Arg Thr Glu Ala Phe Phe Gly Gln Gly Thr Arg Leu Thr Val Val Glu
    130                 135                 140

Asp Leu Asn Lys Val Phe Pro Pro Glu Val Ala Val Phe Glu Pro Ser
145                 150                 155                 160

Glu Ala Glu Ile Ser His Thr Gln Lys Ala Thr Leu Val Cys Leu Ala
                165                 170                 175

Thr Gly Phe Phe Pro Asp His Val Glu Leu Ser Trp Trp Val Asn Gly
            180                 185                 190

Lys Glu Val His Ser Gly Val Ser Thr Asp Pro Gln Pro Leu Lys Glu
        195                 200                 205

Gln Pro Ala Leu Asn Asp Ser Arg Tyr Cys Leu Ser Ser Arg Leu Arg
    210                 215                 220

Val Ser Ala Thr Phe Trp Gln Asn Pro Arg Asn His Phe Arg Cys Gln
225                 230                 235                 240

Val Gln Phe Tyr Gly Leu Ser Glu Asn Asp Glu Trp Thr Gln Asp Arg
                245                 250                 255

Ala Lys Pro Val Thr Gln Ile Val Ser Ala Glu Ala Trp Gly Arg Ala
            260                 265                 270

Asp Cys Gly Phe Thr Ser Val Ser Tyr Gln Gln Gly Val Leu Ser Ala
        275                 280                 285
```

```
Thr Ile Leu Tyr Glu Ile Leu Leu Gly Lys Ala Thr Leu Tyr Ala Val
    290                 295                 300

Leu Val Ser Ala Leu Val Leu Met Ala Met Val Lys Arg Lys Asp Phe
305                 310                 315                 320

<210> SEQ ID NO 8
<211> LENGTH: 9
<212> TYPE: PRT
<213> ORGANISM: Artificial Sequence
<220> FEATURE:
<223> OTHER INFORMATION: VCX37 peptide

<400> SEQUENCE: 8

Lys Val Ala Lys Lys Gly Lys Ala Val
1               5

<210> SEQ ID NO 9
<211> LENGTH: 9
<212> TYPE: PRT
<213> ORGANISM: Artificial Sequence
<220> FEATURE:
<223> OTHER INFORMATION: VCX178 peptide

<400> SEQUENCE: 9

Ser Glu Met Glu Glu Leu Pro Ser Val
1               5

<210> SEQ ID NO 10
<211> LENGTH: 12
<212> TYPE: PRT
<213> ORGANISM: Artificial Sequence
<220> FEATURE:
<223> OTHER INFORMATION: VCX54 CTL Clone-7 TCR Alpha chain transmembrane
      domain

<400> SEQUENCE: 10

Lys Val Ala Gly Phe Asn Leu Leu Met Thr Leu Arg
1               5                   10

<210> SEQ ID NO 11
<211> LENGTH: 14
<212> TYPE: PRT
<213> ORGANISM: Artificial Sequence
<220> FEATURE:
<223> OTHER INFORMATION: VCX54 CTL Clone-7 TCR Beta chain transmembrane
      domain

<400> SEQUENCE: 11

Leu Tyr Ala Val Leu Val Ser Ala Leu Val Leu Met Ala Met
1               5                   10

<210> SEQ ID NO 12
<211> LENGTH: 9
<212> TYPE: PRT
<213> ORGANISM: Artificial Sequence
<220> FEATURE:
<223> OTHER INFORMATION: VCY-37

<400> SEQUENCE: 12

Lys Val Ala Glu Lys Gly Glu Ala Val
1               5

<210> SEQ ID NO 13
<211> LENGTH: 10
<212> TYPE: PRT
<213> ORGANISM: Artificial Sequence
<220> FEATURE:
```

```
<223> OTHER INFORMATION: VCX-58

<400> SEQUENCE: 13

Lys Met Ala Ala Val Glu Ala Pro Glu Ala
1               5                   10

<210> SEQ ID NO 14
<211> LENGTH: 9
<212> TYPE: PRT
<213> ORGANISM: Artificial Sequence
<220> FEATURE:
<223> OTHER INFORMATION: VCX-59

<400> SEQUENCE: 14

Met Ala Ala Val Glu Ala Pro Glu Ala
1               5

<210> SEQ ID NO 15
<211> LENGTH: 834
<212> TYPE: DNA
<213> ORGANISM: Artificial Sequence
<220> FEATURE:
<223> OTHER INFORMATION: VCY-37 CTL TCR Alpha Chain

<400> SEQUENCE: 15
atgctgactg ccagcctgtt gagggcagtc atagcctcca tctgtgttgt atccagcatg      60
gctcagaagg taactcaagc gcagactgaa atttctgtgg tggagaagga ggatgtgacc     120
ttggactgtg tgtatgaaac ccgtgatact acttattact tattctggta caagcaacca     180
ccaagtggag aattggtttt ccttattcgt cggaactctt ttgatgagca aaatgaaata     240
agtggtcggt attcttggaa cttccagaaa tccaccagtt ccttcaactt caccatcaca     300
gcctcacaag tcgtggactc agcagtatac ttctgtgctc tgagcttact atcttataac     360
accgacaagc tcatctttgg gactgggacc agattacaag tctttccaaa tatccagaac     420
cctgaccctg ccgtgtacca gctgagagac tctaaatcca gtgacaagtc tgtctgccta     480
ttcaccgatt ttgattctca aacaaatgtg tcacaaagta aggattctga tgtgtatatc     540
acagacaaaa ctgtgctaga catgaggtct atggacttca gagcaacagt gctgtggcc     600 tggagcaaca atctgactt tgcatgtgca aacgccttca acaacagcat tattccagaa     660 gacacctct tccccagccc agaaagttcc tgtgatgtca agctggtcga gaaaagcttt     720
gaaacagata cgaacctaaa ctttcaaaac ctgtcagtga ttgggttccg aatcctcctc     780
ctgaaagtgg ccgggtttaa tctgctcatg acgctgcggc tgtggtccag ctga           834

<210> SEQ ID NO 16
<211> LENGTH: 277
<212> TYPE: PRT
<213> ORGANISM: Artificial Sequence
<220> FEATURE:
<223> OTHER INFORMATION: VCY-37 CTL TCR Alpha Chain

<400> SEQUENCE: 16

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60
```

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
            100                 105                 110

Ala Leu Ser Leu Leu Ser Tyr Asn Thr Asp Lys Leu Ile Phe Gly Thr
        115                 120                 125

Gly Thr Arg Leu Gln Val Phe Pro Asn Ile Gln Asn Pro Asp Pro Ala
130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
        275

<210> SEQ ID NO 17
<211> LENGTH: 939
<212> TYPE: DNA
<213> ORGANISM: Artificial Sequence
<220> FEATURE:
<223> OTHER INFORMATION: VCY-37 CTL TCR Beta Chain

<400> SEQUENCE: 17
atgggcacca gcctcctctg ctggatggcc ctgtgtctcc tgggggcaga tcacgcagat      60
actggagtct cccaggaccc cagacacaag atcacaaaga gggacagaa tgtaactttc      120 aggtgtgatc aatttctga acacaaccgc ctttattggt accgacagac cctggggcag      180
ggcccagagt ttctgactta cttccagaat gaagctcaac tagaaaaatc aaggctgctc      240
agtgatcggt tctctgcaga gaggcctaag ggatctttct ccaccttgga gatccagcgc      300
acagagcagg gggactcggc catgtatctc tgtgccagca gcacccccgg gccctctggg      360
gccaacgtcc tgactttcgg ggccggcagc aggctgaccg tgctgaggga cctgaaaaac      420
gtgttcccac ccgaggtcgc tgtgtttgag ccatcagaag cagagatctc ccacacccaa      480
aaggccacac tggtgtgcct ggccacaggc ttcttccctg accacgtgga gctgagctgg      540
tgggtgaatg gaaggaggt gcacagtggg gtcagcacgg accgcagcc cctcaaggag      600 cagcccgccc tcaatgactc cagatactgc ctgagcagcc gcctgagggt ctcggccacc      660
ttctggcaga accccgcaa ccacttccgc tgtcaagtcc agttctacgg gctctcggag      720
aatgacgagt ggaccccagga tagggccaaa cccgtcaccc agatcgtcag cgccgaggcc      780

-continued

```
tggggtagag cagactgtgg ctttacctcg gtgtcctacc agcaaggggt cctgtctgcc      840
accatcctct atgagatcct gctagggaag gccaccctgt atgctgtgct ggtcagcgcc      900
cttgtgttga tggccatggt caagagaaag gatttctga                             939
```

<210> SEQ ID NO 18
<211> LENGTH: 312
<212> TYPE: PRT
<213> ORGANISM: Artificial Sequence
<220> FEATURE:
<223> OTHER INFORMATION: VCY-37 CTL TCR Beta Chain

<400> SEQUENCE: 18

```
Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Thr Pro Gly Pro Ser Gly Ala Asn Val Leu Thr Phe Gly Ala
        115                 120                 125

Gly Ser Arg Leu Thr Val Leu Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Val Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Phe
305                 310
```

<210> SEQ ID NO 19
<211> LENGTH: 13

```
<212> TYPE: PRT
<213> ORGANISM: Artificial Sequence
<220> FEATURE:
<223> OTHER INFORMATION: VCY-37 CTL TCR Alpha Chain CDR3

<400> SEQUENCE: 19

Ala Leu Ser Leu Leu Ser Tyr Asn Thr Asp Lys Leu Ile
1               5                   10

<210> SEQ ID NO 20
<211> LENGTH: 14
<212> TYPE: PRT
<213> ORGANISM: Artificial Sequence
<220> FEATURE:
<223> OTHER INFORMATION: VCY-37 CTL TCR Beta Chain CDR3

<400> SEQUENCE: 20

Ala Ser Ser Thr Pro Gly Pro Ser Gly Ala Asn Val Leu Thr
1               5                   10
```

HLA-RESTRICTED VCX/Y PEPTIDES AND T CELL RECEPTORS AND USE THEREOF

The present application is a national phase application under 35 U.S.C. § 371 of International Application No. PCT/US2017/068701 filed on Dec. 28, 2017 and claims the priority benefit of U.S. Provisional Application Ser. No. 62/440,233, filed Dec. 29, 2016, and Ser. No. 62/595,422, filed Dec. 6, 2017, the entire contents of each application being hereby incorporated by reference.

INCORPORATION OF SEQUENCE LISTING

The sequence listing that is contained in the file named "UTFCP1310WO_ST25.txt", which is 19 KB (as measured in Microsoft Windows®) and was created on Dec. 27, 2017, is filed herewith by electronic submission and is incorporated by reference herein.

BACKGROUND OF THE INVENTION

1. Field of the Invention

The present invention relates generally to the fields of immunology and medicine. More particularly, it concerns tumor antigen peptides and uses thereof for the treatment of cancer.

2. Description of Related Art

T cell based therapies have shown significant promise as a method for treating many cancers; unfortunately, this approach has also been hindered by a paucity of immunogenic antigen targets for common cancers and potential toxicity to non-cancerous tissues. These T cell based therapies can include ACT (adoptive cell transfer) and vaccination approaches. ACT generally involves which involves infusing a large number of autologous activated tumor-specific T cells into a patient, e.g., to treat a cancer. ACT has resulted in therapeutic clinical responses in melanoma patients (Yee 2002; Dudley 2002; Yee 2014). Generally, to develop effective anti-tumor T cell responses, the following three steps are normally required: priming and activating antigen-specific T cells, migrating activated T cells to tumor site, and recognizing and killing tumor by antigen-specific T cells. The choice of target antigen is important for induction of effective antigen-specific T cells.

While several tumor-associated antigens have been identified for melanoma and a handful of other solid tumor malignancies, there are few immunogenic targets for pancreatic, ovarian, gastric, lung, cervical, breast, and head and neck cancer. Identification and validation of novel epitopes and target antigens for these common and difficult to treat malignancies is warranted.

SUMMARY OF THE INVENTION

The present disclosure provides, in some embodiments, VCX/Y (e.g., VCX1, VCX2, VCX3A, VCX3B, and VCY) peptides that may be used in adoptive T cell therapies. In some embodiments, the peptides may be used to expand VCX/Y-specific T cells in vitro that are administered to a mammalian subject, such as a human patient, to treat a disease (e.g., a cancer). In further embodiments, the T cells are genetically engineered to express T cell receptors (TCRs) with antigenic specificity for VCX/Y. In other embodiments, the peptides may be administered to a mammalian subject to induce an immune response or vaccinate the subject against the peptide, and such an immune response may be useful to treat or reduce the chances of getting or relapsing from a disease, such as a cancer.

In one embodiment, the present disclosure provides an isolated VCX/Y peptide of 35 amino acids in length or less comprising an amino acid sequence having at least 90% sequence identity to SEQ ID NO: 1 (GAATKMAAV), 8 (KVAKKGKAV), 9 (SEMEELPSV), 12 (KVAEKGEAV), 13 (KMAAVEAPEA), or 14 (MAAVEAPEA) wherein the peptide selectively binds HLA-A2. In some aspects, the peptide comprises an amino acid sequence having at least 91, 92, 93, 94, 95, 96, 97, 98, 99, or 100 percent sequence identity to SEQ ID NO:1, 8, 9, 12, 13, or 14. In particular aspects, the human class I HLA-A2 protein is HLA-A*0201.

In certain aspects, the peptide is 30 amino acids in length or less, such as 29, 28, 27, 26, 25, 24, 23, 22, 21, 20, 19, 18, 17, 16, 15, 14, 13, 12, 11, or 10 amino acids in length.

In another embodiment, there is provided a pharmaceutical composition comprising the isolated VCX/Y peptide of the embodiments and a pharmaceutical carrier. In some aspects, the pharmaceutical composition is formulated for parenteral administration, intravenous injection, intramuscular injection, inhalation, or subcutaneous injection. In certain aspects, the peptide is comprised in a liposome, nanoparticle (e.g., lipid-containing nanoparticle), or in a lipid-based carrier. In some aspects, the pharmaceutical preparation is formulated for injection or inhalation as a nasal spray.

A further embodiment provides an isolated nucleic acid encoding the VCX/Y peptide of the embodiments. Also provided herein is a vector comprising a contiguous sequence consisting of the nucleic acid encoding the VCX/Y peptide.

In yet another embodiment, there is provided a method of promoting an immune response in a subject, comprising administering an effective amount of the VCX/Y peptide of the embodiments to the subject, wherein the peptide induces antigen-specific T cells in the subject. In some aspects, the subject is diagnosed with cancer. In certain aspects, the cancer is pancreatic, ovarian, gastric, or breast cancer. In particular aspects, the subject is a human.

In additional aspects, the method further comprises administering at least a second anti-cancer therapy. In some aspects, the second anti-cancer therapy is selected from the group consisting of a chemotherapy, a radiotherapy, an immunotherapy, or a surgery. In particular aspects, the immunotherapy is an immune checkpoint inhibitor. In one specific aspects, the immune checkpoint inhibitor is an anti-PD1 monoclonal antibody.

A further embodiment provides a method of producing VCX/Y-specific T cells comprising obtaining a starting population of T cells, and contacting the starting population of T cells with the VCX/Y peptide of the embodiments, thereby generating VCX/Y-specific T cells. In some aspects, contacting is further defined as co-culturing the starting population of T cells with antigen presenting cells (APCs), wherein the APCs present the VCX/Y peptide of the embodiments on their surface. In particular aspects, the APCs are dendritic cells. In some aspects, the starting population of T cells are CD8$^+$ T cells. In certain aspects, the T cells are cytotoxic T lymphocytes (CTLs). In some aspects, obtaining comprises isolating the starting population of T cells from peripheral blood mononuclear cells (PBMCs). Also provided herein is a pharmaceutical composition comprising the VCX/Y-specific T cells produced by the methods herein.

An even further embodiment provides an antigen receptor, such as a T cell receptor (TCR) or chimeric antigen receptor (CAR), with antigenic specificity for VCX/Y. Another embodiment provides T cells engineered to express a VCX/Y-specific TCR or CAR. In certain aspects, the TCR binds HLA-A2, such as HLA-A*0201. In some aspects, the TCR comprises an alpha chain CDR3 having at least 95% (e.g., 96%, 97%, 98%, 99%, or 100%) identity to the amino acid sequence of SEQ ID NO:2 or 19 and/or a beta chain CDR3 having at least 95% (e.g., 96%, 97%, 98%, 99%, or 100%) identity to the amino acid sequence of SEQ ID NO:3 or 20. In some aspects, the TCR comprises an alpha chain having at least 90% (e.g., 91%, 92%, 93%, 94%, 95%, 96%, 97%, 98%, 99%, or 100%) identity to the amino acid sequence of SEQ ID NO:5 or 16 and/or a beta chain having at least 90% (e.g., 91%, 92%, 93%, 94%, 95%, 96%, 97%, 98%, 99%, or 100%) identity to the amino acid sequence of SEQ ID NO:7 or 18. In particular aspects, the TCR comprises an alpha chain of SEQ ID NO:5 or 16 and/or a beta chain of SEQ ID NO:7 or 18.

In some aspects, the VCX/Y-specific antigen receptor comprises an intracellular signaling domain, a transmembrane domain, and/or an extracellular domain. In certain aspects, DNA encoding the TCR or CAR is integrated into the genome of the cell. In some aspects, the extracellular domain of the TCR or CAR comprises a VCX/Y-binding region. For example, the VCX/Y-binding region may be a F(ab')2, Fab', Fab, Fv, or scFv. In certain aspects, the intracellular signaling domain is a T-lymphocyte activation domain. For example, the intracellular signaling domain of the TCR may comprise CD3ξ, CD3ε, CD3γ, CD3δ, CD8, CD27, CD28, OX40/CD134, 4-1BB/CD137, GITR/CD357, FcεRIγ, ICOS/CD278, ILRB/CD122, IL-2RG/CD132, DAP molecules, CD70, cytokine receptor, CD40, or a combination thereof. In certain aspects, the transmembrane domain of the TCR comprises CD28 transmembrane domain, ICOS transmembrane domain, NKG2D transmembrane domain, DAP molecules transmembrane domain, IgG4Fc hinge, Fc regions, CD4 transmembrane domain, the CD3ξ transmembrane domain, cysteine mutated human CD3ξ domain, CD16 transmembrane domain, CD8 transmembrane domain, or erythropoietin receptor transmembrane domain.

In some embodiments, the present disclosure provides soluble TCRs, such as a VCX/Y TCR provided herein. In some aspects, the TCR is conjugate to a detectable label or therapeutic agent. In some aspects, soluble TCRs are used to deliver a therapeutic agent, for example a cytotoxic compound or an immunostimulating compound, to cells presenting a particular antigen. In some aspects, the TCR is linked to another molecule that delivers a cell in proximity to the tumor. In certain aspects, the TCR delivers a toxin, a cytokine, costimulatory ligand, or inhibitor ligand, such as to direct a molecule, cell or compound to the target cells expressing the peptide-MHC. In particular aspects, the TCR is conjugated to anti-CD3.

A further embodiment provides a multivalent TCR complex comprising a plurality of the VCX/Y antigenic receptor of the above embodiments, such as a VCX/Y TCR. In some aspects, the multivalent TCR comprises 2, 3, 4 or more TCRs associated with one another. In certain aspects, the multivalent TCR is present in a lipid bilayer or is attached to a particle.

In yet another embodiment, there is provided a polypeptide encoding the TCR of the embodiments. Further provided is a polynucleotide encoding said polypeptide and an expression vector (e.g., a viral vector, such as a retroviral vector) comprising the polynucleotide. In some aspects, the vector further comprises a linker domain. In certain aspects, the linker domain comprises one or more cleavage sites. In some aspects, the one or more cleavage sites are a Furin cleavage site and/or a P2A cleavage site which may be separated by a spacer (e.g., SGSG or GSG).

In a further embodiment, there is provided a host cell engineered to express the TCR of the embodiments. In some aspects, the cell is an immune cell. In certain aspects, the cell is an NK cell, invariant NK cell, NKT cell, mesenchymal stem cell (MSC), or induced pluripotent stem (iPS) cell. In some aspects, the cell is isolated from the umbilical cord. In certain aspects, the immune cell is a T cell or peripheral blood lymphocyte. In particular aspects, the T cell is a CD8$^+$ T cell, CD4$^+$ T cell, or γδ T cell. In some aspects, the T cell is a regulatory T cell (Treg). In some aspects, the cell is allogeneic or autologous.

In another embodiment, there is provided a method for engineering the immune cell of the embodiments comprising contacting said immune cell with the TCR of the embodiments or the expression vector of encoding said TCR. In some aspects, the immune cell is a T cell or peripheral blood lymphocyte. In certain aspects, contacting is further defined as transfecting or transducing. In some aspects, transfecting comprises electroporating RNA encoding the TCR of the embodiments into the immune cell. In some aspects, the method further comprises generating viral supernatant from the expression vector of the embodiments prior to transducing the immune cell. In some aspects, the immune cell is a stimulated lymphocyte. In certain aspects, the stimulated lymphocyte is a human lymphocyte. In some aspects, stimulating comprises OKT3 and/or IL-2. In certain aspects, the method further comprises sorting the immune cells to isolate TCR engineered T cells. In some aspects, the method further comprises performing T cell cloning by serial dilution. In certain aspects, the method further comprises expansion of the T cell clone by the rapid expansion protocol.

Another embodiment provides a method of treating cancer in a subject comprising administering an effective amount of the VCX/Y-specific T cells or TCR-engineered host cells of the embodiments to the subject. Also provided herein is a composition comprising an effective amount of the VCX/Y-specific T cell or TCR-engineered host cells of the embodiments for the treatment of cancer in a subject. In some aspects, the cancer is thymoma, bladder cancer, uterine carcinoma, melanoma, sarcoma, cervix cancer, or head and neck cancer. In particular aspects, the subject is a human. In some aspects, the cells are autologous or allogeneic. In some aspects, the subject is determined to have cancer cells which express VCX/Y. In particular aspects, the subject is identified to have an HLA-A*0201 allele.

In some aspects, the host cell is a T cell, peripheral blood lymphocyte, NK cell, invariant NK cell, NKT cell, mesenchymal stem cell (MSC), or induced pluripotent stem (iPS) cell. In certain aspects, the host cell is isolated from the umbilical cord. In some aspects, the host cell is autologous or allogeneic. In certain aspects, the T cell is a CD8$^+$ T cell, CD4$^+$ T cell, or γδ T cell.

In certain aspects, the method further comprises lymphodepletion of the subject prior to administration of the antigen-specific T cells. In some aspects, lymphodepletion comprises administration of cyclophosphamide and/or fludarabine.

In some aspects, the method further comprises administering at least a second therapeutic agent. In certain aspects, the at least a second therapeutic agent comprises chemotherapy, immunotherapy, surgery, radiotherapy, or biotherapy. In particular aspects, the immunotherapy is an immune checkpoint inhibitor. In one specific aspects, the immune checkpoint inhibitor is an anti-PD1 monoclonal antibody.

In certain aspects, the VCX/Y-specific T cells and/or the at least a second therapeutic agent are administered intravenously, intraperitoneally, intratracheally, intratumorally, intramuscularly, endoscopically, intralesionally, percutaneously, subcutaneously, regionally, or by direct injection or perfusion.

In some aspects, the subject is determined to have cancer cells which express a protein of the VCX/Y family. In particular aspects, the protein is VCX1, VCX2, VCX3A, VCX3B, or VCY.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 8: VCX54 CTL clone (C7) TCR alpha chain and beta chain analysis. Sequence analysis from IMGT database shows the VCX54 CTL clone (C7) TCR usage as TRAV-14 and TRBV-13. The corresponding CDR3 amino acid sequences of TCR-α and TCR-β are indicated.

DESCRIPTION OF ILLUSTRATIVE EMBODIMENTS

Figure 1A:
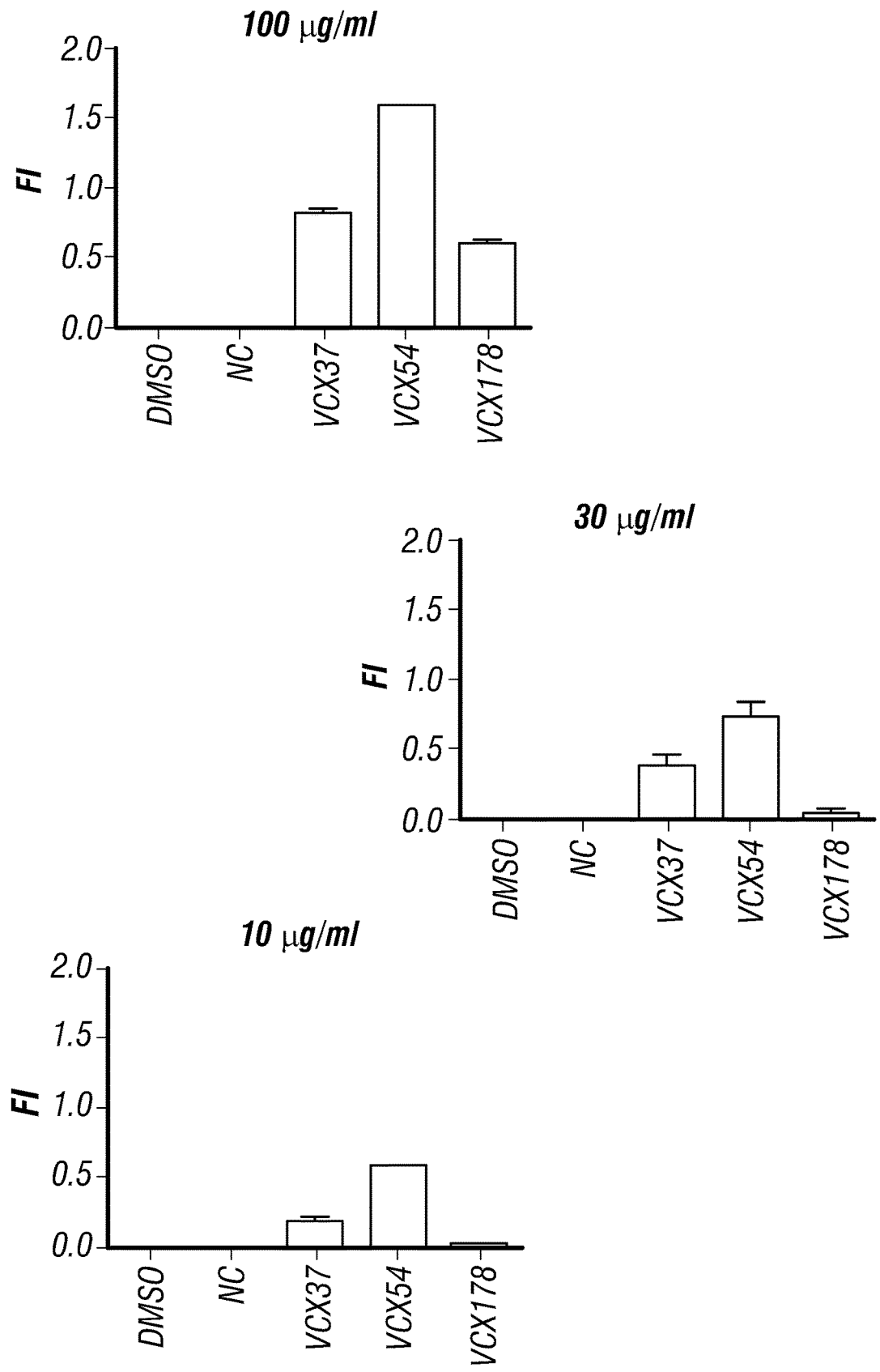
FIGS. 1A-1B: HLA-A2 stabilize expression assay of T2 cells. (A) Binding assay of predicted peptides after 18 hr incubation with T2 cells shows HLA-A2 expression as a fluorescence index. (B) Western Blot detection of expression of VCX member, VCX1, VCX3A and VCY in lung cancer cell lines. H522, H2023, H1395, H82, H1355, H1755 and DFC1032 express HLA-A0201; H647 express HLA-A1101; PC-9 express HLA-A0206 and HLA-A2402.

For patients with many different cancer types, T cell based immunotherapies represent a promising approach with proven efficacy. However, antigen-specific T cell therapy for most cancer types is not feasible due to the lack of tumor-associated antigens currently known, which has stalled their clinical development. Studies in the present disclosure identified novel VCX/Y family derived HLA-A2 restricted peptide epitopes found in all of the VCX/Y family members including VCX1, VCX2, VCX3A, VCX3B, and VCY. Using the peptide epitopes, antigen-specific cytotoxic T lymphocytes (CTLs) were generated from patient peripheral blood mononuclear cells (PBMCs) that recognized the endogenously-presented antigen on HLA-matched allogeneic tumor cell lines, leading to tumor cell killing. Thus, these antigen-specific CTLs may be used to target solid cancers (e.g., pancreatic, ovarian, gastric, and breast cancer).

Accordingly, the present disclosure provides tumor antigen-specific peptides, such as to tumor antigen VCX/Y, for the use as immunotherapy for the treatment of a cancer. An exemplary VCX/Y peptide, VCX54 (e.g. comprising SEQ ID NO:1), is disclosed herein, the sequence of which is shared with all VCX/Y family members including VCX1, VCX2, VCX3A, VCX3B, and VCY. Other VCX/Y peptides include VCX-37 (SEQ ID NO:8), VCX-178 (SEQ ID NO:9), VCY-37 (SEQ ID NO:12), VCX-58 (SEQ ID NO:13), and VCX-59 (SEQ ID NO:14). For example, a tumor antigen-specific peptide may be contacted with or used to stimulate a population of T cells to induce proliferation of the T cells that recognize or bind the tumor antigen-specific peptide. In other embodiments, a VCX/Y-specific peptide of the present disclosure may be administered to a subject, such as a human patient, to enhance the immune response of the subject against a cancer.

A VCX/Y-specific peptide may be included in an active immunotherapy (e.g., a cancer vaccine) or a passive immunotherapy (e.g., an adoptive immunotherapy). Active immunotherapies include immunizing a subject with a purified tumor antigen or an immunodominant VCX/Y-specific peptide (native or modified); alternately, antigen presenting cells pulsed with a VCX/Y-specific peptide (or transfected with genes encoding the tumor antigen) may be administered to a subject. The VCX/Y-specific peptide may be modified or contain one or more mutations such as, e.g., a substitution mutation. Passive immunotherapies include adoptive immunotherapies. Adoptive immunotherapies generally involve administering cells to a subject, wherein the cells (e.g., cytotoxic T cells) have been sensitized in vitro to the VCX/Y-specific peptide (see, e.g., U.S. Pat. No. 7,910,109).

In particular, a patient's own VCX/Y-specific T cells can be generated ex vivo for effective immune-based therapies within a short period of time, such as 6 to 8 weeks. The T cells may be isolated and expanded from autologous or allogeneic T cells (e.g., CD4$^+$ T cells, CD8$^+$ T cells, γδ T cells and Tregs) isolated from peripheral blood, such as with the tetramer guided sorting and rapid expansion protocol (REP). Next, the peptide or corresponding coded polynucleotides can be loaded to HLA-A2 positive dendritic cells, LCL, PBMC, or artificial antigen presenting cells (aAPCs), and then co-cultured with the T cells by several rounds of stimulation to generate antigen-specific CTL cell lines or clones. Furthermore, with manipulation of immune modulating parameters, the effector function and long term persistence in vivo of these expanded antigen specific T cells can be enhanced. These autologous CTL cells can be used for adoptive immunotherapy for VCX/Y and HLA-A2 positive cancer patients. Further, other VCX/Y-specific cells that can be generated from the present disclosure include autologous or allogeneic NK cells, invariant NK cells, NKT cells, mesenchymal stem cells (MSCs), and induced pluripotent stem (iPS) cells. These cells may be isolated from blood or the umbilical cord.

In another method, antigen-specific cells can be generated by using the VCX54 TCR provided herein (e.g., SEQ ID NOs:2-7) or the VCY37 TCR provided herein (e.g., SEQ ID NOs:15-20). In this method, the TCR sequence is inserted into a vector (e.g., retroviral or lentiviral vector) which is introduced into host cells, such as T cells (e.g., CD4$^+$ T cells, CD8$^+$ T cells, γδ T cells, and Tregs), NK cells, invariant NK cells, NKT cells, mesenchymal stem cells (MSCs), induced pluripotent stem (iPS) cells, and PBMCs, to generate antigen-specific cells which can be used for adoptive cell therapy for cancer patients.

In addition, the present disclosure provides soluble TCRs which can be used to treat HLA-A2 positive cancer patients directly. The soluble bispecific T cell-engaging molecules are generated by linking the VCX54 TCR or VCY37 TCR to CD3-specific Fab fragments. The T cell-engaging TCR can bind the tumor cell surface by presenting the respective peptide/MHC complex and the Fab fragments then crosslink TCRs on the surface of antigen-experienced CD8$^+$ T cells, resulting in cellular activation and elimination of the target cell. Thus, this soluble bispecific TCR constructs can be used for treating the cancer patients directly.

Finally, the soluble TCR can be used as a probe for diagnostic evaluation of peptide/MHC in tumor cells or to direct therapeutic molecules to the tumor site. This soluble TCR molecule also could be labeled with tracers such as a fluorescent probe or radioactive probe, and then used for diagnostic evaluation of the presentation of peptide/MHC in tumor cells. Furthermore, this soluble TCR molecule could be linked with therapeutic molecules such as toxin, and then direct these therapeutic molecules to the tumor sites for the treatment of cancer patients.

I. Definitions

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a T cell therapy.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject. In some embodiments, the dosage of antigen-specific T cell infusion may comprise about 100 million to about 30 billion cells, such as 10, 15, or 20 billion cells.

The term "immune checkpoint" refers to a molecule such as a protein in the immune system which provides signals to its components in order to balance immune reactions. Known immune checkpoint proteins comprise CTLA-4, PD1 and its ligands PD-L1 and PD-L2 and in addition LAG-3, BTLA, B7H3, B7H4, TIM3, KIR. The pathways involving LAG3, BTLA, B7H3, B7H4, TIM3, and KIR are recognized in the art to constitute immune checkpoint pathways similar to the CTLA-4 and PD-1 dependent pathways (see e.g. Pardoll, 2012; Mellman et al., 2011.

An "immune checkpoint inhibitor" refers to any compound inhibiting the function of an immune checkpoint protein. Inhibition includes reduction of function and full blockade. In particular the immune checkpoint protein is a human immune checkpoint protein. Thus the immune checkpoint protein inhibitor in particular is an inhibitor of a human immune checkpoint protein.

As used herein, a "protective immune response" refers to a response by the immune system of a mammalian host to a cancer. A protective immune response may provide a therapeutic effect for the treatment of a cancer, e.g., decreasing tumor size or increasing survival.

As used herein, the term "antigen" is a molecule capable of being bound by an antibody or T-cell receptor. An antigen may generally be used to induce a humoral immune response and/or a cellular immune response leading to the production of B and/or T lymphocytes.

The terms "tumor-associated antigen," "tumor antigen" and "cancer cell antigen" are used interchangeably herein. In each case, the terms refer to proteins, glycoproteins or carbohydrates that are specifically or preferentially expressed by cancer cells.

The term "chimeric antigen receptors (CARs)," as used herein, may refer to artificial T-cell receptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising a tumor associated antigen binding region. In particular aspects, CARs comprise fusions of single-chain variable fragments (scFv) derived from monoclonal antibodies, fused to CD3-zeta a transmembrane domain and endodomain. The specificity of other CAR designs may be derived from ligands of receptors (e.g., peptides) or from pattern-recognition receptors, such as Dectins. In certain cases, the spacing of the antigen-recognition domain can be modified to reduce activation-induced cell death. In certain cases, CARs comprise domains for additional co-stimulatory signaling, such as CD3ζ, FcR, CD27, CD28, CD137, DAP10, and/or OX40. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

A polynucleotide or polynucleotide region (or a polypeptide or polypeptide region) has a certain percentage (for example, 80%, 85%, 90%, or 95%) of "sequence identity" or "homology" to another sequence means that, when aligned, that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR.

II. VCX/Y Peptides

Embodiments of the present disclosure concern tumor antigen-specific peptides, such as to the VCX/Y tumor antigen. In particular embodiments, the tumor antigen-specific peptides have the amino acid sequence of a VCX/Y peptide (GAATKMAAV: SEQ ID NO:1; or SEQ ID NOs: 8, 9, 12, 13, or 14). The tumor antigen-specific peptide may have an amino acid sequence with at least 80, 85, 90, 95, 96, 97, 98, 99, or 100 percent sequence identity with the peptide sequence of SEQ ID NO:1, 8, 9, 12, 13, or 14.

As used herein, the term "peptide" encompasses amino acid chains comprising 7-35 amino acids, preferably 8-35 amino acid residues, and even more preferably 8-25 amino acids, or 7, 8, 9, 10, 11, 12, 13, 14, 15, 16, 17, 18, 19, 20, 21, 22, 23, 24, 25, 26, 27, 28, 29, 30, 31, 32, 33, 34, or 35 amino acids in length, or any range derivable therein. For example, a VCX/Y peptide of the present disclosure may, in some embodiments, comprise or consist of the VCX54 peptide of SEQ ID NO:1 or the peptides of SEQ ID NO:8, 9, 12, 13, or 14. As used herein, an "antigenic peptide" is a peptide which, when introduced into a vertebrate, can stimulate the production of antibodies in the vertebrate, i.e., is antigenic, and wherein the antibody can selectively recognize and/or bind the antigenic peptide. An antigenic peptide may comprise an immunoreactive VCX/Y peptide, and may comprise additional sequences. The additional sequences may be derived from a native antigen and may be heterologous, and such sequences may, but need not, be immunogenic. In some embodiments, a tumor antigen-specific peptide (e.g., a VCX/Y peptide) can selectively bind with HLA-A2, particularly HLA-A*0201. In certain embodiments, the VCX/Y peptide is 8, 9, 10, 11, 12, 13, 14, 15, 16, 17, 18, 19, 20, 21, 22, 23, 24, 25, 26, 27, 28, 29, 30, 31, 32, 33, 34, or 35 amino acids in length, or any range derivable therein. Preferably, the tumor antigen-specific peptide (e.g., a VCX/Y peptide) is from 8 to 35 amino acids in length. In some embodiments, the tumor antigen-specific peptide (e.g., a VCX/Y peptide) is from 8 to 10 amino acids in length.

As would be appreciated by one of skill in the art, MHC molecules can bind peptides of varying sizes, but typically not full length proteins. While MHC class I molecules have been traditionally described to bind to peptides of 8-11 amino acids long, it has been shown that peptides 15 amino acids in length can bind to MHC class I molecules by bulging in the middle of the binding site or extending out of the MHC class I binding groove (Guo et al., 1992; Burrows et al., 2006; Samino et al., 2006; Stryhn et al., 2000; Collins et al., 1994; Blanchard and Shastri, 2008). Further, recent studies also demonstrated that longer peptides may be more efficiently endocytosed, processed, and presented by antigen-presenting cells (Zwaveling et al., 2002; Bijker et al., 2007; Melief and van der Burg, 2008; Quintarelli et al., 2011). As demonstrated in Zwaveling et al. (2002) peptides up to 35 amino acids in length may be used to selectively bind a class II MHC and are effective. As would be immediately appreciated by one of skill, a naturally occurring full-length tumor antigen, such as VCX/Y, would not be useful to selectively bind a class II MHC such that it would be endocytosed and generate proliferation of T cells. Generally, the naturally occurring full-length tumor antigen proteins do not display these properties and would thus not be useful for these immunotherapy purposes.

In certain embodiments, a tumor antigen-specific peptide (e.g., a VCX/Y peptide) is immunogenic or antigenic. As shown in the below examples, various tumor antigen-specific peptides (e.g., a VCX/Y peptide) of the present disclosure can promote the proliferation of T cells. It is anticipated that such peptides may be used to induce some degree of protective immunity.

A tumor antigen-specific peptide (e.g., a VCX/Y peptide) may be a recombinant peptide, synthetic peptide, purified peptide, immobilized peptide, detectably labeled peptide, encapsulated peptide, or a vector-expressed peptide (e.g., a peptide encoded by a nucleic acid in a vector comprising a heterologous promoter operably linked to the nucleic acid). In some embodiments, a synthetic tumor antigen-specific peptide (e.g., a VCX/Y peptide) may be administered to a subject, such as a human patient, to induce an immune response in the subject. Synthetic peptides may display certain advantages, such as a decreased risk of bacterial contamination, as compared to recombinantly expressed peptides. A tumor antigen-specific peptide (e.g., a VCX/Y peptide) may also be comprised in a pharmaceutical composition such as, e.g., a vaccine composition, which is formulated for administration to a mammalian or human subject.

A. Cell Penetrating Peptides

In some embodiments, an immunotherapy may utilize a tumor antigen-specific peptide (e.g., a VCX/Y peptide) of the present disclosure that is associated with a cell penetrator, such as a liposome or a cell penetrating peptide (CPP). Antigen presenting cells (such as dendritic cells) pulsed with peptides may be used to enhance antitumour immunity (Celluzzi et al., 1996; Young et al., 1996). Liposomes and CPPs are described in further detail below. In some embodiments, an immunotherapy may utilize a nucleic acid encoding a tumor antigen-specific peptide (e.g., a VCX/Y peptide) of the present disclosure, wherein the nucleic acid is delivered, e.g., in a viral vector or non-viral vector.

A tumor antigen-specific peptide (e.g., a VCX/Y peptide) may also be associated with or covalently bound to a cell penetrating peptide (CPP). Cell penetrating peptides that may be covalently bound to a tumor antigen-specific peptide (e.g., a VCX/Y peptide) include, e.g., HIV Tat, herpes virus VP22, the *Drosophila* Antennapedia homeobox gene product, signal sequences, fusion sequences, or protegrin I. Covalently binding a peptide to a CPP can prolong the presentation of a peptide by dendritic cells, thus enhancing antitumour immunity (Wang and Wang, 2002). In some embodiments, a tumor antigen-specific peptide (e.g., the VCX/Y peptide) of the present disclosure (e.g., comprised within a peptide or polyepitope string) may be covalently bound (e.g., via a peptide bond) to a CPP to generate a fusion protein. In other embodiments, a tumor antigen-specific peptide (e.g., a VCX/Y peptide) or nucleic acid encoding a tumor antigen-specific peptide may be encapsulated within or associated with a liposome, such as a mulitlamellar, vesicular, or multivesicular liposome, an exocytic vesicle or exosome.

As used herein, "association" means a physical association, a chemical association or both. For example, an association can involve a covalent bond, a hydrophobic interaction, encapsulation, surface adsorption, or the like.

As used herein, "cell penetrator" refers to a composition or compound which enhances the intracellular delivery of the peptide/polyepitope string to the antigen presenting cell. For example, the cell penetrator may be a lipid which, when associated with the peptide, enhances its capacity to cross the plasma membrane. Alternatively, the cell penetrator may be a peptide. Cell penetrating peptides (CPPs) are known in the art, and include, e.g., the Tat protein of HIV (Frankel and Pabo, 1988), the VP22 protein of HSV (Elliott and O'Hare, 1997) and fibroblast growth factor (Lin et al., 1995).

Cell-penetrating peptides (or "protein transduction domains") have been identified from the third helix of the *Drosophila* Antennapedia homeobox gene (Antp), the HIV Tat, and the herpes virus VP22, all of which contain positively charged domains enriched for arginine and lysine residues (Schwarze et al., 2000; Schwarze et al., 1999). Also, hydrophobic peptides derived from signal sequences have been identified as cell-penetrating peptides. (Rojas et al., 1996; Rojas et al., 1998; Du et al., 1998). Coupling these peptides to marker proteins such as β-galactosidase has been shown to confer efficient internalization of the marker protein into cells, and chimeric, in-frame fusion proteins containing these peptides have been used to deliver proteins to a wide spectrum of cell types both in vitro and in vivo (Drin et al., 2002). Fusion of these cell penetrating peptides to a tumor antigen-specific peptide (e.g., a VCX/Y peptide) in accordance with the present disclosure may enhance cellular uptake of the polypeptides.

In some embodiments, cellular uptake is facilitated by the attachment of a lipid, such as stearate or myristilate, to the polypeptide. Lipidation has been shown to enhance the passage of peptides into cells. The attachment of a lipid moiety is another way that the present disclosure increases polypeptide uptake by the cell. Cellular uptake is further discussed below.

A tumor antigen-specific peptide (e.g., a VCX/Y peptide) of the present disclosure may be included in a liposomal vaccine composition. For example, the liposomal composition may be or comprise a proteoliposomal composition. Methods for producing proteoliposomal compositions that may be used with the present disclosure are described, e.g., in Neelapu et al. (2007) and Popescu et al. (2007). In some embodiments, proteoliposomal compositions may be used to treat a melanoma.

By enhancing the uptake of a tumor antigen-specific polypeptide, it may be possible to reduce the amount of protein or peptide required for treatment. This in turn can significantly reduce the cost of treatment and increase the supply of therapeutic agent. Lower dosages can also minimize the potential immunogencity of peptides and limit toxic side effects.

In some embodiments, a tumor antigen-specific peptide (e.g., a VCX/Y peptide) may be associated with a nanoparticle to form nanoparticle-polypeptide complex. In some embodiments, the nanoparticle is a liposomes or other lipid-based nanoparticle such as a lipid-based vesicle (e.g., a DOTAP:cholesterol vesicle). In other embodiments, the nanoparticle is an iron-oxide based superparamagnetic nanoparticles. Superparamagnetic nanoparticles ranging in diameter from about 10 to 100 nm are small enough to avoid sequestering by the spleen, but large enough to avoid clearance by the liver. Particles this size can penetrate very small capillaries and can be effectively distributed in body tissues. Superparamagnetic nanoparticles-polypeptide complexes can be used as MRI contrast agents to identify and follow those cells that take up the tumor antigen-specific peptide (e.g., a VCX/Y peptide). In some embodiments, the nanoparticle is a semiconductor nanocrystal or a semiconductor quantum dot, both of which can be used in optical imaging. In further embodiments, the nanoparticle can be a nanoshell, which comprises a gold layer over a core of silica. One advantage of nanoshells is that polypeptides can be conjugated to the gold layer using standard chemistry. In other embodiments, the nanoparticle can be a fullerene or a nanotube (Gupta et al., 2005).

Peptides are rapidly removed from the circulation by the kidney and are sensitive to degradation by proteases in serum. By associating a tumor antigen-specific peptide (e.g., a VCX/Y peptide) with a nanoparticle, the nanoparticle-polypeptide complexes of the present disclosure may protect against degradation and/or reduce clearance by the kidney. This may increase the serum half-life of polypeptides, thereby reducing the polypeptide dose need for effective therapy. Further, this may decrease the costs of treatment, and minimizes immunological problems and toxic reactions of therapy.

B. Polyepitope Strings

In some embodiments, a tumor antigen-specific peptide (e.g., a VCX/Y peptide) is included or comprised in a polyepitope string. A polyepitope string is a peptide or polypeptide containing a plurality of antigenic epitopes from one or more antigens linked together. A polyepitope string may be used to induce an immune response in a subject, such as a human subject. Polyepitope strings have been previously used to target malaria and other pathogens (Baraldo et al., 2005; Moorthy et al., 2004; Baird et al., 2004). A polyepitope string may refer to a nucleic acid (e.g., a nucleic acid encoding a plurality of antigens including a VCX/Y peptide) or a peptide or polypeptide (e.g., containing a plurality of antigens including a VCX/Y peptide). A polyepitope string may be included in a cancer vaccine composition.

C. Biological Functional Equivalents

A tumor antigen-specific peptide (e.g., a VCX/Y peptide) of the present disclosure may be modified to contain amino acid substitutions, insertions and/or deletions that do not alter their respective interactions with an HLA class protein, such as HLA-A*0101, binding regions. Such a biologically functional equivalent of a tumor antigen-specific peptide (e.g., a VCX/Y peptide) could be a molecule having like or otherwise desirable characteristics, e.g., binding of HLA-A*0201. As a nonlimiting example, certain amino acids may be substituted for other amino acids in a tumor antigen-specific peptide (e.g., a VCX/Y peptide) disclosed herein without appreciable loss of interactive capacity, as demonstrated by detectably unchanged peptide binding to HLA-A*0201. In some embodiments, the tumor antigen-specific peptide has a substitution mutation at an anchor reside, such as a substitution mutation at one, two, or all of positions: 1 (P1), 2 (P2), and/or 9 (P9). It is thus contemplated that a tumor antigen-specific peptide (e.g., a VCX/Y peptide) disclosed herein (or a nucleic acid encoding such a peptide) which is modified in sequence and/or structure, but which is unchanged in biological utility or activity remains within the scope of the compositions and methods disclosed herein.

It is also well understood by the skilled artisan that, inherent in the definition of a biologically functional equivalent peptide, is the concept that there is a limit to the number of changes that may be made within a defined portion of the molecule while still maintaining an acceptable level of equivalent biological activity. Biologically functional equivalent peptides are thus defined herein as those peptides in which certain, not most or all, of the amino acids may be substituted. Of course, a plurality of distinct peptides with different substitutions may easily be made and used in accordance with the present disclosure.

The skilled artisan is also aware that where certain residues are shown to be particularly important to the biological or structural properties of a peptide, e.g., residues in specific epitopes, such residues may not generally be exchanged. This may be the case in the present disclosure, as a mutation in an tumor antigen-specific peptide (e.g., the VCX/Y peptide) disclosed herein could result in a loss of species-specificity and in turn, reduce the utility of the resulting peptide for use in methods of the present disclosure. Thus, peptides which are antigenic (e.g., bind HLA-A*0201 specifically) and comprise conservative amino acid substitutions are understood to be included in the present disclosure. Conservative substitutions are least likely to drastically alter the activity of a protein. A "conservative amino acid substitution" refers to replacement of amino acid with a chemically similar amino acid, i.e., replacing nonpolar amino acids with other nonpolar amino acids; substitution of polar amino acids with other polar amino acids, acidic residues with other acidic amino acids, etc.

Amino acid substitutions, such as those which might be employed in modifying a tumor antigen-specific peptide (e.g., a VCX/Y peptide) disclosed herein are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents. In some embodiments, the mutation may enhance TCR-pMHC interaction and/or peptide-MHC binding.

The present disclosure also contemplates isoforms of the tumor antigen-specific peptides (e.g., a VCX/Y peptide) disclosed herein. An isoform contains the same number and kinds of amino acids as a peptide of the present disclosure, but the isoform has a different molecular structure. The isoforms contemplated by the present disclosure are those having the same properties as a peptide of the present disclosure as described herein.

Nonstandard amino acids may be incorporated into proteins by chemical modification of existing amino acids or by de novo synthesis of a peptide disclosed herein. A nonstandard amino acid refers to an amino acid that differs in chemical structure from the twenty standard amino acids encoded by the genetic code.

In select embodiments, the present disclosure contemplates a chemical derivative of a tumor antigen-specific peptide (e.g., a VCX/Y peptide) disclosed herein. "Chemical derivative" refers to a peptide having one or more residues chemically derivatized by reaction of a functional side group, and retaining biological activity and utility. Such derivatized peptides include, for example, those in which free amino groups have been derivatized to form specific salts or derivatized by alkylation and/or acylation, p-toluene sulfonyl groups, carbobenzoxy groups, t-butylocycarbonyl groups, chloroacetyl groups, formyl or acetyl groups among others. Free carboxyl groups may be derivatized to form organic or inorganic salts, methyl and ethyl esters or other types of esters or hydrazides and preferably amides (primary or secondary). Chemical derivatives may include those peptides which comprise one or more naturally occurring amino acids derivatives of the twenty standard amino acids. For example, 4-hydroxyproline may be substituted for serine; and ornithine may be substituted for lysine.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The amino acids described herein are preferred to be in the "L" isomeric form. However, residues in the "D" isomeric form can be substituted for any L-amino acid residue, as long as the desired functional properties set forth herein are retained by the protein.

Preferred tumor antigen-specific peptides (e.g., a VCX/Y peptide) or analogs thereof preferably specifically or preferentially bind a HLA-A*0201. Determining whether or to what degree a particular tumor antigen-specific peptide or labeled peptide, or an analog thereof, can bind an HLA-A*0201 and can be assessed using an in vitro assay such as, for example, an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (FA), nephelometry, flow cytometry assay, chemiluminescence assay, lateral flow immunoassay, u-capture assay, mass spectrometry assay, particle-based assay, inhibition assay and/or an avidity assay.

D. Nucleic Acids Encoding a Tumor Antigen-Specific Peptide

In an aspect, the present disclosure provides a nucleic acid encoding an isolated antigen-specific peptide comprising a sequence that has at least about 90%, 91%, 92%, 93%, 94%, 95%, 96%, 97%, 98%, 99%, or 100% sequence identity SEQ ID NO:1, 8, 9, 12, 13, or 14, or the peptide may have 1, 2, 3, or 4 point mutations (e.g., substitution mutations) as compared to SEQ ID NO:1, 8, 9, 12, 13, or 14. As stated above, such a tumor antigen-specific peptide may be, e.g., from 8 to 35 amino acids in length, or any range derivable therein. In some embodiments, the tumor antigen-specific peptide corresponds to a portion of the tumor antigen protein such as VCX1, VCX2, VCX3A, VCX3B, or VCY (e.g., VCX3A; GenBank Accession No: AAI26903.1). The term "nucleic acid" is intended to include DNA and RNA and can be either double stranded or single stranded.

Some embodiments of the present disclosure provide recombinantly-produced tumor antigen-specific peptides (e.g., a VCX/Y peptide) which can specifically bind a HLA-A*0201. Accordingly, a nucleic acid encoding a tumor antigen-specific peptide may be operably linked to an expression vector and the peptide produced in the appropriate expression system using methods well known in the molecular biological arts. A nucleic acid encoding a tumor antigen-specific peptide disclosed herein may be incorporated into any expression vector which ensures good expression of the peptide. Possible expression vectors include but are not limited to cosmids, plasmids, or modified viruses (e.g. replication defective retroviruses, adenoviruses and adeno-associated viruses), so long as the vector is suitable for transformation of a host cell.

A recombinant expression vector being "suitable for transformation of a host cell" means that the expression vector contains a nucleic acid molecule of the present disclosure and regulatory sequences selected on the basis of the host cells to be used for expression, which is operatively linked to the nucleic acid molecule. The terms, "operatively linked" or "operably linked" are used interchangeably, and are intended to mean that the nucleic acid is linked to regulatory sequences in a manner which allows expression of the nucleic acid.

Accordingly, the present disclosure provides a recombinant expression vector comprising nucleic acid encoding a tumor antigen-specific peptide, and the necessary regulatory sequences for the transcription and translation of the inserted protein-sequence. Suitable regulatory sequences may be derived from a variety of sources, including bacterial, fungal, or viral genes (e.g., see the regulatory sequences described in Goeddel (1990).

Selection of appropriate regulatory sequences is generally dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

A recombinant expression vector may also contain a selectable marker gene which facilitates the selection of host cells transformed or transfected with a recombinant tumor antigen-specific peptides (e.g., a VCX/Y peptide) disclosed herein. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of a recombinant expression vector, and in particular, to determine the effect of a mutation on expression and phenotype. It will be appreciated that selectable markers can be introduced on a separate vector from the nucleic acid of interest.

Recombinant expression vectors can be introduced into host cells to produce a transformant host cell. The term "transformant host cell" is intended to include prokaryotic and eukaryotic cells which have been transformed or transfected with a recombinant expression vector of the present disclosure. The terms "transformed with", "transfected with", "transformation" and "transfection" are intended to encompass introduction of nucleic acid (e.g. a vector) into a cell by one of many possible techniques known in the art. Suitable host cells include a wide variety of prokaryotic and eukaryotic host cells. For example, the proteins of the present disclosure may be expressed in bacterial cells such as E. coli, insect cells (using baculovirus), yeast cells or mammalian cells.

A nucleic acid molecule of the present disclosure may also be chemically synthesized using standard techniques. Various methods of chemically synthesizing polydeoxynucleotides are known, including solid-phase synthesis which, like peptide synthesis, has been fully automated in commercially available DNA synthesizers (See e.g., U.S. Pat. Nos. 4,598,049; 4,458,066; 4,401,796; and 4,373,071).

III. Antigen-Specific Cell Therapy

Embodiments of the present disclosure concern obtaining and administering antigen-specific cells (e.g., autologous or allogeneic T cells (e.g., regulatory T cells, CD4+ T cells, CD8+ T cells, or gamma-delta T cells), NK cells, invariant NK cells, NKT cells, mesenchymal stem cell (MSC)s, or induced pluripotent stem (iPS) cells) to a subject as an immunotherapy to target cancer cells. In particular, the cells are antigen-specific T cells (e.g., VCX/Y-specific T cells). Several basic approaches for the derivation, activation and expansion of functional anti-tumor effector cells have been described in the last two decades. These include: autologous cells, such as tumor-infiltrating lymphocytes (TILs); T cells activated ex-vivo using autologous DCs, lymphocytes, artificial antigen-presenting cells (APCs) or beads coated with T cell ligands and activating antibodies, or cells isolated by virtue of capturing target cell membrane; allogeneic cells naturally expressing anti-host tumor T cell receptor (TCR); and non-tumor-specific autologous or allogeneic cells genetically reprogrammed or "redirected" to express tumor-reactive TCR or chimeric TCR molecules displaying antibody-like tumor recognition capacity known as "T-bodies". These approaches have given rise to numerous protocols for T cell preparation and immunization which can be used in the methods described herein.

A. T Cell Preparation

In some embodiments, the T cells are derived from the blood, bone marrow, lymph, umbilical cord, or lymphoid organs. In some aspects, the cells are human cells. The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells (e.g., CD4+ and/or CD8+ T cells) are naive T ($T_N$) cells, effector T cells ($T_{EFF}$), memory T cells and sub-types thereof, such as stem cell memory T ($TSC_M$), central memory T ($TC_M$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, one or more of the T cell populations is enriched for or depleted of cells that are positive for a specific marker, such as surface markers, or that are negative for a specific marker. In some cases, such markers are those that are absent or expressed at relatively low levels on certain populations of T cells (e.g., non-memory cells) but are present or expressed at relatively higher levels on certain other populations of T cells (e.g., memory cells).

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations.

In some embodiments, CD8+ T cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al., 2012; Wang et al., 2012.

In some embodiments, the T cells are autologous T cells. In this method, tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Single-cell suspensions of tumor enzymatic digests are cultured in interleukin-2 (IL-2). The cells are cultured until confluence (e.g., about 2×10$^6$ lymphocytes), e.g., from about 5 to about 21 days, preferably from about 10 to about 14 days.

The cultured T cells can be pooled and rapidly expanded. Rapid expansion provides an increase in the number of antigen-specific T-cells of at least about 50-fold (e.g., 50-, 60-, 70-, 80-, 90-, or 100-fold, or greater) over a period of about 10 to about 14 days. More preferably, rapid expansion provides an increase of at least about 200-fold (e.g., 200-, 300-, 400-, 500-, 600-, 700-, 800-, 900-, or greater) over a period of about 10 to about 14 days.

Expansion can be accomplished by any of a number of methods as are known in the art. For example, T cells can be rapidly expanded using non-specific T cell receptor stimulation in the presence of feeder lymphocytes and either interleukin-2 (IL-2) or interleukin-15 (IL-15), with IL-2 being preferred. The non-specific T cell receptor stimulus can include around 30 ng/ml of OKT3, a mouse monoclonal anti-CD3 antibody (available from Ortho-McNeil®, Raritan, N.J.). Alternatively, T cells can be rapidly expanded by stimulation of PBMCs in vitro with one or more antigens (including antigenic portions thereof, such as epitope(s), or a cell) of the cancer, which can be optionally expressed from a vector, such as an human leukocyte antigen A2 (HLA-A2) binding peptide, in the presence of a T cell growth factor, such as 300 IU/ml IL-2 or IL-15, with IL-2 being preferred. The in vitro-induced T cells are rapidly expanded by re-stimulation with the same antigen(s) of the cancer pulsed onto HLA-A2-expressing antigen-presenting cells. Alternatively, the T cells can be re-stimulated with irradiated, autologous lymphocytes or with irradiated HLA-A2+ allogeneic lymphocytes and IL-2, for example.

The autologous T cells can be modified to express a T cell growth factor that promotes the growth and activation of the autologous T cells. Suitable T cell growth factors include, for example, IL-2, IL-7, IL-15, and IL-12. Suitable methods of modification are known in the art. See, for instance, Sambrook et al., 2001; and Ausubel et al., 1994. In particular aspects, modified autologous T cells express the T cell growth factor at high levels. T cell growth factor coding sequences, such as that of IL-12, are readily available in the art, as are promoters, the operable linkage of which to a T cell growth factor coding sequence promote high-level expression.

B. Genetically Engineered Antigen Receptors

The cells (e.g., autologous or allogeneic T cells (e.g., regulatory T cells, CD4+ T cells, CD8+ T cells, or gamma-delta T cells), NK cells, invariant NK cells, NKT cells, mesenchymal stem cell (MSCs), or induced pluripotent stem cells) of the present disclosure can be genetically engineered to express antigen receptors such as engineered TCRs and/or CARs. For example, the host cell (e.g, autologous or allogeneic T-cells) are modified to express a TCR having antigenic specificity for a cancer antigen. In particular embodiments, the antigen receptors have antigenic specificity for VCX/Y, such as VCX1, VCX2, VCX3A, VCX3B, and VCY, particularly the VCX54 peptide. In certain embodiments, the engineered TCR has an alpha chain CDR3 with at least 90, 91, 92, 93, 94, 95, 96, 97, 98, 99, or 100% sequence identity to SEQ ID NO:2 or 19 and/or a beta chain CDR3 with at least 90, 91, 92, 93, 94, 95, 96, 97, 98, 99, or 100% sequence identity to SEQ ID NO:3 or 20. In some embodiments, the TCR has an alpha chain with at least 90, 91, 92, 93, 94, 95, 96, 97, 98, 99, or 100% sequence identity to SEQ ID NO:4, 5, 15, or 16 and/or a beta chain with at least 90, 91, 92, 93, 94, 95, 96, 97, 98, 99, or 100% sequence identity to SEQ ID NO:6, 7, 17, or 18. Suitable methods of modification are known in the art. See, for instance, Sambrook and Ausubel, supra. For example, the cells may be transduced to express a TCR having antigenic specificity for a cancer antigen using transduction techniques described in Heemskerk et al., 2008 and Johnson et al., 2009.

In some embodiments, the cells comprise one or more nucleic acids introduced via genetic engineering that encode one or more antigen receptors, and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature (e.g., chimeric).

In some embodiments, the CAR contains an extracellular antigen-recognition domain that specifically binds to an antigen. In some embodiments, the antigen is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary antigen receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., 2013; Davila et al., 2013; Turtle et al., 2012; Wu et al., 2012. In some aspects, the genetically engineered antigen receptors include a CAR as described in U.S. Pat. No. 7,446,190, and those described in International Patent Application Publication No.: WO/2014055668 A1.

1. Chimeric Antigen Receptors

In some embodiments, the engineered antigen receptors include CARs, including activating or stimulatory CARs, costimulatory CARs (see WO2014/055668), and/or inhibitory CARs (iCARs, see Fedorov et al., 2013). The CARs generally include an extracellular antigen (or ligand) binding domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone.

In some embodiments, CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody.

In some aspects, the antigen-specific binding, or recognition component is linked to one or more transmembrane and intracellular signaling domains. In some embodiments, the CAR includes a transmembrane domain fused to the extracellular domain of the CAR. In one embodiment, the transmembrane domain that naturally is associated with one of the domains in the CAR is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 zeta, CD3 epsilon, CD3 gamma, CD3 delta, CD45, CD4, CD5, CD8, CD9, CD 16, CD22, CD33, CD37, CD64, CD80, CD86, CD 134, CD137, CD154, ICOS/CD278, GITR/CD357, NKG2D, and DAP molecules. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

The CAR generally includes at least one intracellular signaling component or components. In some embodiments, the CAR includes an intracellular component of the TCR complex, such as a TCR CD3$^+$ chain that mediates T-cell activation and cytotoxicity, e.g., CD3 zeta chain. Thus, in some aspects, the antigen binding molecule is linked to one or more cell signaling modules. In some embodiments, cell signaling modules include CD3 transmembrane domain, CD3 intracellular signaling domains, and/or other CD transmembrane domains. In some embodiments, the CAR further includes a portion of one or more additional molecules such as Fc receptor γ, CD8, CD4, CD25, or CD16. For example, in some aspects, the CAR includes a chimeric molecule between CD3-zeta (CD3-Q or Fc receptor γ and CD8, CD4, CD25 or CD16.

2. T Cell Receptor (TCR)

In some embodiments, the genetically engineered antigen receptors include recombinant TCRs and/or TCRs cloned from naturally occurring T cells. A "T cell receptor" or "TCR" refers to a molecule that contains a variable a and β chains (also known as TCRα and TCRβ, respectively) or a variable γ and δ chains (also known as TCRγ and TCRδ, respectively) and that is capable of specifically binding to an antigen peptide bound to a MHC receptor. In some embodiments, the TCR is in the αβ form. In certain embodiments, the engineered TCR has an alpha chain CDR3 of SEQ ID NO:2 and/or a beta chain CDR3 of SEQ ID NO:3. In some embodiments, the TCR has an alpha chain of SEQ ID NO:4, 5, 15, or 16 and/or a beta chain of SEQ ID NO:6, 7, 17, or 18.

Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules. In some embodiments, a TCR also can contain a constant domain, a transmembrane domain and/or a short cytoplasmic tail (see, e.g., Janeway et al, 1997). For example, in some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction. Unless otherwise stated, the term "TCR" should be understood to encompass functional TCR fragments thereof. The term also encompasses intact or full-length TCRs, including TCRs in the αβ form or γδ form.

Thus, for purposes herein, reference to a TCR includes any TCR or functional fragment, such as an antigen-binding portion of a TCR that binds to a specific antigenic peptide bound in an MHC molecule, i.e. MHC-peptide complex. An "antigen-binding portion" or antigen-binding fragment" of a TCR, which can be used interchangeably, refers to a molecule that contains a portion of the structural domains of a TCR, but that binds the antigen (e.g. MHC-peptide complex) to which the full TCR binds. In some cases, an antigen-binding portion contains the variable domains of a TCR, such as variable a chain and variable 13 chain of a TCR, sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule and determine peptide specificity. Typically, like immunoglobulins, the CDRs are separated by framework regions (FRs) (see, e.g., Jores et al. 1990; Chothia et al., 1988; Lefranc et al., 2003). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains contain a constant domain. For example, like immunoglobulins, the extracellular portion of TCR chains (e.g., a-chain, β-chain) can contain two immunoglobulin domains, a variable domain (e.g., $V_a$ or Vp; typically amino acids 1 to 116 based on Kabat numbering Kabat et al., "Sequences of Proteins of Immunological Interest, US Dept. Health and Human Services, Public Health Service National Institutes of Health, 1991, $5^{th}$ ed.) at the N-terminus, and one constant domain (e.g., a-chain constant domain or $C_a$, typically amino acids 117 to 259 based on Kabat, β-chain constant domain or Cp, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domain of the TCR domain contains short connecting sequences in which a cysteine residue forms a disulfide bond, making a link between the two chains. In some embodiments, a TCR may have an additional cysteine residue in each of the α and β chains such that the TCR contains two disulfide bonds in the constant domains.

In some embodiments, the TCR chains can contain a transmembrane domain. In some embodiments, the transmembrane domain is positively charged. In some cases, the TCR chains contains a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

Generally, CD3 is a multi-protein complex that can possess three distinct chains (γ, δ, and ε) in mammals and the ζ-chain. For example, in mammals the complex can contain a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Generally, ITAMs are involved in the signaling capacity of the TCR complex. These accessory molecules have negatively charged transmembrane regions and play a role in propagating the signal from the TCR into the cell. The CD3- and ζ-chains, together with the TCR, form what is known as the T cell receptor complex.

In some embodiments, the TCR may be a heterodimer of two chains a and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds. In some embodiments, a TCR for a target antigen (e.g., a cancer antigen) is identified and introduced into the cells. In some embodiments, nucleic acid encoding the TCR can be obtained from a variety of sources, such as by polymerase chain reaction (PCR) amplification of publicly available TCR DNA sequences. In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, a high-affinity T cell clone can be isolated from a patient, and the TCR isolated. In some embodiments, the T-cells can be a cultured T-cell hybridoma or clone. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al., 2009 and Cohen et al., 2005). In some embodiments, phage display is used to isolate TCRs against a target antigen (see, e.g., Varela-Rohena et al., 2008 and Li, 2005). In some embodiments, the TCR or antigen-binding portion thereof can be synthetically generated from knowledge of the sequence of the TCR.

3. Antigen-Presenting Cells

Antigen-presenting cells, which include macrophages, B lymphocytes, and dendritic cells, are distinguished by their expression of a particular MHC molecule. APCs internalize antigen and re-express a part of that antigen, together with the MHC molecule on their outer cell membrane. The major histocompatibility complex (MHC) is a large genetic complex with multiple loci. The MHC loci encode two major classes of MHC membrane molecules, referred to as class I and class II MHCs. T helper lymphocytes generally recognize antigen associated with MHC class II molecules, and T cytotoxic lymphocytes recognize antigen associated with MHC class I molecules. In humans the MHC is referred to as the HLA complex and in mice the H-2 complex.

In some cases, aAPCs are useful in preparing therapeutic compositions and cell therapy products of the embodiments. For general guidance regarding the preparation and use of antigen-presenting systems, see, e.g., U.S. Pat. Nos. 6,225, 042, 6,355,479, 6,362,001 and 6,790,662; U.S. Patent Application Publication Nos. 2009/0017000 and 2009/0004142; and International Publication No. WO2007/103009.

aAPC systems may comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD86, CD64 (FcγRI), 41BB ligand, and IL-21. Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), which promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001.

IV. Soluble TCRs

In some embodiments, the present disclosure provides soluble TCRs, such as a VCX/Y TCR provided herein. Soluble TCRs are useful, not only for the purpose of investigating specific TCR-pMHC interactions, but also potentially as a diagnostic tool to detect infection, or to detect autoimmune disease markers. Soluble TCRs also have applications in staining, for example to stain cells for the presence of a particular peptide antigen presented in the context of the MHC. Similarly, soluble TCRs can be used to deliver a therapeutic agent, for example a cytotoxic compound or an immunostimulating compound, to cells presenting a particular antigen. Soluble TCRs may also be used to inhibit T cells, for example, those reacting to an auto-immune peptide antigen. In some aspects, the TCR is linked to another molecule that delivers a cell in proximity to the tumor. In further aspects, the TCR delivers a toxin, a cytokine, costimulatory ligand, or inhibitor ligand and directs the molecule, cell or compound to the target cells expressing the peptide-MHC.

In the context of this application, "solubility" is defined as the ability of the TCR to be purified as a mono disperse heterodimer in phosphate buffered saline (PBS) (KCL 2.7 mM, $KH_2PO_4$ 1.5 mM, NaCl 137 mM and $Na_2PO4$ 8 mM, pH 7.1-7.5. Life Technologies, Gibco BRL) at a concentration of 1 mg/ml and for more than 90% of said TCR to remain as a mono disperse heterodimer after incubation at 25° C. for 1 hour.

In some aspects, the present disclosure provides a soluble T cell receptor (sTCR), which comprises (i) all or part of a TCR α chain (e.g., SEQ ID NO:4, 5, 15, or 16), except the transmembrane domain thereof, and (ii) all or part of a TCR β chain (e.g., SEQ ID NO:6, 7, 17, or 18), except the transmembrane domain thereof, wherein (i) and (ii) each comprise a functional variable domain and at least a part of the constant domain of the TCR chain, and are linked by a disulphide bond between constant domain residues which is not present in native TCR.

In some aspects, the soluble TCR comprises a TCR α or γ chain extracellular domain dimerized to a TCR β or δ chain extracellular domain respectively, by means of a pair of C-terminal dimerization peptides, such as leucine zippers (International Patent Publication No. WO 99/60120; U.S. Pat. No. 7,666,604).

A soluble TCR (which is preferably human) of the present disclosure may be provided in substantially pure form, or as a purified or isolated preparation. For example, it may be provided in a form which is substantially free of other proteins.

A plurality of soluble TCRs of the present disclosure may be provided in a multivalent complex. Thus, the present disclosure provides, in one aspect, a multivalent T cell receptor (TCR) complex, which comprises a plurality of soluble T cell receptors as described herein. Each of the plurality of soluble TCRs is preferably identical.

In its simplest form, a multivalent TCR complex according to the present disclosure comprises a multimer of two or three or four or more T cell receptor molecules associated (e.g. covalently or otherwise linked) with one another, preferably via a linker molecule. Suitable linker molecules include, but are not limited to, multivalent attachment molecules such as avidin, streptavidin, neutravidin and extravidin, each of which has four binding sites for biotin. Thus, biotinylated TCR molecules can be formed into multimers of T cell receptors having a plurality of TCR binding sites. The number of TCR molecules in the multimer will depend upon the quantity of TCR in relation to the quantity of linker molecule used to make the multimers, and also on the presence or absence of any other biotinylated molecules. Preferred multimers are dimeric, trimeric or tetrameric TCR complexes.

Suitable structures for use in the present methods include membrane structures such as liposomes and solid structures which are preferably particles such as beads, for example latex beads. Other structures which may be externally coated with T cell receptor molecules are also suitable. Preferably, the structures are coated with T cell receptor multimers rather than with individual T cell receptor molecules.

In the case of liposomes, the T cell receptor molecules or multimers thereof may be attached to or otherwise associated with the membrane. Techniques for this are well known to those skilled in the art.

A label or another moiety, such as a toxic or therapeutic moiety, may be included in a multivalent TCR complex of the present disclosure. For example, the label or other moiety may be included in a mixed molecule multimer. An example of such a multimeric molecule is a tetramer containing three TCR molecules and one peroxidase molecule. This could be achieved by mixing the TCR and the enzyme at a molar ratio of 3:1 to generate tetrameric complexes, and isolating the desired complex from any complexes not containing the correct ratio of molecules. These mixed molecules could contain any combination of molecules, provided that steric hindrance does not compromise or does not significantly compromise the desired function of the molecules. The positioning of the binding sites on the streptavidin molecule is suitable for mixed tetramers since steric hindrance is not likely to occur.

The TCR (or multivalent complex thereof) of the present disclosure may alternatively or additionally be associated with (e.g. covalently or otherwise linked to) a therapeutic agent which may be, for example, a toxic moiety for use in cell killing, or an immunostimulating agent such as an interleukin or a cytokine. A multivalent TCR complex of the present disclosure may have enhanced binding capability for a TCR ligand compared to a non-multimeric T cell receptor heterodimer. Thus, the multivalent TCR complexes according to the present disclosure are particularly useful for tracking or targeting cells presenting particular antigens in vitro or in vivo, and are also useful as intermediates for the production of further multivalent TCR complexes having such uses. The TCR or multivalent TCR complex may therefore be provided in a pharmaceutically acceptable formulation for use in vivo.

The present disclosure also provides a method for delivering a therapeutic agent to a target cell, which method comprises contacting potential target cells with a TCR or multivalent TCR complex in accordance with the present disclosure under conditions to allow attachment of the TCR or multivalent TCR complex to the target cell, said TCR or multivalent TCR complex being specific for the TCR ligand and having the therapeutic agent associated therewith.

In particular, the soluble TCR or multivalent TCR complex can be used to deliver therapeutic agents to the location of cells presenting a particular antigen. This would be useful in many situations and, in particular, against tumors. A therapeutic agent could be delivered such that it would exercise its effect locally but not only on the cell it binds to. Thus, one particular strategy envisages anti-tumor molecules linked to T cell receptors or multivalent TCR complexes specific for tumor antigens.

Many therapeutic agents could be employed for this use, for instance radioactive compounds, enzymes (perforin for example) or chemotherapeutic agents (cisplatin for example). To ensure that toxic effects are exercised in the desired location the toxin could be inside a liposome linked to streptavidin so that the compound is released slowly. This will prevent damaging effects during the transport in the body and ensure that the toxin has maximum effect after binding of the TCR to the relevant antigen presenting cells.

Other suitable therapeutic agents include:
  small molecule cytotoxic agents, i.e. compounds with the ability to kill mammalian cells having a molecular weight of less than 700 daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolmide, topotecan, trimetreate glucuronate, auristatin E vincristine and doxorubicin;
  peptide cytotoxins, i.e. proteins or fragments thereof with the ability to kill mammalian cells. Examples include ricin, diphtheria toxin, *pseudomonas* bacterial exotoxin A, DNAase and RNAase;
  radio-nuclides, i.e. unstable isotopes of elements which decay with the concurrent emission of one or more of a or 13 particles, or γ rays. Examples include iodine 131, rhenium 186, indium 111, yttrium 90, bismuth 210 and 213, actinium 225 and astatine 213;
  prodrugs, such as antibody directed enzyme pro-drugs; and
  immuno-stimulants, i.e. moieties which stimulate immune response. Examples include cytokines such as IL-2, chemokines such as IL-8, platelet factor 4, melanoma growth stimulatory protein, etc., antibodies or fragments thereof such as anti-CD3 antibodies or fragments thereof, complement activators, xenogeneic protein domains, allogeneic protein domains, viral/bacterial protein domains and viral/bacterial peptides.

The soluble TCRs of the present disclosure may be used to modulate T cell activation by binding to specific TCR ligand and thereby inhibiting T cell activation. Autoimmune diseases involving T cell-mediated inflammation and/or tissue damage would be amenable to this approach, for example type I diabetes. Knowledge of the specific peptide epitope presented by the relevant pMHC is required for this use.

The use of the soluble TCRs and/or multivalent TCR complexes of the present disclosure in the preparation of a composition for the treatment of cancer or autoimmune disease is also envisaged.

Also provided is a method of treatment of cancer or autoimmune disease comprising administration to a patient in need thereof of an effective amount of the soluble TCRs and/or multivalent TCR complexes of the present disclosure.

As is common in anti-cancer and autoimmune therapy the sTCRs of the present disclosure may be used in combination with other agents for the treatment of cancer and autoimmune disease, and other related conditions found in similar patient groups.

V. Methods of Treatment

Provided herein are methods for treating or delaying progression of cancer in an individual comprising administering to the individual an effective amount an antigen-specific cell therapy, such as a VCX/Y-specific T cell therapy. Adoptive T cell therapies with genetically engineered TCR-transduced T cells (conjugate TCR to other bioreactive proteins (e.g., anti-CD3) are also provided herein. In further embodiments, methods are provided for the treatment of cancer comprising immunizing a subject with a purified tumor antigen or an immunodominant tumor antigen-specific peptide.

The VCX/Y peptide provided herein can be utilized to develop cancer vaccines or immunogens (e.g., a peptide or modified peptide mix with adjuvant, coding polynucleotide and corresponding expression products such as inactive virus or other microorganisms vaccine). These peptide specific vaccines or immunogens can be used for immunizing cancer patients directly to induce anti-tumor immuno-response in vivo, or for expanding antigen specific T cells in vitro with peptide or coded polynucleotide loaded APC stimulation. These large number of T cells can be adoptively transferred to patients to induce tumor regression.

Examples of cancers contemplated for treatment include lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, and bladder cancer.

In some embodiments, T cells are autologous. However the cells can be allogeneic. In some embodiments, the T cells are isolated from the patient themself, so that the cells are autologous. If the T cells are allogeneic, the T cells can be pooled from several donors. The cells are administered to the subject of interest in an amount sufficient to control, reduce, or eliminate symptoms and signs of the disease being treated.

In some embodiments, the subject can be administered nonmyeloablative lymphodepleting chemotherapy prior to the T cell therapy. The nonmyeloablative lymphodepleting chemotherapy can be any suitable such therapy, which can be administered by any suitable route. The nonmyeloablative lymphodepleting chemotherapy can comprise, for example, the administration of cyclophosphamide and fludarabine, particularly if the cancer is melanoma, which can be metastatic. An exemplary route of administering cyclophosphamide and fludarabine is intravenously. Likewise, any suitable dose of cyclophosphamide and fludarabine can be administered. In particular aspects, around 60 mg/kg of cyclophosphamide is administered for two days after which around 25 mg/m$^2$ fludarabine is administered for five days.

In certain embodiments, a T-cell growth factor that promotes the growth and activation of the autologous T cells is administered to the subject either concomitantly with the autologous T cells or subsequently to the autologous T cells. The T-cell growth factor can be any suitable growth factor that promotes the growth and activation of the autologous T-cells. Examples of suitable T-cell growth factors include IL-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2. IL-12 is a preferred T-cell growth factor.

The T cell may be administered intravenously, intramuscularly, subcutaneously, topically, orally, transdermally, intraperitoneally, intraorbitally, by implantation, by inhalation, intrathecally, intraventricularly, or intranasally. The appropriate dosage of the T cell therapy may be determined based on the type of disease to be treated, severity and course of the disease, the clinical condition of the individual, the individual's clinical history and response to the treatment, and the discretion of the attending physician.

Intratumoral injection, or injection into the tumor vasculature is specifically contemplated for discrete, solid, accessible tumors. Local, regional or systemic administration also may be appropriate. For tumors of >4 cm, the volume to be administered will be about 4-10 ml (in particular 10 ml), while for tumors of <4 cm, a volume of about 1-3 ml will be used (in particular 3 ml). Multiple injections delivered as single dose comprise about 0.1 to about 0.5 ml volumes.

A. Pharmaceutical Compositions

Also provided herein are pharmaceutical compositions and formulations comprising antigen-specific immune cells (e.g., T cells) or receptors (e.g., TCR) and a pharmaceutically acceptable carrier. A vaccine composition for pharmaceutical use in a subject may comprise a tumor antigen peptide (e.g., VCX/Y) composition disclosed herein and a pharmaceutically acceptable carrier.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 22$^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutralactive hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

B. Combination Therapies

In certain embodiments, the compositions and methods of the present embodiments involve an antigen-specific immune cell population or TCR in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

An immune cell therapy may be administered before, during, after, or in various combinations relative to an additional cancer therapy, such as immune checkpoint therapy. The administrations may be in intervals ranging from concurrently to minutes to days to weeks. In embodiments where the immune cell therapy is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below an antigen-specific immune cell therapy, peptide, or TCR is "A" and an anti-cancer therapy is

A/B/A B/A/B B/B/A A/A/B A/B/B B/A/A A/B/B/B B/A/B/B

B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammall and calicheamicin omegall); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine,plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCE-TRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAGS), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, *Nat Rev Cancer*, 12(4): 252-64, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Application No. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al. (1998) *Proc Natl Acad Sci USA* 95(17): 10067-10071; Camacho et al. (2004) *J Clin Oncology* 22(145): Abstract No. 2505 (antibody CP-675206); and Mokyr et al. (1998) *Cancer Res* 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

VI. Articles of Manufacture or Kits

An article of manufacture or a kit is provided comprising antigen-specific immune cells, TCRs, or antigen peptides (e.g., VCX/Y peptide) is also provided herein. The article of manufacture or kit can further comprise a package insert comprising instructions for using the antigen-specific immune cells to treat or delay progression of cancer in an individual or to enhance immune function of an individual having cancer. Any of the antigen-specific immune cells described herein may be included in the article of manufacture or kits. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Identification and Characterization of Tumor Antigen-Specific Peptides Epitope prediction tools including BIMAS, SYFPEITHI and NetMHC analysis were used to predict HLA-restricted peptide epitopes for the VCX3A antigen. The results of the VCX3A binding and affinity prediction are depicted in Table 1.

TABLE 1

HLA-A*0201 peptide of VCX3A binding and affinity prediction.

| Peptide | BIMAS score | SYFPEITHI score | NetMHC affinity prediction |
|---|---|---|---|
| KVAKKGKAV (37) (SEQ ID NO: 8) | 21.3 | 18 | 10442.93 nM |
| GAATKMAAV (54) (SEQ ID NO: 1) | 2.22 | 21 | 3260.85 nM |
| SEMEELPSV (178) (SEQ ID NO: 9) | 47.187 | 22 | 495.92 nM |

Figure 1B:
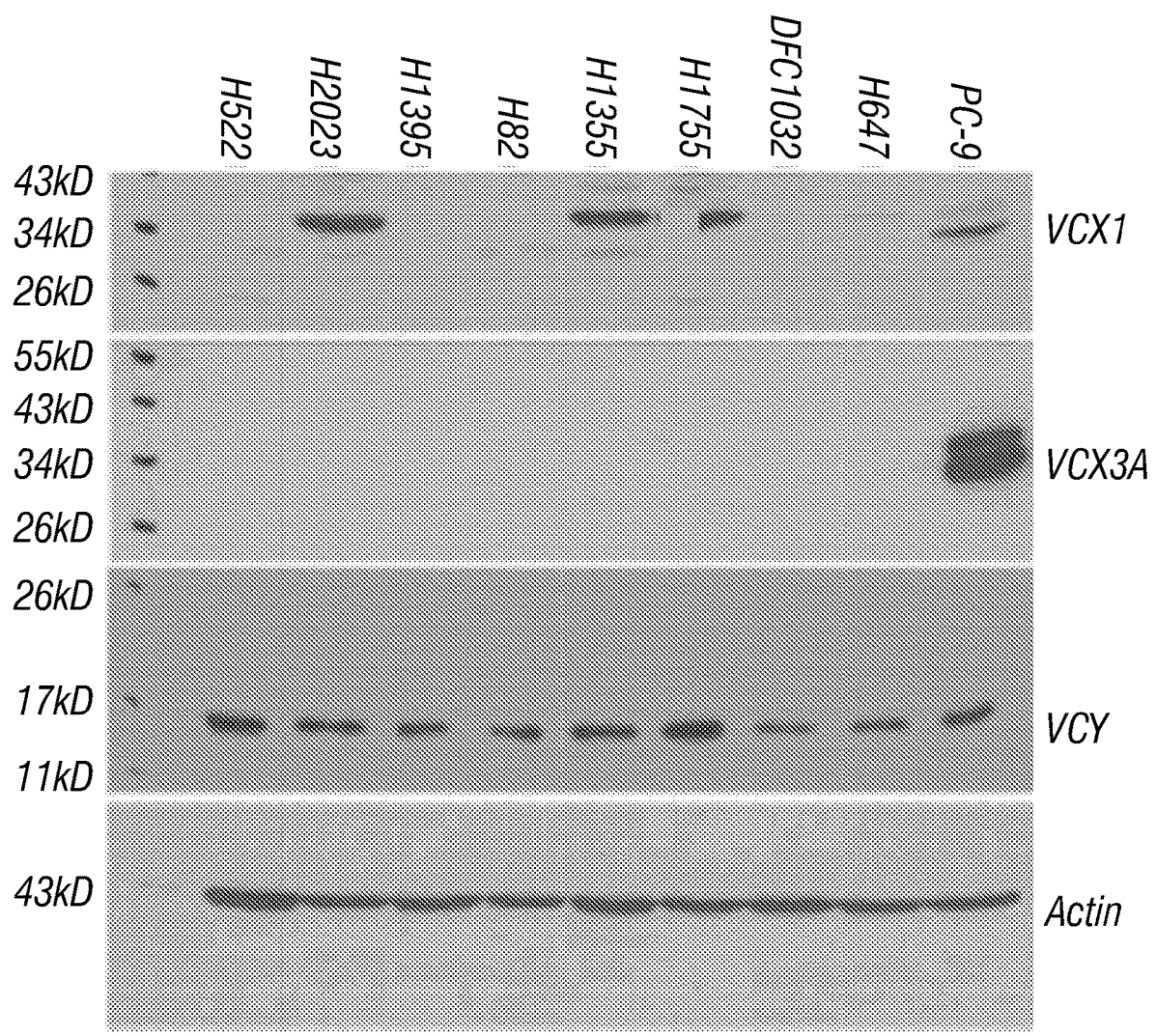

The predicted peptides were synthesized and co-cultured with T2 cells with a series of diluted concentrations. DMSO without peptide or with the same concentration of negative binding to HLA-A2 peptide were used as control. After 18 hr incubation, the HLA-A2 expression was detected by flow cytometer. The fluorescence index (FI) was calculated as follows: FI=(mean fluorescence with the given peptide−mean fluorescence without peptide)/(mean fluorescence without peptide). From the binding assay, it was found that the VCX54 peptide showed the strongest binding to the HLA-A2 allele among the 3 predicted peptides (FIG. 1A). The VCX54 epitope is found in all members of the VCX/Y family including VCX1, VCX2, VCX3A, VCX3B, or VCY which are expressed in various lung cancer cells (FIG. 1B).

Figures 2A, 2B:
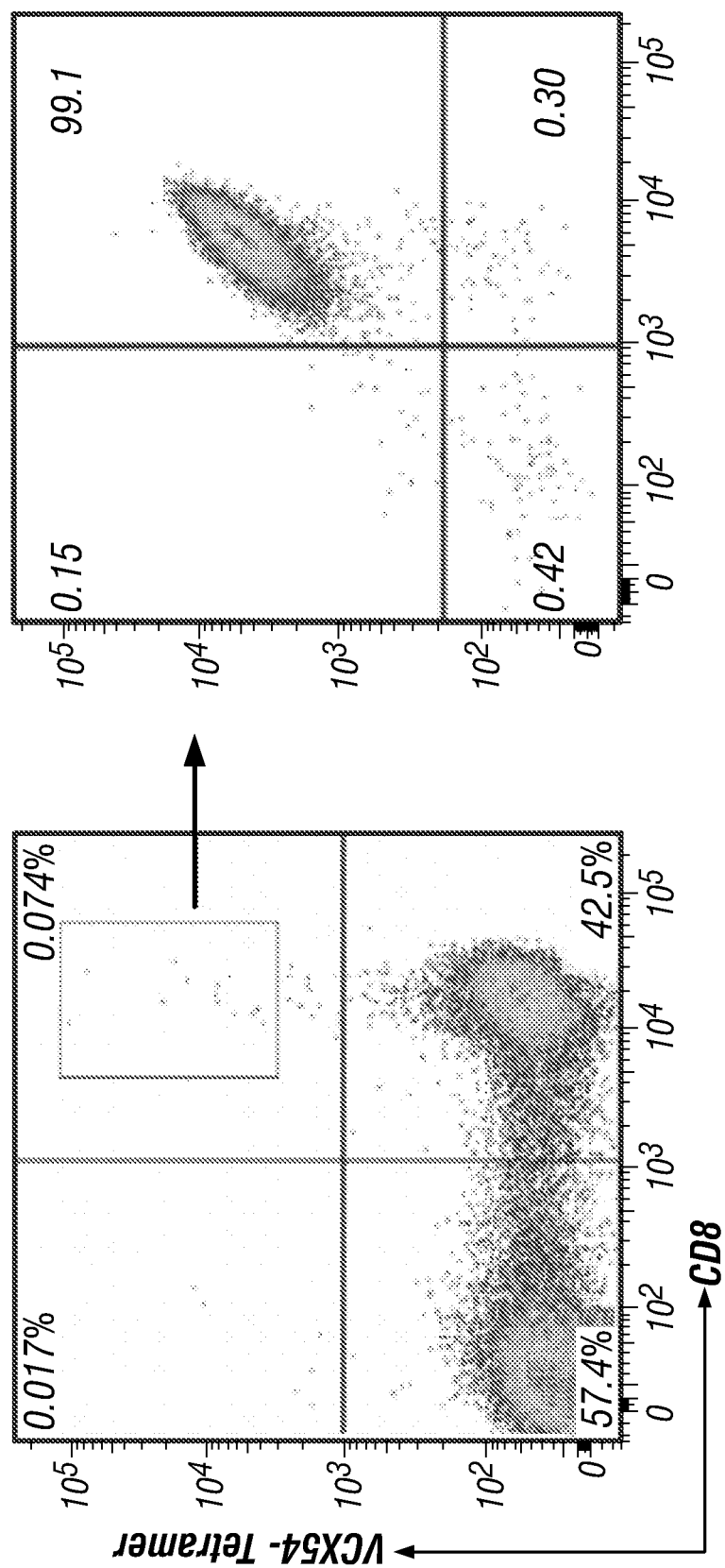
FIGS. 2A-2B: Production of VCX54 specific T cell clone from HLA-A*0201 healthy donor. (A) CD8 and VCX54 tetramer expression of T cells after two stimulation with VCX3A antigen pulsed dendritic cells. (B) CD8 and VCX54 tetramer expression of T cells after expansion using the rapid expansion protocol (REP).

Next, VCX54 specific T cell clones were produced from an HLA-A*0201 healthy donor. After 2 stimulations using VCX3A mRNA pulsed dendritic cells, CD8$^+$ and VCX54 tetramer$^+$ T cell populations were observed (FIG. 2A). After tetramer guided sorting, the cells were expanded using rapid expansion protocol (REP). T cells clones were generated with the limiting dilution method and they underwent 2 expansions. Over 99% of the cells were observed to be CD8$^+$ and tetramer$^+$ (FIG. 2B).

Figure 3A:
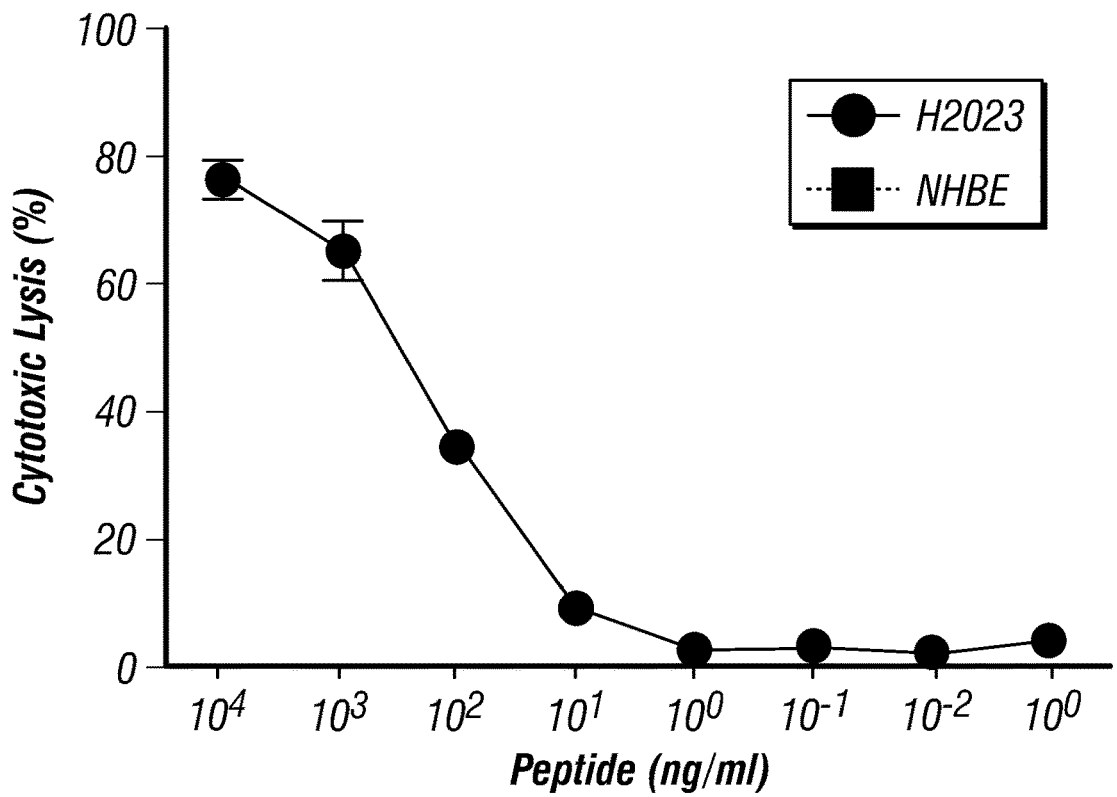
FIGS. 3A-3B: Functional avidity of VCX54 specific T cells. (A) Cytotoxicity lysis of the VCX54 CTL clone co-cultured with T2 cells pulsed with various concentrations of VCX54 peptide at an effector to target (E:T) ratio of 20:1. (B) Cytotoxicity lysis of the VCX54 CTL clone (C7) co-cultured with VCX1 positive expression human lung cancer cell line H2023 (HLA-A0201+) or primary bronchial epithelial cells NHBE (HLA-A0201+) at various E:T ratios.
Figure 3B:
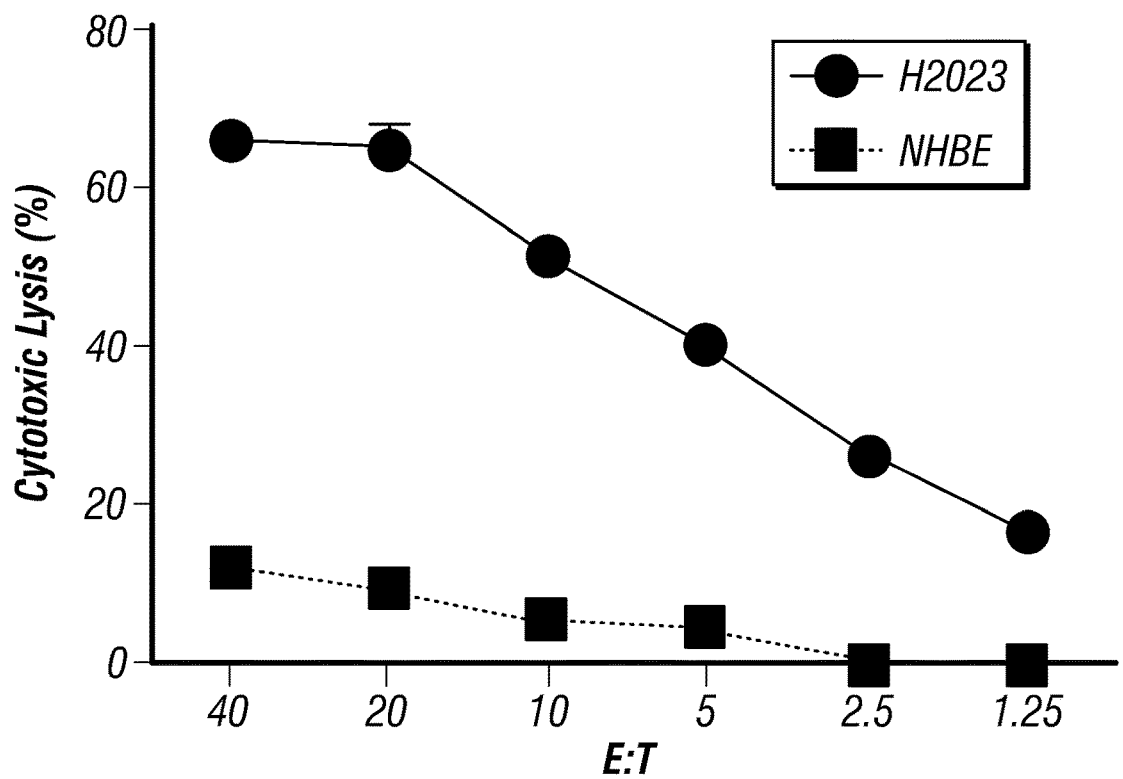

Functional avidity of the VCX54 specific T cells was tested. The VCX54 CTL clone was co-cultured with T2 cells pulsed with various concentrations of VCX54 peptide at an effector to target (E:T) ratio of 20:1. The cytotoxicity lysis was detected with the standard $_{51}$Cr release assay (CRA) (FIG. 3). The VCX54 CTL clone (C7) was co-cultured with VCX1 positive expression human lung cancer cell line H2023 (HLA-A*0201±) or primary bronchial epithelial cells NHBE (HLA-A*0201±) at various E:T ratios. The cytotoxicity lysis was detected with the standard $_{51}$Cr release assay (CRA).

Figure 4:
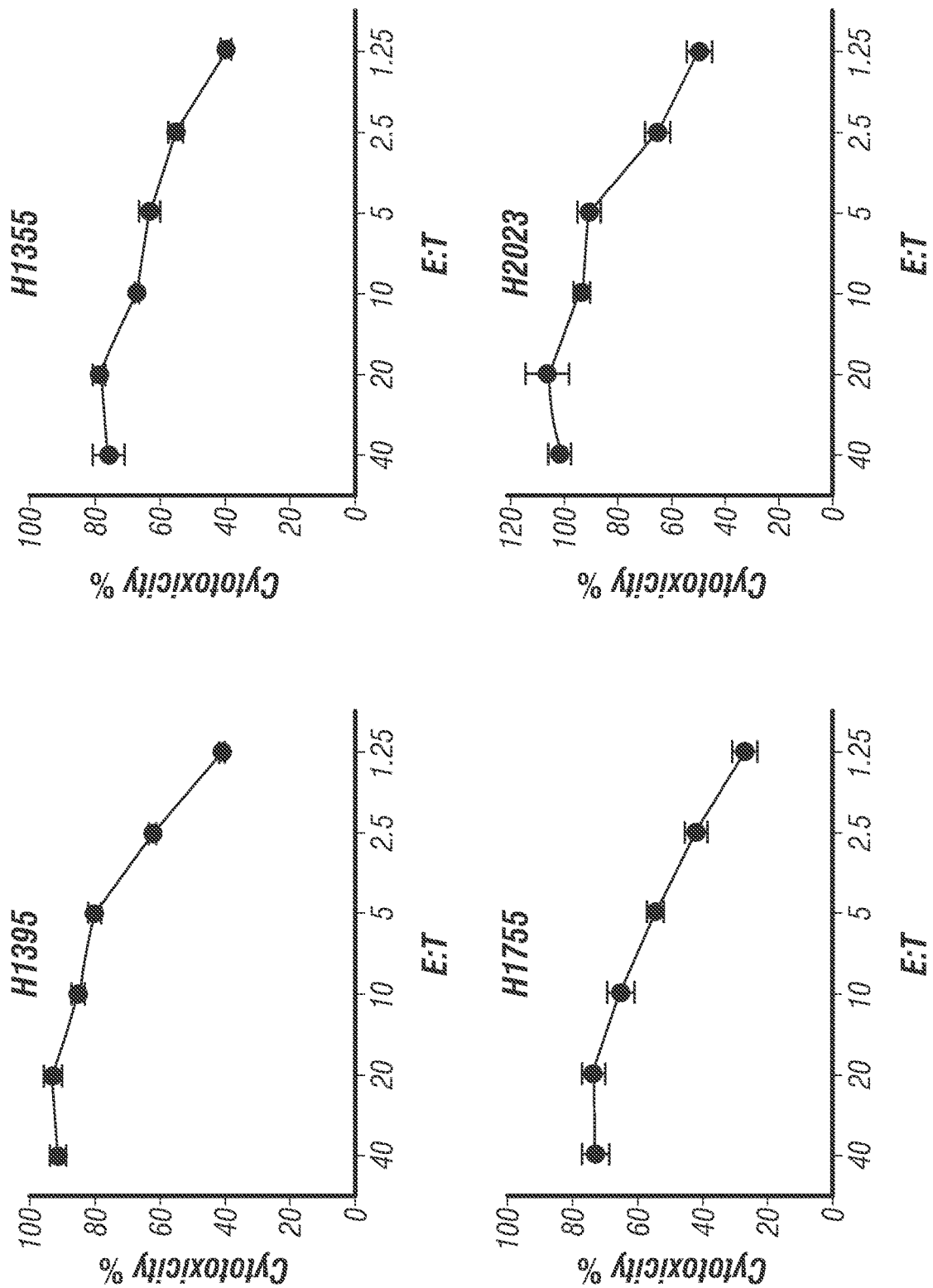
FIG. 4: Recognition of endogenous presented VCX54 peptide of specific T cells. Cytotoxicity lysis of VCX54 CTL clone co-cultured with a panel of HLA-A2+ lung cancer cell line which expressed VCX3A or VCX1 at various E:T ratios.
Figure 4:
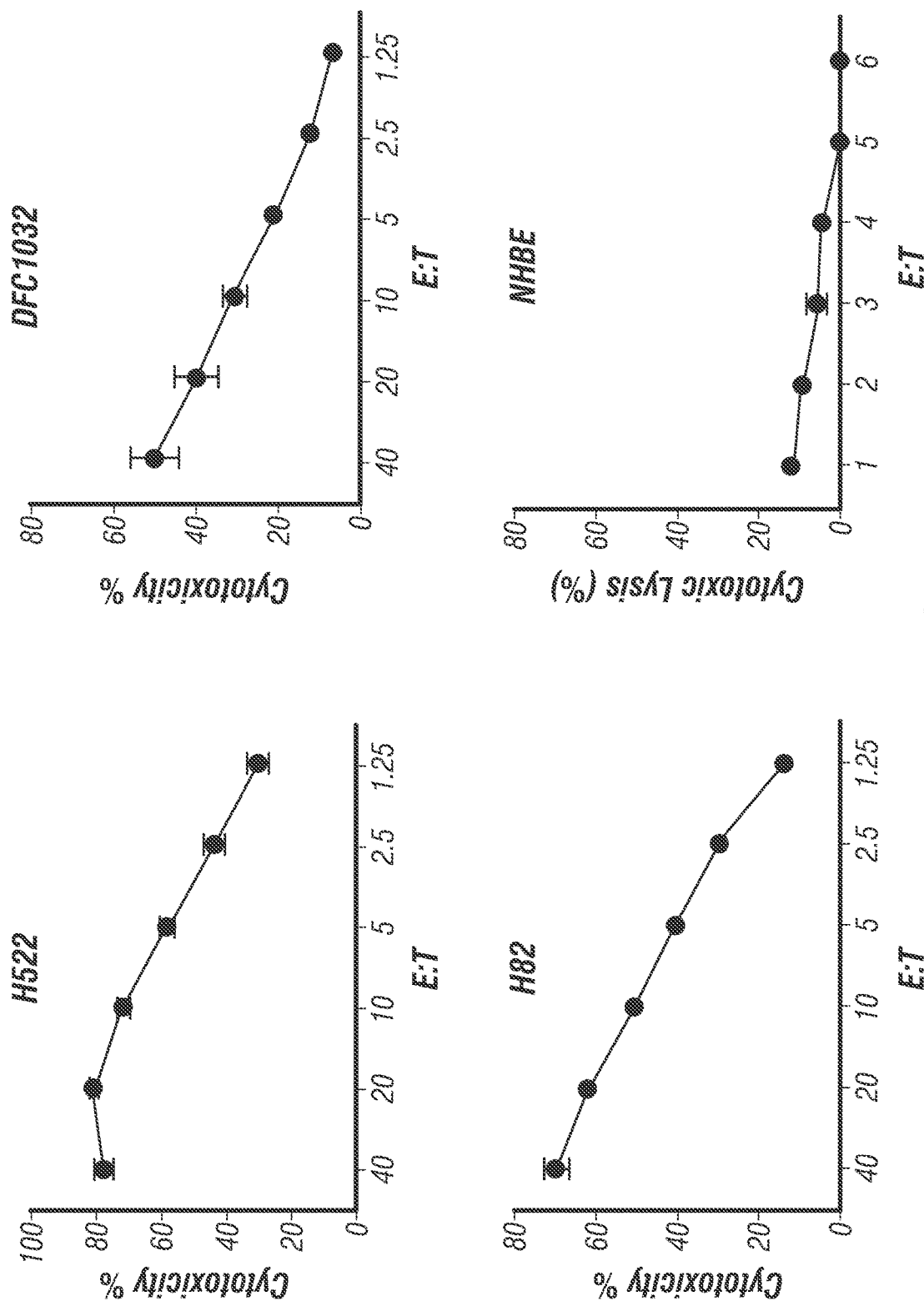

In order to determine the recognition of endogenous presented VCX54 peptide by specific T cells, a panel of HLA-A2 positive lung cancer cell lines were tested. The VCX54 CTL clone was co-cultured with the panel of HLA-A2+ lung cancer cell lines which expressed VCY, VCX3A or VCX1 at various E:T ratios. HLA-A2 positive primary bronchial epithelial NHBE cells were used for the detection of cytotoxicity of the CTL clone on normal lung tissue. The specific cytotoxicity lysis was detected with the standard 51Cr release assay (CRA). A high level of cytotoxicity of VCX54 CTL clone was observed in lung cancer cells but not in the primary bronchial epithelial NHBE cells (FIG. 4). Thus, the VCX54 CTL clone was selectively cytotoxic to cancer cells which express the VCX antigen.

Figure 5:
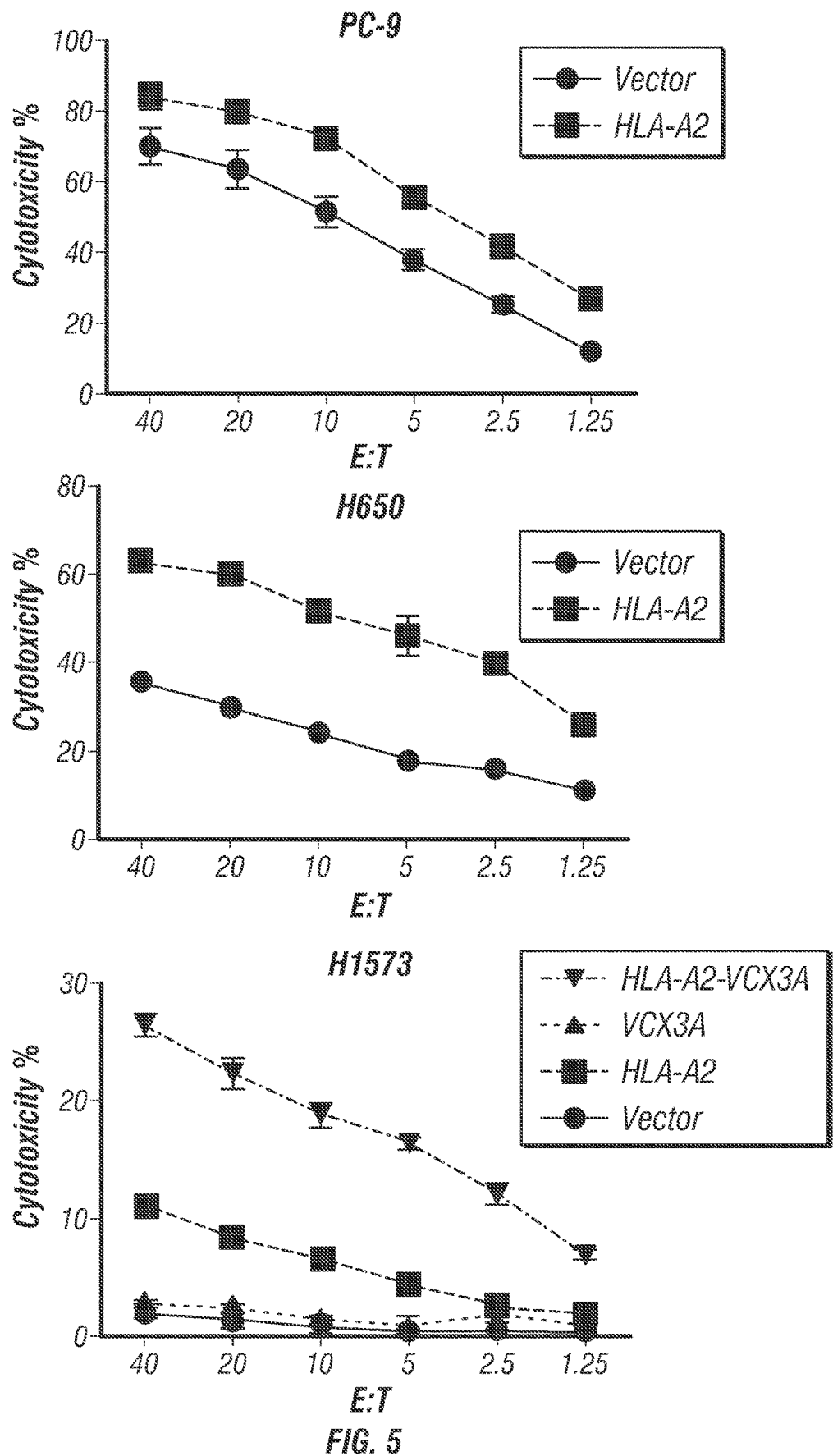
FIG. 5: HLA allele restriction analysis of VCX specific T cells. Cytotoxicity of several VCX54 CTL clones on HLA-A0201 negative lung cancer cell lines.

Next, an HLA allele restriction analysis of the VCX/Y specific T cells was performed. Several HLA-A0201 negative lung cancer cell lines were analyzed using the CRA assay to detect the HLA restriction of VCX54 CTL clone. The PC-9 cell line is HLA-A0206/A2402 positive, and the H650 cell line is HLA-A2402 positive. Forced expression of the HLA-A0201 allele gene in these two cell lines significantly enhanced the cytotoxicity lysis level of the CTL clone (FIG. 5). H1573 is an HLA-A0201 and HLA-A2402 negative cell line. Forced expression of HLA-A0201 allele gene enhanced the cytotoxicity lysis but not at a high level. Co-transfection of the HLA-A0201 allele and the VCX3A gene was found to significantly enhance the cytotoxicity lysis level of the CTL clone.

Figure 6:
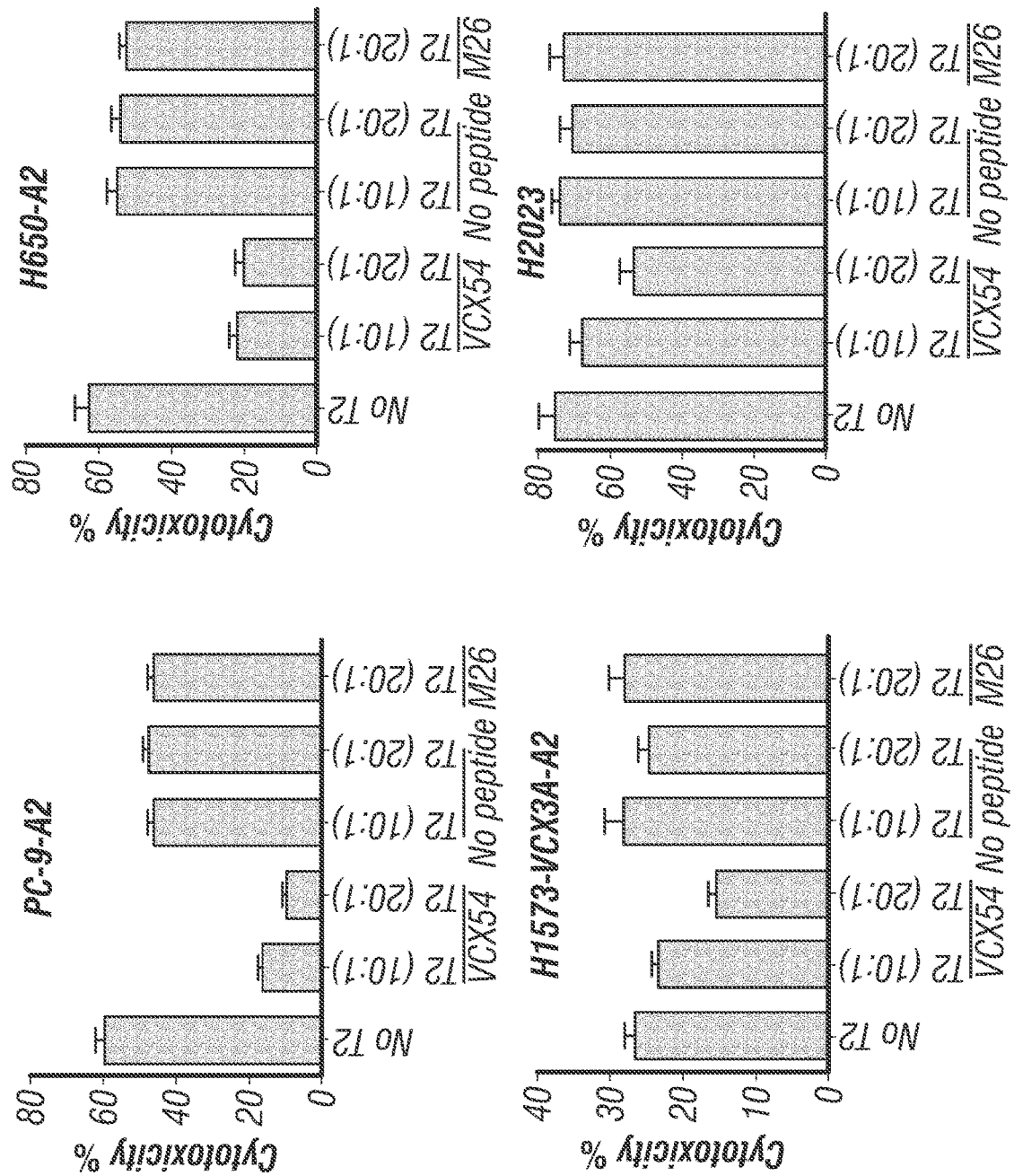
FIG. 6: Specific cytotoxicity confirmation of VCX specific T cells to lung cancer cells. Endogenously presented peptide specific recognition of VCX54 CTL clone detected with cold target inhibition assay.
Figure 6:
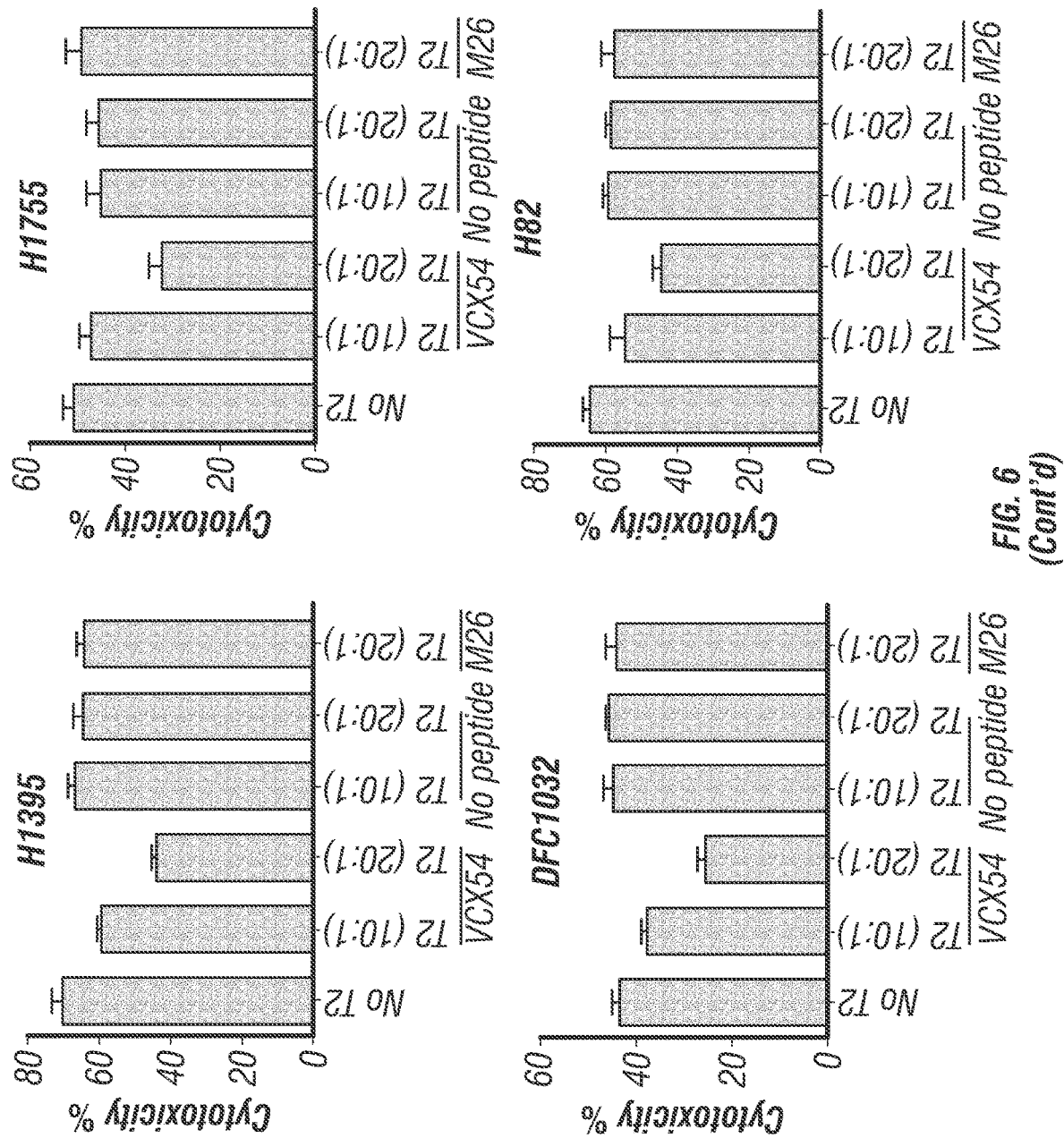

In addition, the specific cytotoxicity of the VCX specific T cells to lung cancer cells was confirmed. Endogenously presented peptide specific recognition of VCX54 CTL clone was detected with the cold target inhibition assay. The hot targets were the lung cancer cells (HLA-A2 positive or forced expression). The cold targets were the T2 cells pulsed with VCX54 peptide (10 µg/ml). The T2 cells without any peptide or pulsed with M26 peptide (10 µg/ml) were used as the negative control. The E:T ratio was 10:1. The Cold target:Hot target ratio was 10:1 or 20:1. Significant inhibition was observed when T2 cells were pulsed with VCX54 peptide at the Cold target: Hot target ratio of 20:1 (FIG. 6).

Example 2—Generation and Evaluation of VCX54 Specific T Cell Receptor

Figure 7A:
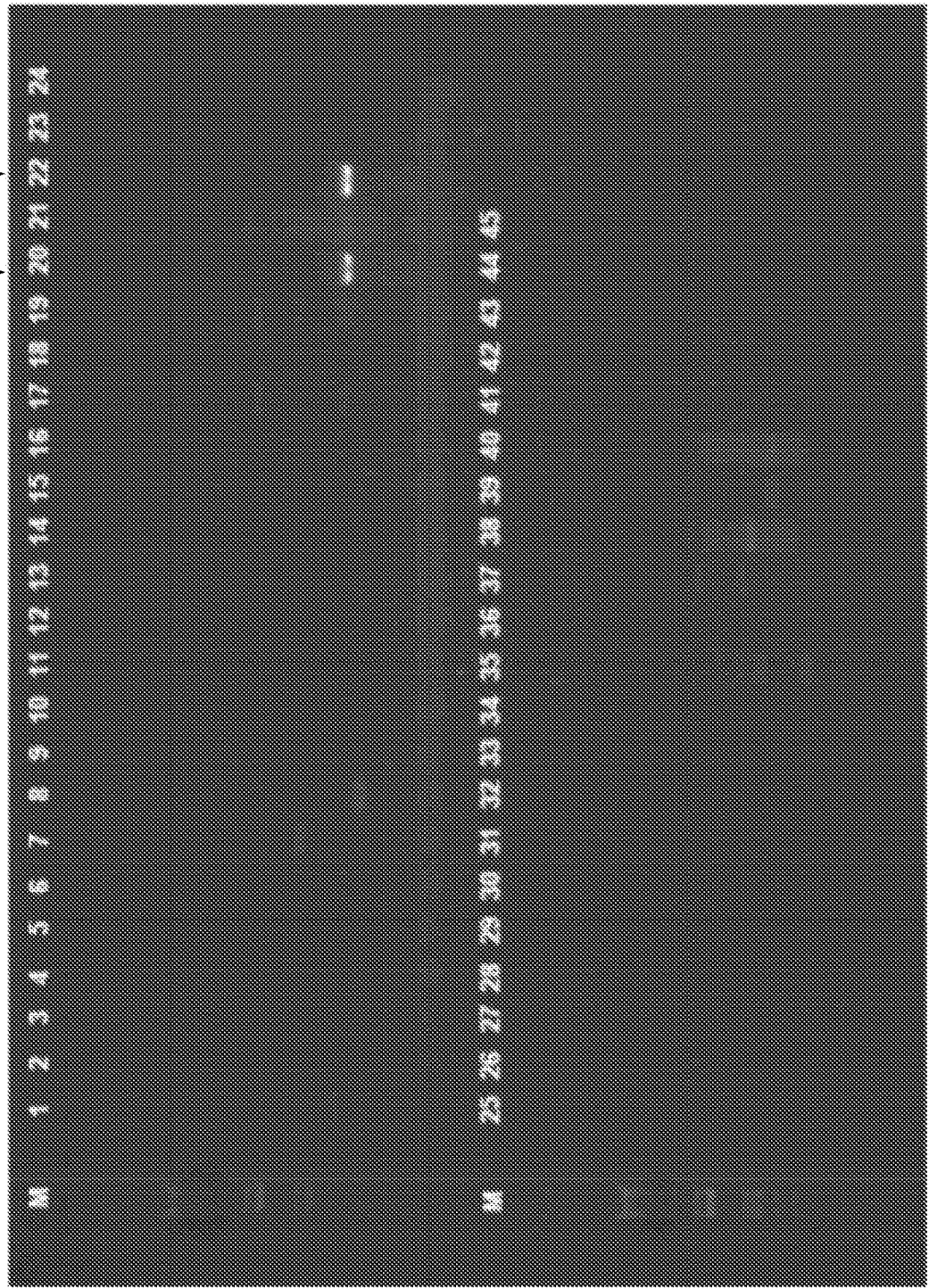
FIGS. 7A-7B: VCX54 CTL clone (C7) TCR usage analysis. (A) TCR alpha chain (TRAV) usage PCR identification. The TRAV usage is TRAV-13.1 or TRAV-14. (B) TCR beta chain (TRBV) usage flow cytometer detection. The TRBV usage is TRBV-13.
Figure 7B:
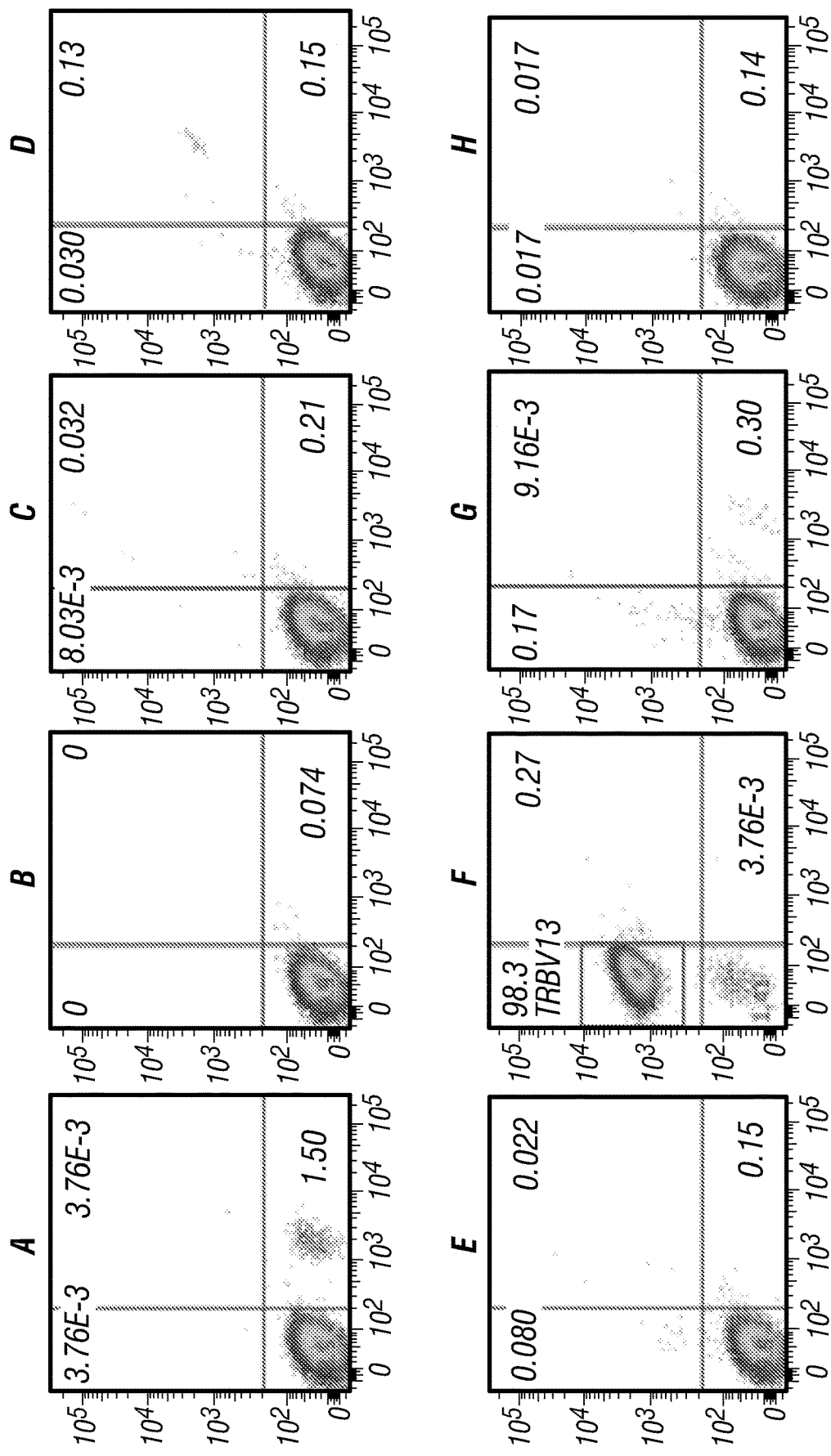

The T cell receptor of the VCX54 clone C7 of Example 1 was subjected to usage and sequence analysis. Using PCR identification and flow cytometry, the TCR alpha chain (TRAY) TRAV-14 and TCR beta chain (TRBV) TRBV-13 were analyzed (FIG. 7). The TRAV-14 CDR3 amino acid sequence was determined to be CAMITSGNTGKLIF (SEQ ID NO:2) and the TRBV-13 CDR3 amino acid sequence was determined to be CASSPPGGGRTEAFF (SEQ ID NO:3) (FIG. 8).

Figure 9:
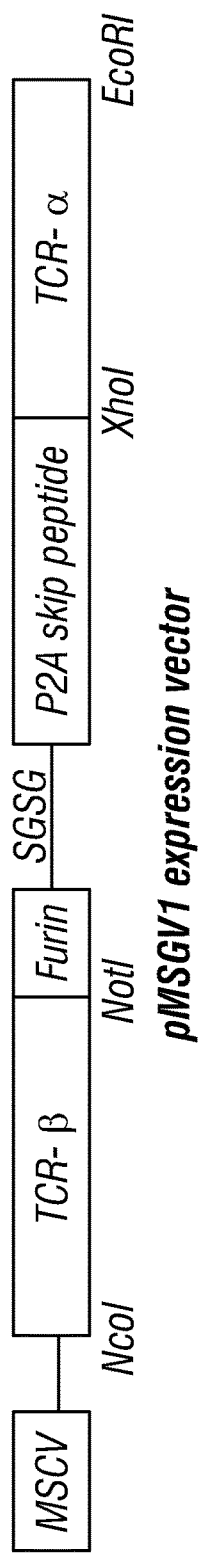
FIG. 9: The TCR from VCX54 CTL clone was constructed into the retrovirus expression vector pMSGV1. A linker fragment contain Furin cleavage site, SGSG linker and P2A cleavage site was inserted between the TCR-β chain and TCR-α chain to guarantee both chains were expressed at equal levels under the MSCV promoter.
Figure 10:
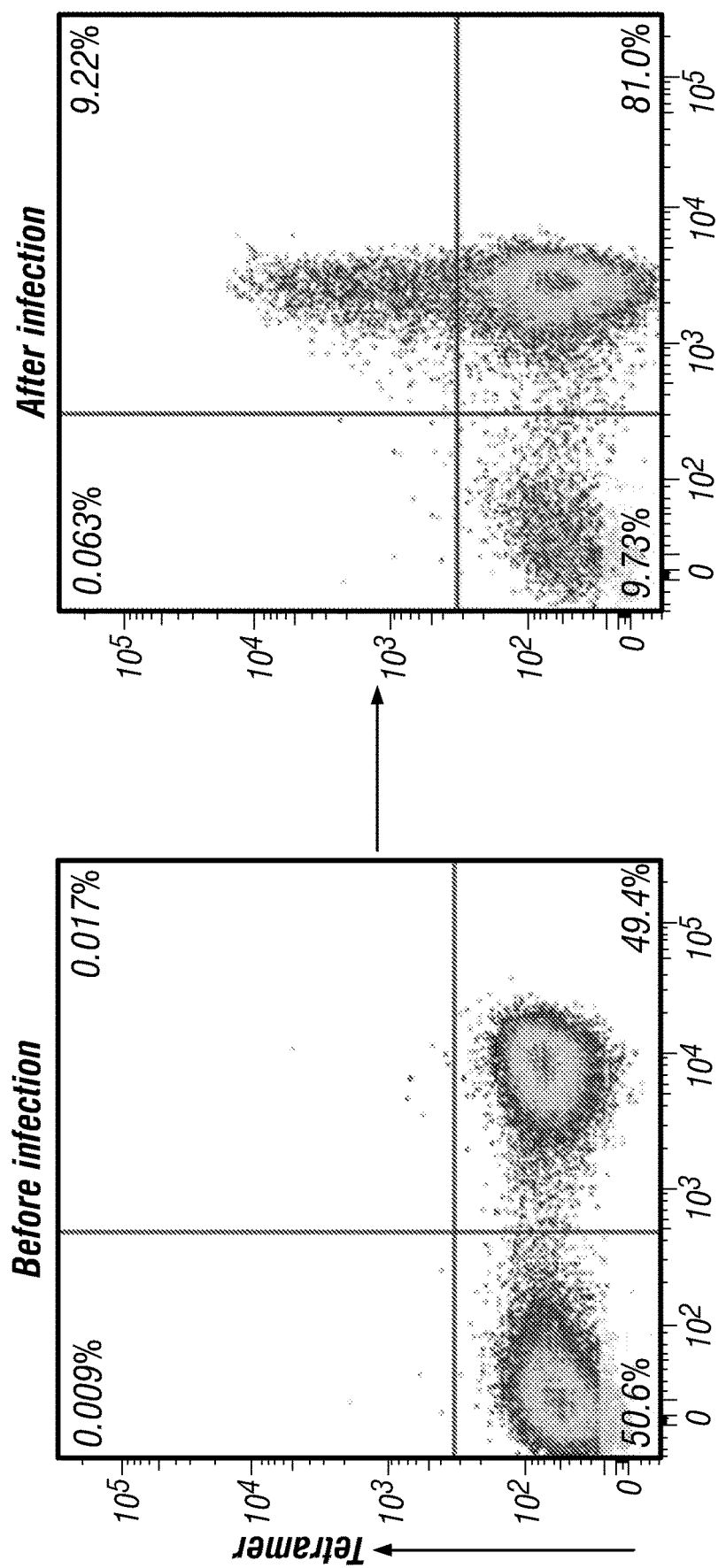
FIG. 10: The retrovirus expression vector pMSGV1 comprising the TCR sequence from the VCX54 CTL clone and envelop vector RD114 were co-transfected into package cell line GP2-293. CD8 and tetramer expression is shown by flow cytometry.

The TCR from the VCX54 CTL C7 clone was constructed into the retrovirus expression vector pMSGV1. A linker fragment containing a Furin cleavage site, a SGSG linker and a P2A cleavage site was inserted between the TCR-β chain and TCR-α chain to guarantee that both chain were expressed equally under the MSCV promoter (FIG. 9). The retrovirus expression vector pMSGV1 comprising the TCR sequence from the VCX54 CTL clone and an envelop vector RD114 were co-transfected into the package cell line GP2-293. Two to three days after transfection, the supernatant containing the retrovirus was used to infect the PBMCs which were activated for two days with 50 ng/mg OKT3 and 300 U/ml IL-2 stimulation. The infection was performed one more time after one day of the first infection. After 5 days, a clear CD8$^+$ Tetramer$^+$ population was detected by flow cytometry (FIG. 10).

Figure 11:
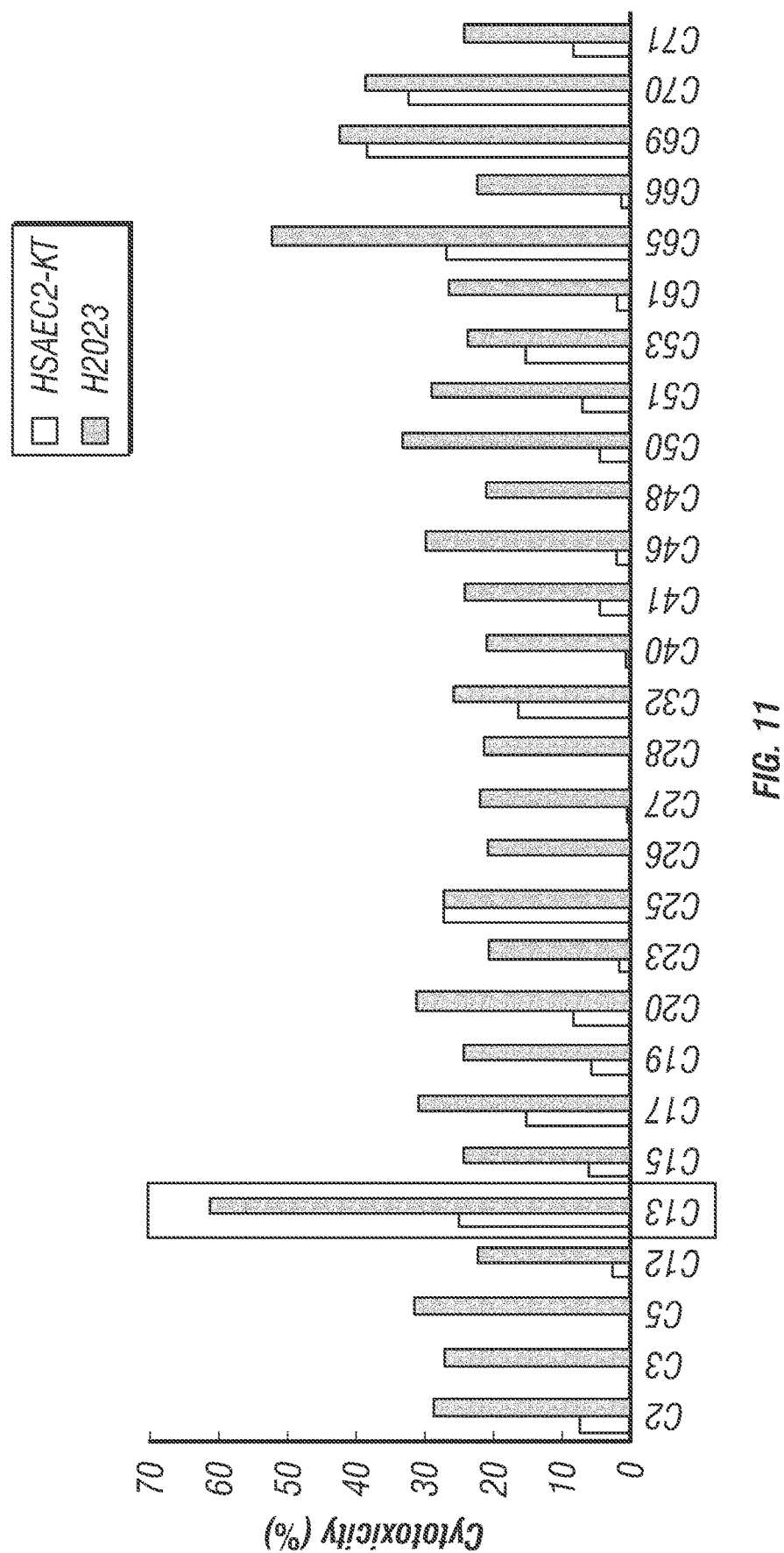
FIG. 11: 450 clones were screened with standard $_{51}$Cr release assay (CRA) using the VCX1+/HLA-A0201-positive lung cancer cell line H2023 and the HLA-A0201-positive immortalized normal human small airway epithelial HSAEC2-KT cells line. Only clones of cytotoxicity targeting H2023 by more than 20% are shown.
Figure 11:
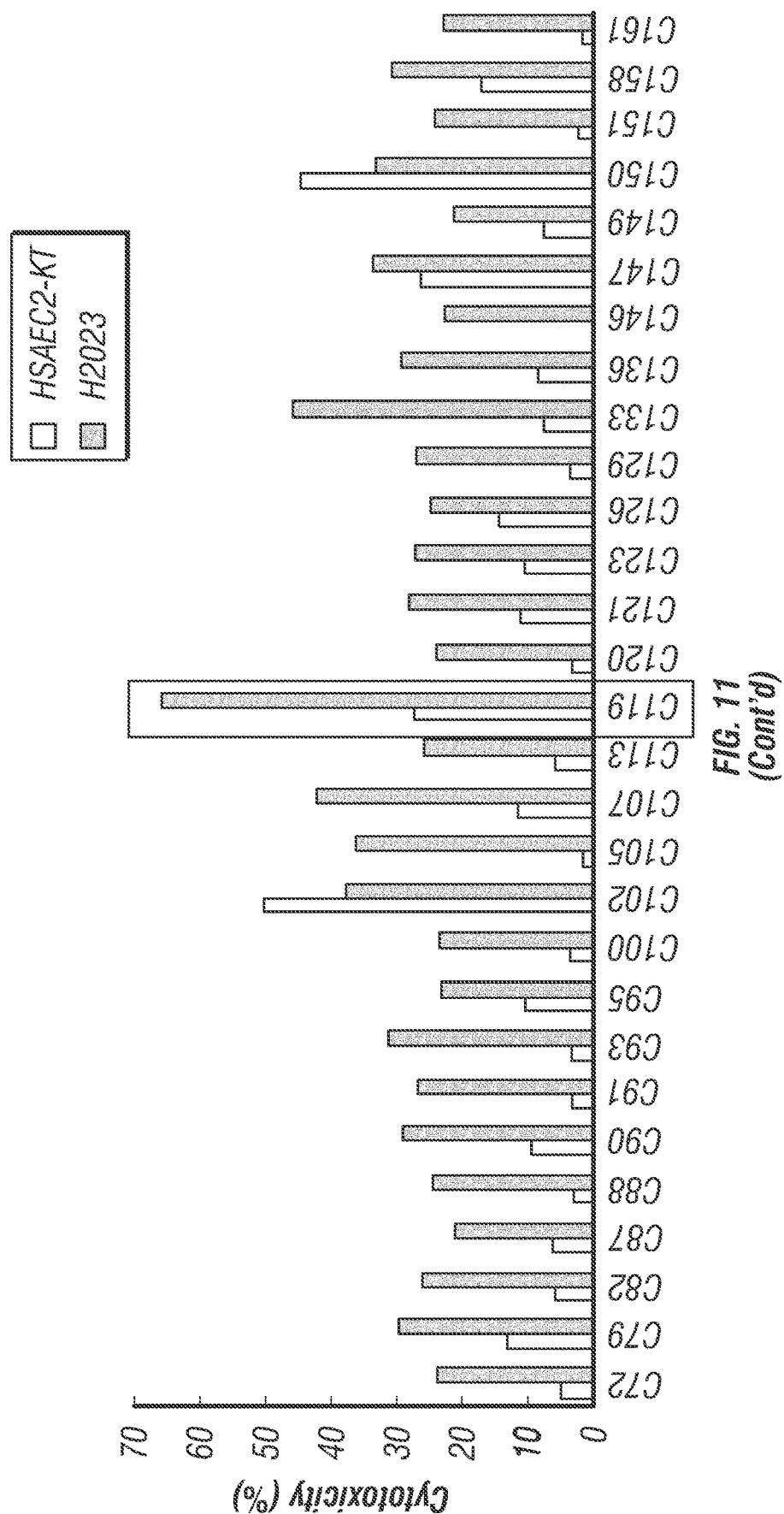

After infection, the T cells clones were generated using a limiting dilution method. 450 clones were screened with the standard 51Cr release assay (CRA) using the VCX1$^+$/HLA-A0201$^+$ lung cancer cell line H2023 and the HLA-A0201$^+$ immortalized normal human small airway epithelial cell line HSAEC2-KT as the control. Only clones that showed over twenty percent cytotoxicity against the H2023 cell line are shown in FIG. 11. The C13 and C119 clone were selected for further characterization.

Figure 12:
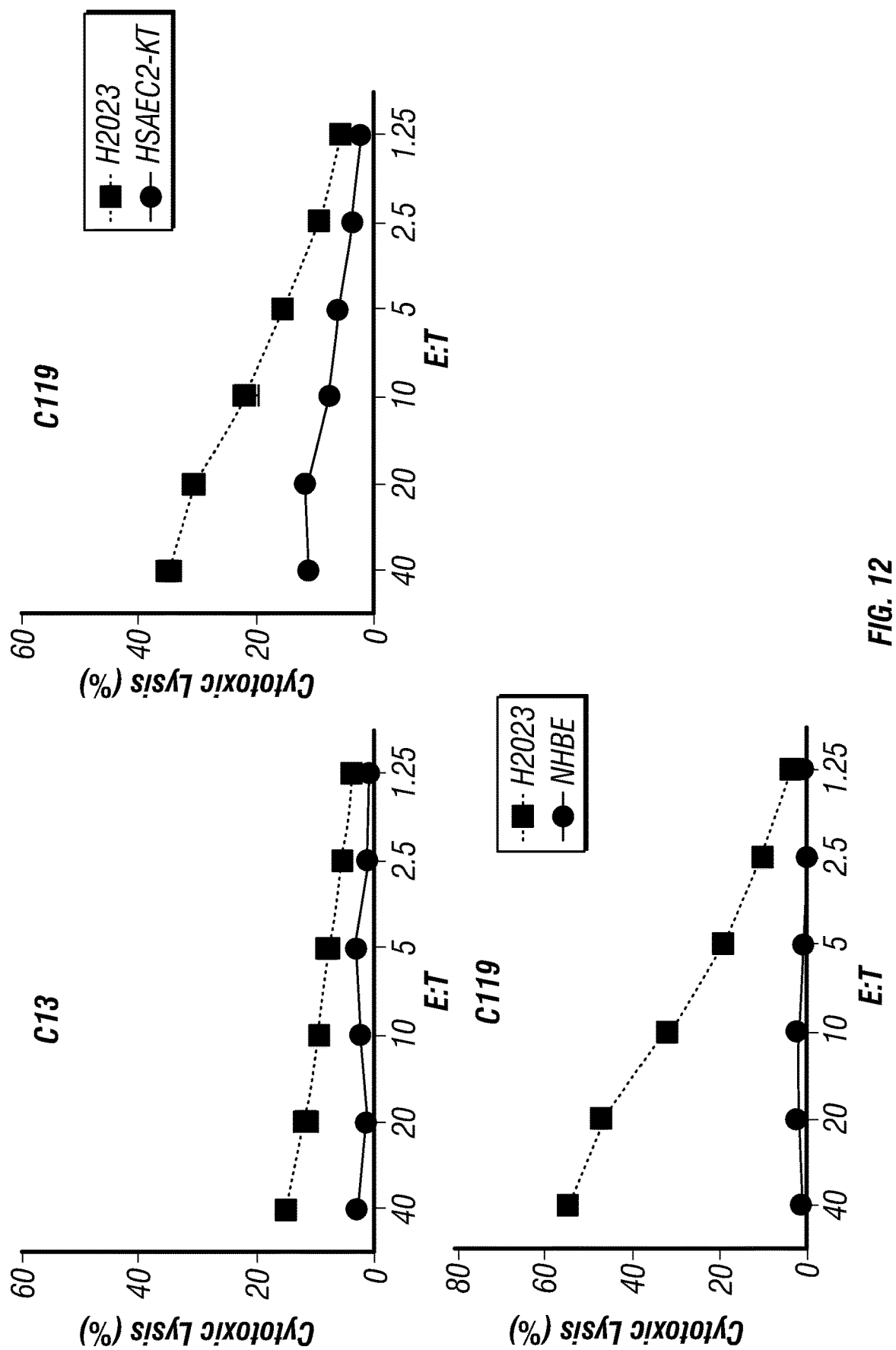
FIG. 12: Cytotoxicity of the TCR gene modified T cell clones C13 and C119 expanded using the rapid expansion protocol (REP).

The TCR gene modified T cell clones C13 and C119 were expanded using the rapid expansion protocol. The cytotoxicity of CTL clones to H2023 and HSAEC2-KT were detected again using CRA. The C119 CTL clone show higher cytotoxicity against the H2023 lung cancer cell line as compared to the C13 clone. For the normal lung cell line HSAEC2-KT, the C119 CTL clone showed very low cytotoxicity (FIG. 12). Furthermore, the C119 clone showed no cytotoxicity to the primary bronchial epithelial cell line NHBE (HLA-A0201$^+$).

Figure 13A:
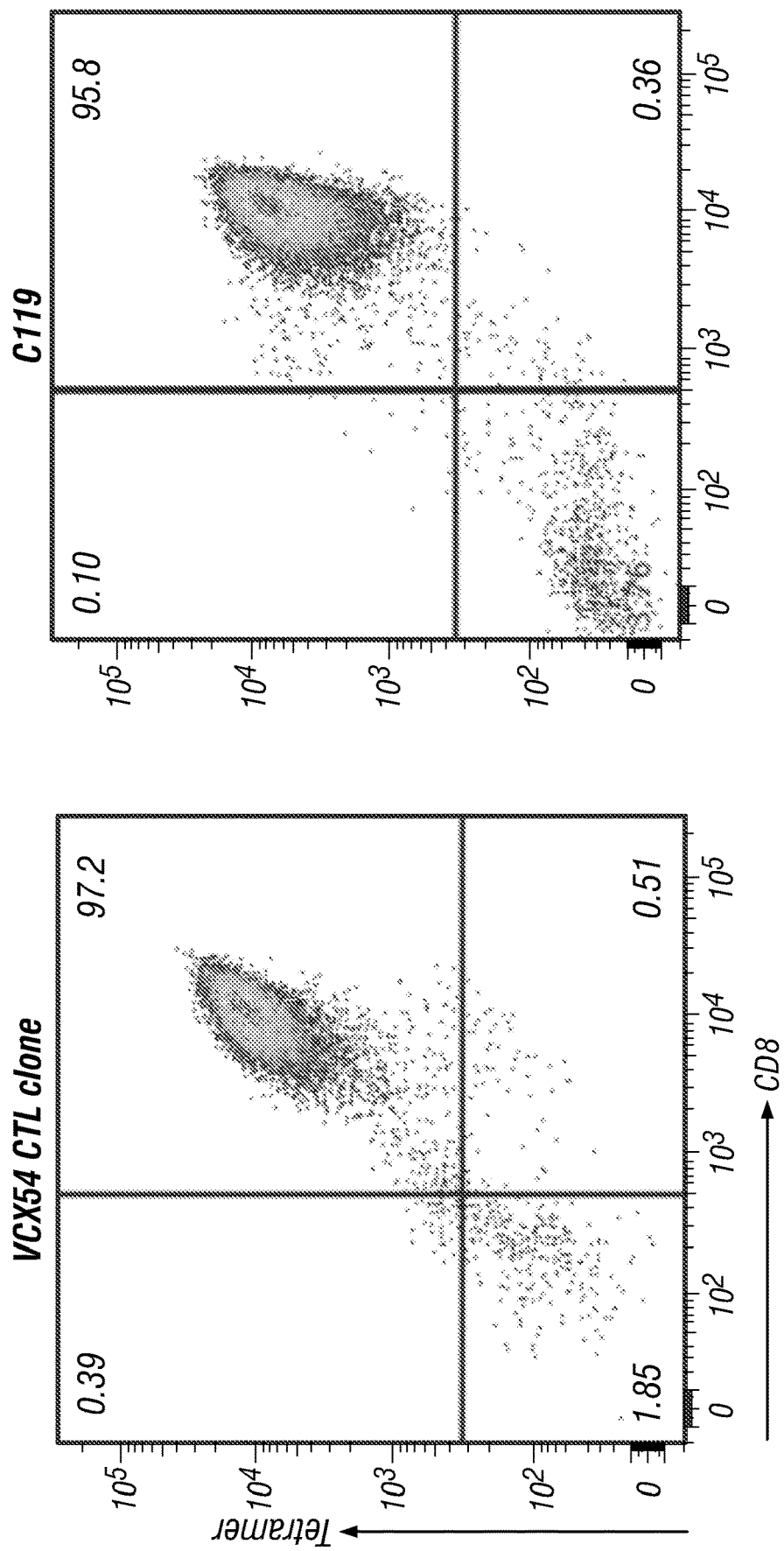
FIGS. 13A-13B: Tetramer staining and tetramer dissociation assay of TCR gene modified T cell clone C119. (A) Tetramer staining of parental VCX54 CTL clone and TCR gene modified T cell clone C119. The density of tetramer staining of C119 is compared to the parental CTL clone. (B) Tetramer dissociation detection. The time for half maximal binding ($T_{1/2}$) of the C119 clone is higher than parental VCX54 CTL clone.
Figure 13B:
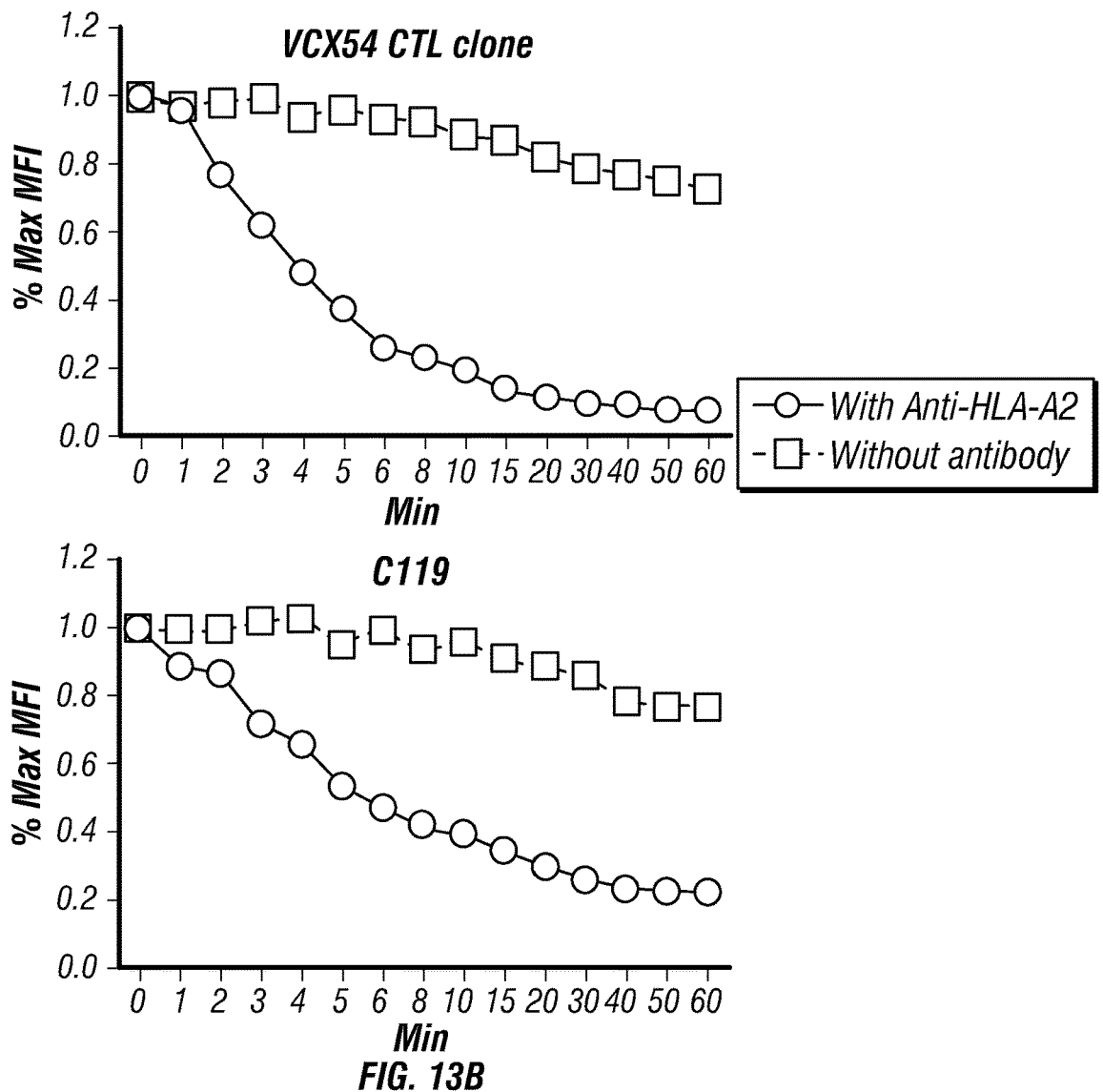

Thus, the C119 clone was analyzed by tetramer staining and tetramer dissociation assay. The tetramer staining of the parental VCX54 CTL clone and the TCR gene modified T cell clone C119 was observed to be similar (FIG. 13A). The tetramer dissociation assay showed that the time for half maximal binding ($T_{1/2}$) of the C119 clone is higher than parental VCX54 CTL clone (FIG. 13B).

Figure 14:
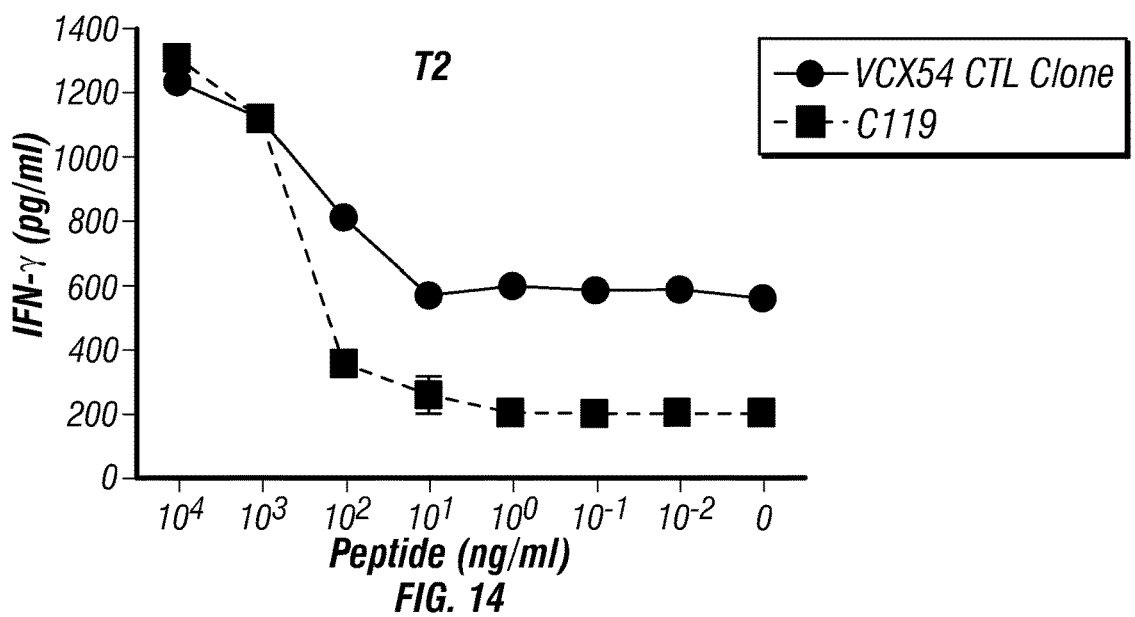
FIG. 14: Peptide titration assay for the specific response detection of the TCR gene modified T cells clone C119.
Figure 15A:
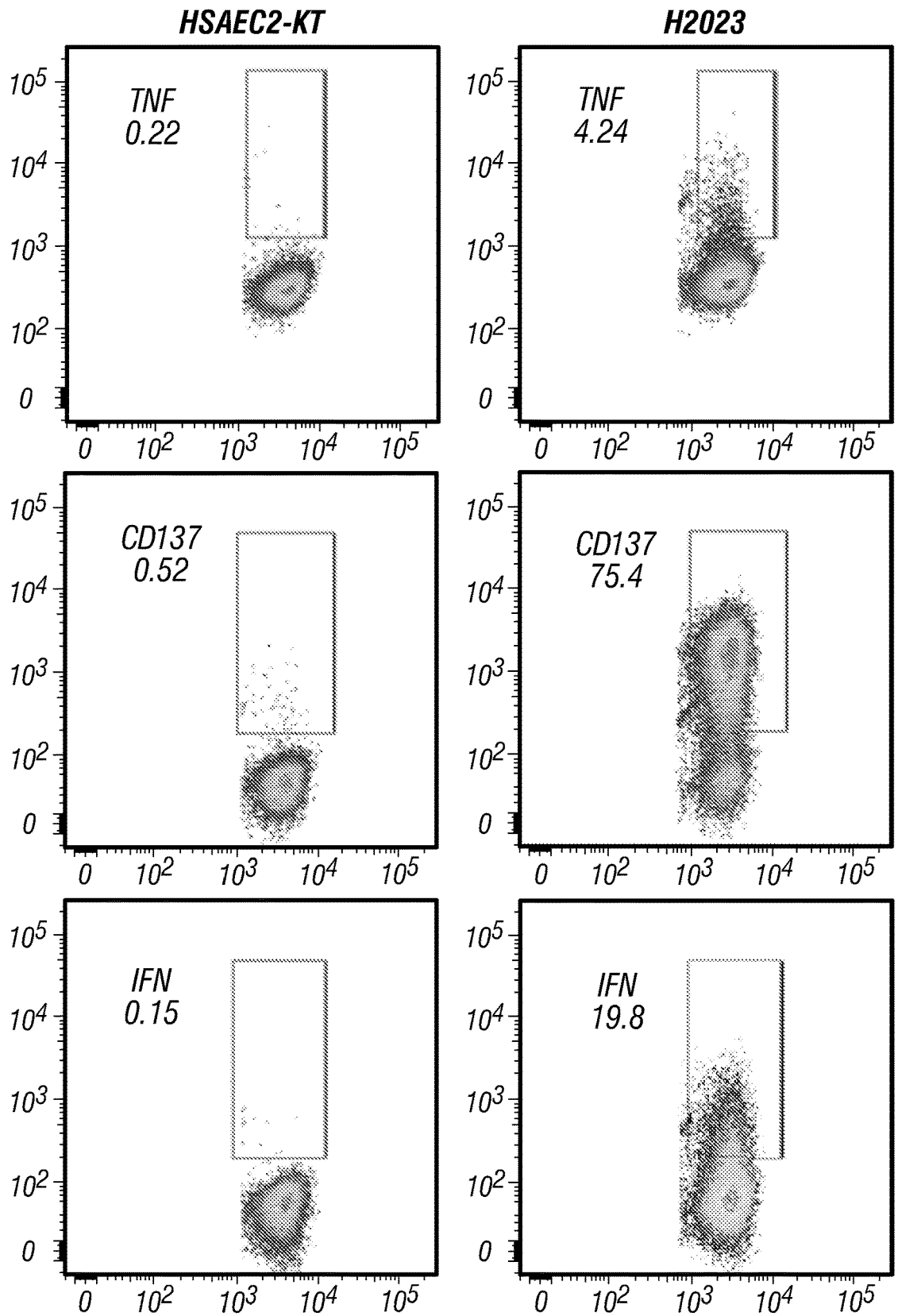
FIGS. 15A-15B: Intracellular staining assay to evaluate the specific response of TCR gene modified clone C119. The VCX54 parental CTL clone or TCR gene modified T cell clone C119 was co-cultured with (A) HLA-A2+/VCX1+ lung cancer cell line H2023 or HLA-A0201+ immortalized normal human small airway epithelial cell line HSAEC2-KT, or (B) T2 cells pulsed with 10 μg/ml VCX54 peptide or control peptide M26 at an effector to target (E:T) ratio of 10:1. The TNF-α, CD137, IFN-γ and IL-2 level in the intracellular were detected with flow cytometry.
Figure 15A:
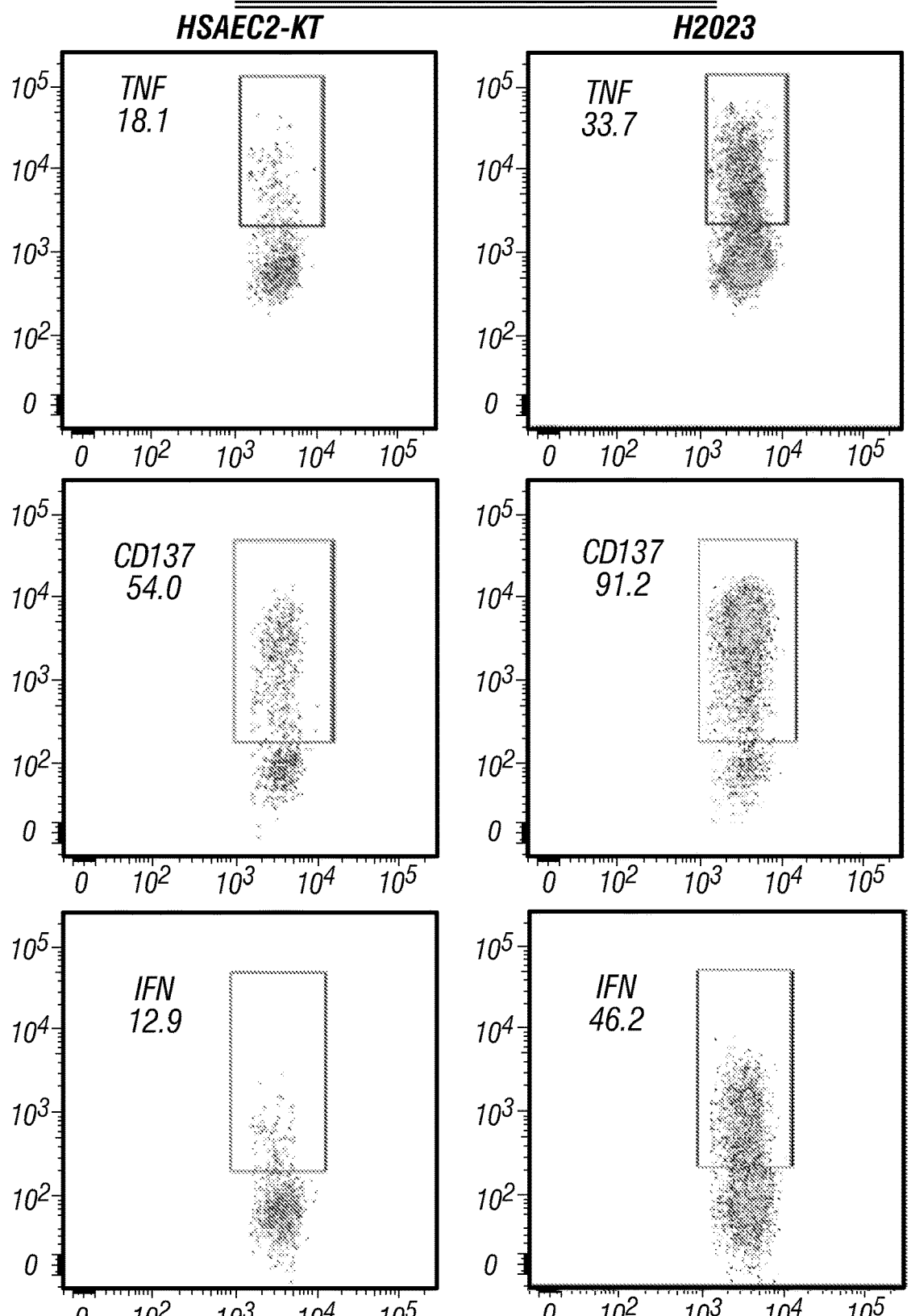
Figure 15A:
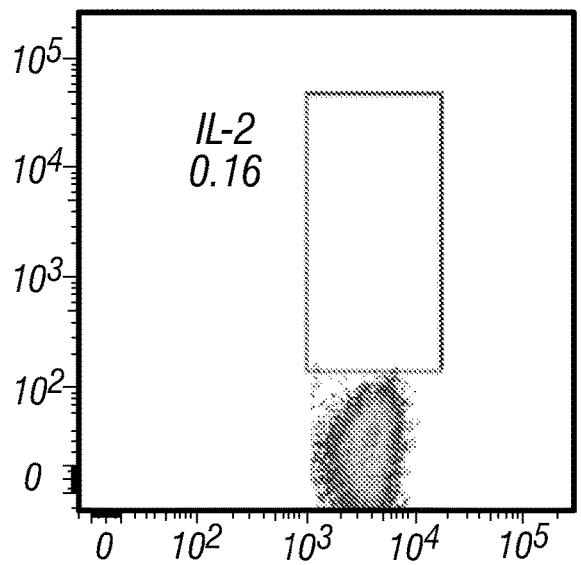
Figure 15A:
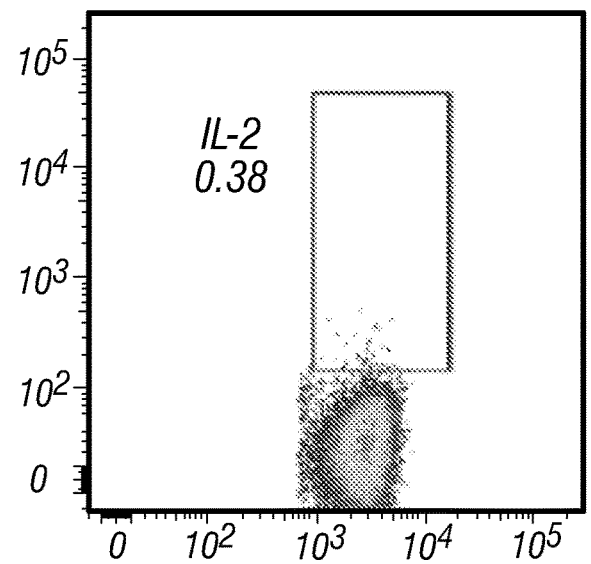
Figure 15A:
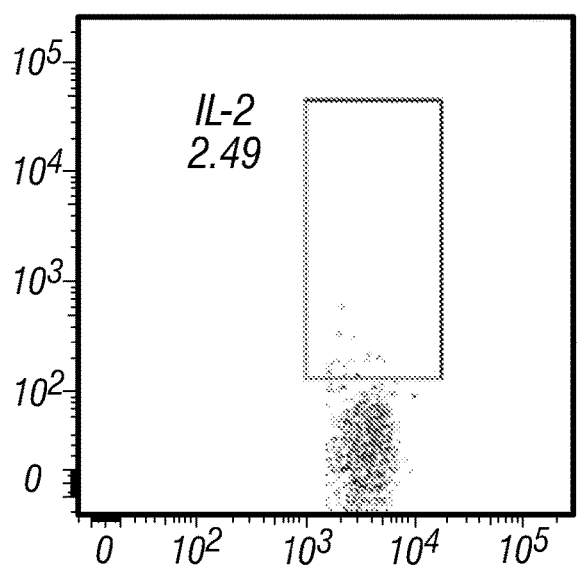
Figure 15A:
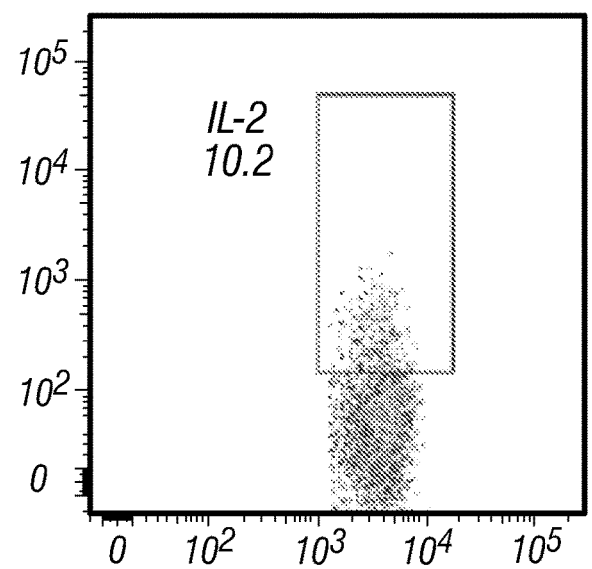
Figure 15B:
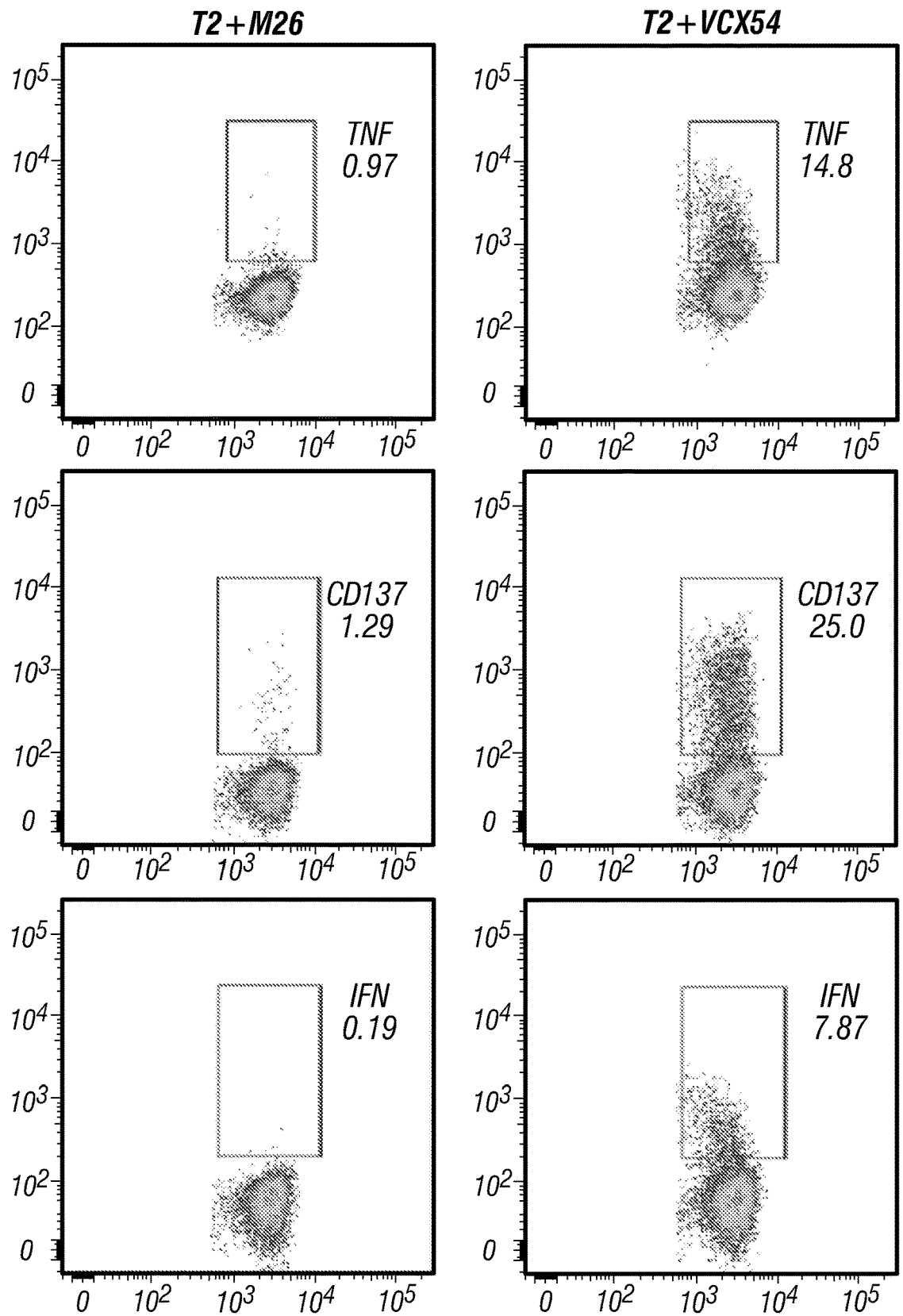
Figure 15B:
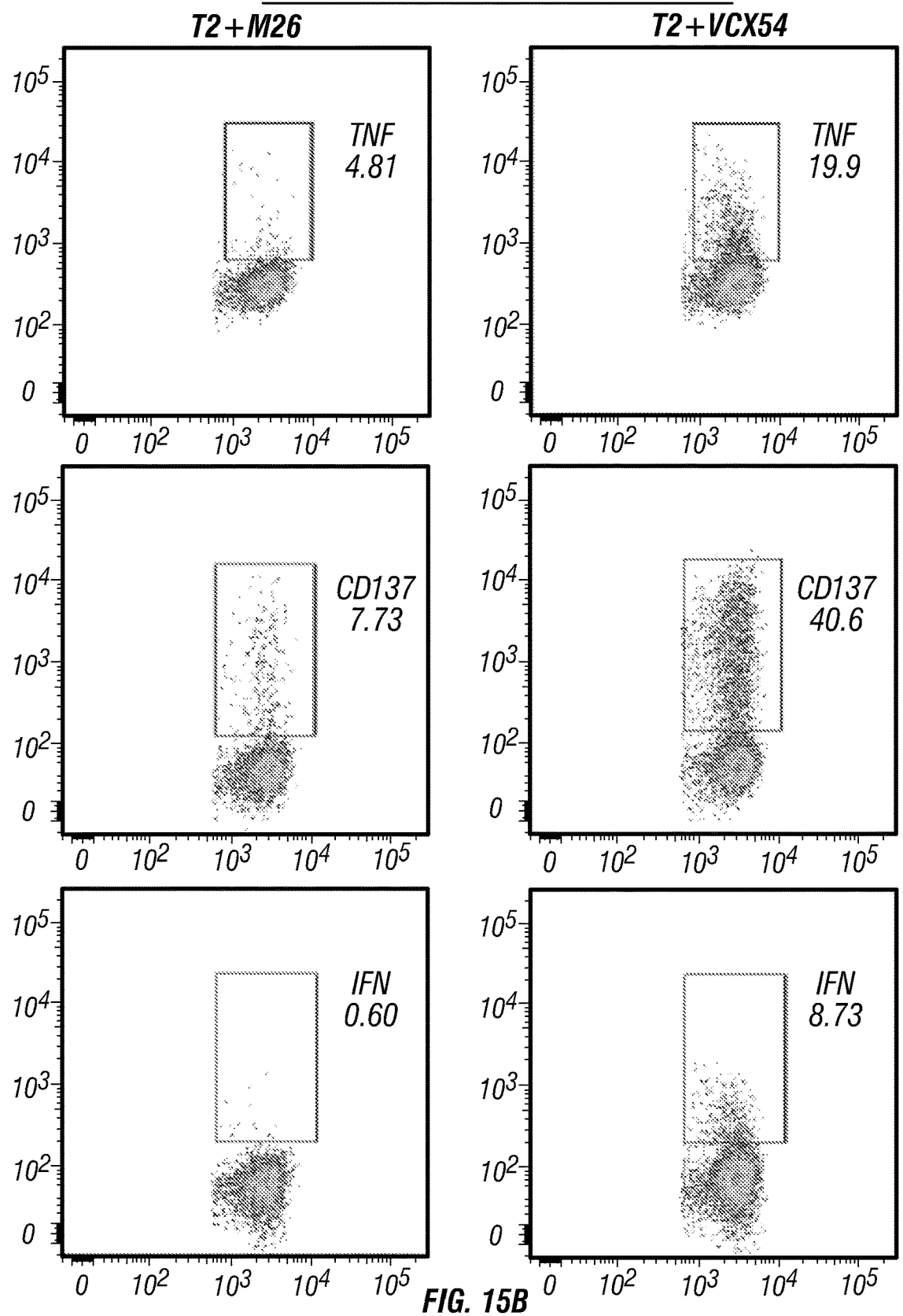
Figure 15B:
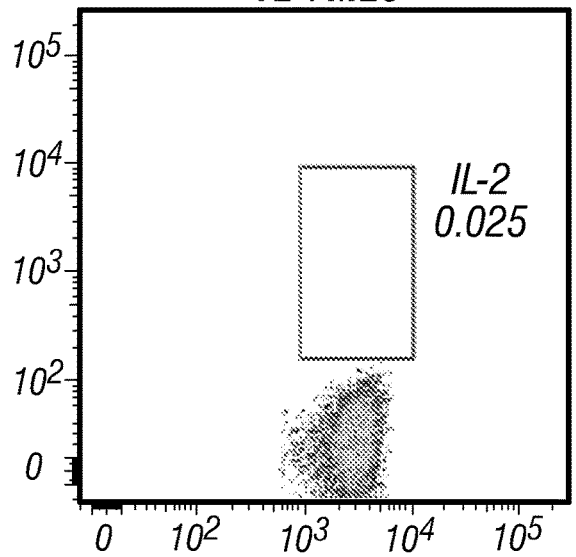
Figure 15B:
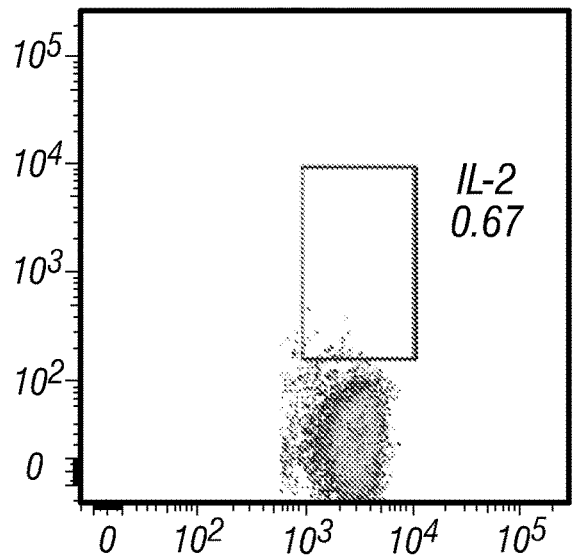
Figure 15B:
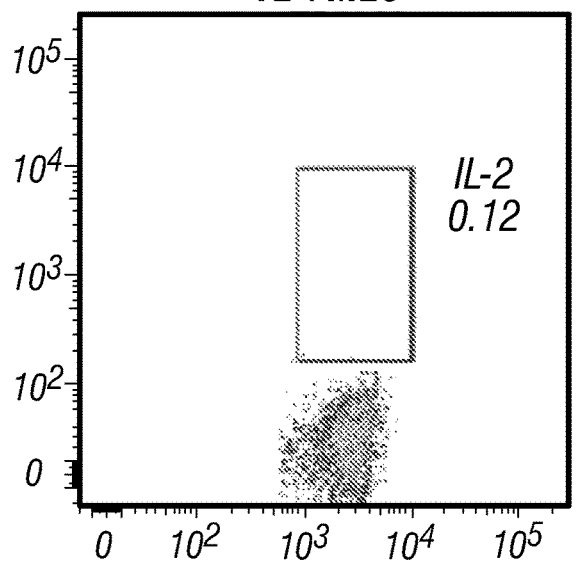
Figure 15B:
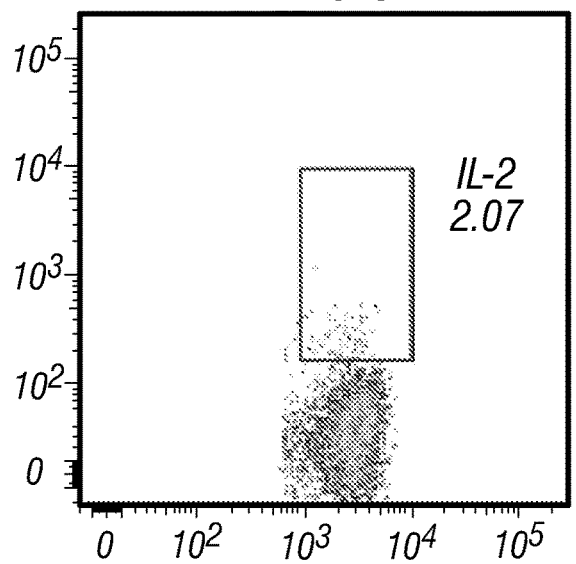

A peptide titration assay was performed for the specific response detection of the TCR gene modified T cell clone C119. The parental VCX54 CTL clone or the TCR gene modified T cell clone C119 was co-cultured with T2 cells pulsed with serially diluted concentrations of VCX54 peptide at an effector to target (E:T) ratio of 10:1 overnight. The IFN-γ release was detected with ELISA (FIG. 14). At high concentrations of peptide pulsing, the specific response of the VCX54 CTL clone or the TCR gene modified T cell clone C119 was comparable. At low concentration of peptide pulsing, the VCX54 CTL clone had higher unspecific background than the TCR gene modified T cell clone C119.

An intracellular staining assay was performed to evaluate the specific response of the TCR gene modified CTL clone C119. The VCX54 CTL clone or the TCR gene modified T cell clone C119 was co-cultured with the HLA-A2$^+$/VCX1$^+$ lung cancer cell line H2023, the HLA-A0201$^+$ immortalized normal human small airway epithelial cell HSAEC2-KT, or T2 cells pulsed with 10 μg/ml VCX54 peptide or control peptide M26 at an effector to target (E:T) ratio of 10:1 overnight. The TNF-α, CD137, IFN-γ and IL-2 intracellular levels were detected with flow cytometry. When co-cultured with tumor cells, the parental CTL clone showed higher TNF-α, CD137, IFN-γ and IL-2 levels as compared to TCR gene modified T cell clone C119, but also a higher background when co-cultured with normal lung cells (FIG. 15). When co-cultured with the T2 pulsed peptide, the TCR gene modified T cell clone C119 showed comparable TNF-α and IFN-γ levels to the parental CTL clone.

Figure 16:
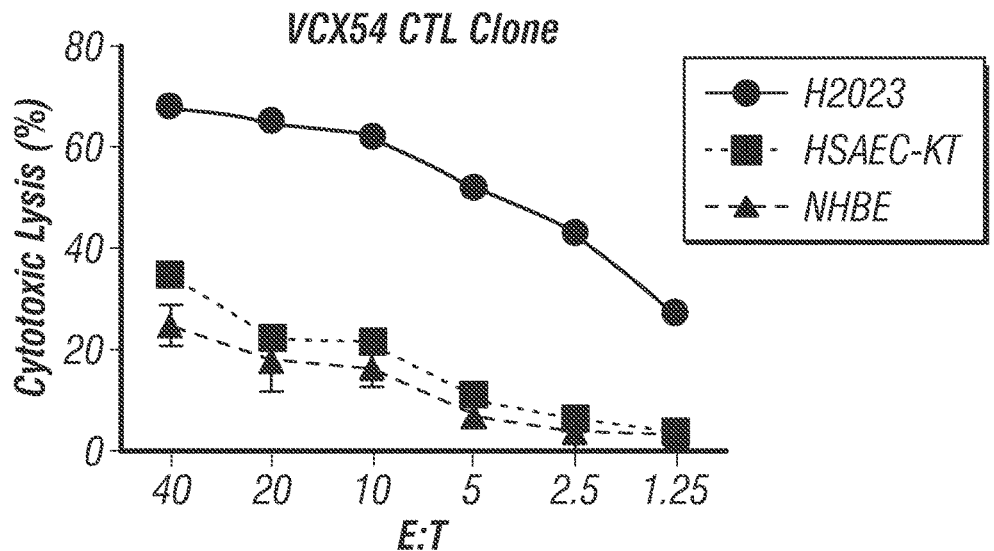
FIG. 16: Cytotoxicity of parental CTL clone and TCR gene modified T cell clone C119 to lung cancer cell line H2023, immortalized normal human small airway epithelial cell line HSAEC2-KT and primary human bronchial epithelial cells NHBE.
Figure 16:
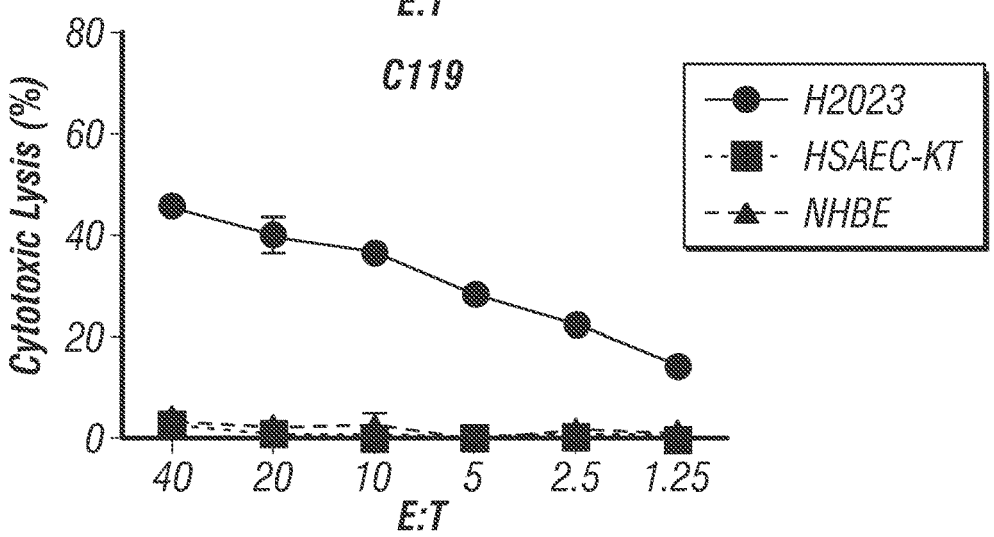

The cytotoxicity of the parental CTL clone and the TCR gene modified T cell clone C119 was compared. The lung cancer cell line H2023, normal lung cell line HSAEC2-KT and primary lung cells NHBE were used for the assay. The parental CTL clone and C119 clone were co-cultured with these cell lines and the cytotoxicity was detected with the standard $_{51}$Cr release assay (FIG. 16). The parental CTL clone showed higher cytotoxicity for tumor cells, but also had a low level of cytotoxicity for the normal lung cells. The TCR gene modified T cell clone C119 showed a slightly lower cytotoxicity for the tumor cells as compared to the parental CTL clone, but did not have any cytotoxicity for the normal lung cells. Thus, the C119 clone had a higher selective cytotoxicity towards the tumor cells versus normal cells.

Overall, these results suggest that a relevant tumor-associated antigenic epitope was identified, and was of sufficient immunogenicity to elicit antigen-specific T cells from PBMCs. Thus, the antigen-specific VCX54 peptide identified can be used to generate antigen-specific T cells for adoptive T cells transfer in the treatment of solid cancers.

Example 3—Materials and Methods

Generation and Expansion of VCX54-Specific CD8 T Cells:

Tumor antigen-specific CTLs were generated with a manner previously described (Li 2005). Leukapheresis PBMCs positive for HLA-A*0201 were stimulated by autologous DC pulsed with tumor antigen peptide. For induction of dendritic cell, adherent PBMCs were cultured with GM-CSF and IL-4 in AIM-V medium (Invitrogen Life Technologies) for 6 days and then added IL-1β, IL-6, TNF-α and PGE2 for maturation. After 1 day, mature DCs were pulsed with 40 μg/ml peptide at 2×10$^6$ cells/ml of 1% human serum albumin (HSA)/PBS in the present of 3 μg/ml beta-microglobulin for 4 hr at room temperature. After washing with 1% HSA/PBS, DCs were mixed with PBMCs at 1.5×10$^6$ cell/ml/well in 48 well plate. IL-21 (30 ng/ml) was added initially and 3~4 days after culture. IL-2 and IL-7 were added 1 day after secondary stimulation to expand activated antigen-specific T cells.

6 days after secondary stimulation, cells were stained with VCX/Y peptide/MHC-PE-conjugated tetramer and CD8-APC antibody, and then CD8 and tetramer-positive cells were sorted by ARIA II. The sorted VCX/Y-specific CD8 T cells were expanded by Rapid Expansion Protocol (REP) with feeder cells of PBL and LCL under IL-21.

Peptide-MHC Tetramer Staining:

VCX54-specific CD8 T cells were confirmed by staining with tetramer of VCX54 peptide/MHC complex for HLA A*0201. CD8 T cells were incubated with PE-conjugated tetramer for 20 mins, washed and then stained with APC-conjugated CD8 antibody for 15 mins in room temperature. After washing, cells were analyzed by flow cytometry (LSRFortessa X-20 Analyzer).

Generate T Cell Clone:

The whole length VCX3A RNA was transfected to matured dendritic cells (DC). The RNA transfected DC were co-cultured with autogenetic naïve T cell at the ratio of DC:T=1:10 in the presence of IL-21. After one week, the RNA-transfected DC were used to stimulate the T cells again. After two round of stimulation, the CD8$^+$ and tetramer+ double positive T cell population were sorted and expanded with rapid expansion protocol. The T cell clones were generated with limiting dilution method. The high activity CTL clones were screened via tumor cells killing assay.

TCR Cloning and Retrovirus Expression Vector Construction:

The TCR (including alpha chain and beta chain) were cloned using 5'-RACE method according to the manual of the kit (ClonTech Laboratories). The TCR V-alpha and TCR V-beta usage were identified with IMGT/V-QUEST annotation tool. Furthermore, TCR V-beta usage was also identified with flow detection using TCR VP Repertoire Kit. TCR V-alpha usage was identified with PCR using a panel of special primers which are annealed to 5' terminal of different TCR V-alpha. For the TCR expression retrovirus vector construction, the forward primers were designed according the TCR V-alpha or beta usage. The reverse primers were designed according the sequence of TCR alpha or beta constant region. Expression cassettes containing the alpha- and beta-TCR chains separated by the P2A linker peptide were generated and the whole length of PCR products were cloned in to retrovirus vector pMSGV1. The cloned DNA sequences were verified with sequencing.

The VCX-54 CTL TCR was determined to have the below sequence. The signal peptide is underlined, the CDRs are bold, and the variable region is italicized.

VCX-37 CTL TCR
(SEQ ID NO: 4)
<u>ATGTCACTTTCTAGCCTGCTGAAGGTGGTCACAGCTTCACTGTGGCTAG</u>

<u>GACCTGGCATT</u>*GCCCAGAAGATAACTCAAACCCAACCAGGAATGTTCGT*

*GCAGGAAAAGGAGGCTGTGACTCTGGACTGCACATATGA*CACCAGTGA

TCCAAGTTATGGT*CTATTCTGGTACAAGCAGCCCAGCAGTGGGGAAAT*

*GATTTTTCTTATTTAT*CAGGGGTCTTATGACCAGCAAAAT*GCAAC*

*AGAAGGTCGCTACTCATTGAATTTCCAGAAGGCAAGAAAATCCGCCAACC*

*TTGTCATCTCCGCTTCACAACTGGGGACTCAGCAATGTATTTCTGT*

*GCAATGATA*A*CCTCTGGCAACACAGGC*A*AAACTAATC**TTTGGGCAAG*

GGACAACTTTACAAGTAAAACCAGATATCCAGAACCCTGACCCTGCCGT

GTACCAGCTGAGAGACTCTAAATCCAGTGACAAGTCTGTCTGCCTATTC

ACCGATTTTGATTCTCAAACAAATGTGTCACAAAGTAAGGATTCTGATG

TGTATATCACAGACAAAACTGTGCTAGACATGAGGTCTATGGACTTCAA

GAGCAACAGTGCTGTGGCCTGGAGCAACAAATCTGACTTTGCATGTGCA

AACGCCTTCAACAACAGCATTATTCCAGAAGACACCTTCTTCCCCAGCC

CAGAAAGTTCCTGTGATGTCAAGCTGGTCGAGAAAAGCTTTGAAACAGA

TACGAACCTAAACTTTCAAAACCTGTCAGTGATTGGGTTCCGAATCCTC

CTCCTGAAAGTGGCCGGGTTTAATCTGCTCATGACGCTGCGGCTGTGGT

CCAGCTGA

VCX-37 TL TCR Alpha Chain
(SEQ ID NO: 5)
<u>MSLSSLLKVV TASLWLGPGI</u> *AQKITQTQPG MFVQEKEAVT*

*LDCTYD*TSDP *SYGLFWYKQP SSGEMIFLIY* QGSYDQQN*AT*

*EGRYSLNFQK ARKSANLVIS ASQLGDSAMY FC*AMITSGNT

GKLIF*GQGTT LQVKPDIQNP DPAVYQLRDS KSSDKSVCLF*

TDFDSQTNVS QSKDSDVYIT DKTVLDMRSM DFKSNSAVAW

SNKSDFACAN AFNNSIIPED TFFPSPESSC DVKLVEKSFE

TDTNLNFQNL SVIGFRILLL KVAGFNLLMT LRLWSS

VCX-37 CTL TCR Beta Chain
(SEQ ID NO: 6)
<u>ATGCTTAGTCCTGACCTGCCTGACTCTGCCTGGAACACCAGGCTCCTCT</u>

<u>GCCGTGTCATGCTTTGTCTCCTGGGAGCAGGTTCAGTG</u>*GCTGCTGGAGT*

*CATCCAGTCCCCAAGACATCTGATCAAAGAAAAGAGGGAAACAGCCACT*

*CTGAAATGCTATCCTAT*C*CCTAG*A*CACGACACT**GTCTACTGGTACCAG*

*CAGGGTCCAGGTCAGGACCCCCAGTTCCTCATTTCG*TTTTATGAAA

AGATGCAG*AGCGATAAAGGAAGCATCCCTGATCGATTCTCAGCTCAAC*

*AGTTCAGTGACTATCATTCTGAACTGAACATGAGCTCCTTGGAGCTGGG*

*GGACTCAGCCCTGTACTTCTGT*GCCAGCAGCCCCCGGCGGGGGCG

GACTGAAGCTTTC*TTTGGACAAGGCACCAGACTCACAGTTGTAGAGGA*

CCTGAACAAGGTGTTCCCACCCGAGGTCGCTGTGTTTGAGCCATCAGAA

GCAGAGATCTCCCACACCCAAAAGGCCACACTGGTGTGCCTGGCCACAG

GCTTCTTCCCTGACCACGTGGAGCTGAGCTGGTGGGTGAATGGGAAGGA

GGTGCACAGTGGGGTCAGCACGGACCCGCAGCCCCTCAAGGAGCAGCCC

GCCCTCAATGACTCCAGATACTGCCTGAGCAGCCGCCTGAGGGTCTCGG

CCACCTTCTGGCAGAACCCCCGCAACCACTTCCGCTGTCAAGTCCAGTT

CTACGGGCTCTCGGAGAATGACGAGTGGACCCAGGATAGGGCCAAACCC

GTCACCCAGATCGTCAGCGCCGAGGCCTGGGGTAGAGCAGACTGTGGCT

TTACCTCGGTGTCCTACCAGCAAGGGGTCCTGTCTGCCACCATCCTCTA

GTGAGATCCTGCTAGGAAGGCCACCCTGTATGCTGTGCTGGTCAGCGCC

CTTGTGTTGATGGCCATGGTCAAGAGAAAGGATTTCTAG

VCX-37 CTL TCR Beta Chain
(SEQ ID NO: 7)
<u>MLSPDLPDSA WNTRLLCRVM LCLLGAGSVA</u> *AGVIQSPRHL*

*IKEKRETATL KCYPI*PRHDT *VYWYQQGPGQ DPQFLIS*FYE

KMQ*SDKGSIP DRFSAQQFSD YHSELNMSSL ELGDSALYFC*

*ASSPPGGGRT EAFF**GQGTRL TVVEDLNKVF PPEVAVFEPS*

EAEISHTQKA TLVCLATGFF PDHVELSWWV NGKEVHSGVS

TDPQPLKEQP ALNDSRYCLS SRLRVSATFW QNPRNHFRCQ

VQFYGLSEND EWTQDRAKPV TQIVSAEAWG RADCGFTSVS

YQQGVLSATI LYEILLGKAT LYAVLVSALV LMAMVKRKDF

Retrovirus Generation and Infect Human Peripheral Blood Lymphocytes (PBL):

The pMSGV1 vector containing the TCR and the envelope vector RD114 were cotransfected to the package cell line GP2-293. After transfection for 6-8 hours, the medium were refreshed. The supernatant was harvested 24 hours later and was added to the 6 well plate which has been coated with 20 mg/mL RetroNectin followed by centrifugation (2000×g) at 32° C. for 2 hours. The supernatant was removed then and the PBL which were activated with 50 ng/ml OKT3 and 300 U/ml IL-2 for two days were added to the retrovirus loaded plate followed by centrifugation (1000×g) at 32° C. for 10 min. Cells were then incubated overnight at 32° C., and the procedure was repeated the following day (total of two transductions). After that, the cells were expanded at 37° C. in a 5% CO2 incubator and split as necessary.

TCR Engineered T Cell Clone Generation:

After infection, the CD8$^+$ and tetramer+ T cell population were sorted and T cell clones were generated with limiting dilution method. The high activity CTL clone were screened via tumor cells killing assay. The high tumor killing activity T cell clone were further expanded with REP.

$^{51}$Cr Release Assay:

The killing ability of the TCR engineered T cell or CTL clone to lyse HLA-A2 tumor targets was measured using a standard $^{51}$Cr release assay. Tumor cells or normal cells were labeled for 2 h at 37° C. with 200 μCi of $^{51}$Cr. Labeled target cells were washed and then incubated with effector cells at the different ratios for 4 h at 37° C. in 0.2 ml of complete medium. Harvested supernatants were counted using automatic gamma counter. Maximal and spontaneous $^{51}$Cr release was determined by incubating the labeled target cells in either trypan lysis buffer or medium for 4 h at 37°

C. Each data point was determined as an average of quadruplicate wells. The percent specific lysis was calculated as follows: % killing=((specific release−spontaneous release)/(total release−spontaneous release))×100.

IFN-γ Release Assay:

IFN-γ release from T cell was detected with ELISA method. The T cells were incubated with target cells at 10:1 ration in 96 well plate with 0.2 ml medium at 37° C. After co-culturing overnight, the supernatant was harvested and the IFN-γ concentration was detected using ELISA according to the manual of the kit (Invitrogen Life Technologies).

Intracellular Cytokine Staining (ICS) Assay:

The T cells were incubated with target cells at 10:1 ration in the presence of brefeldin A (BFA) at 37° C. overnight. After co-culturing, the T cells were harvested and washed. The cells were stained with flow antibody anti surface marker first. After that, the cells were washed and fixed with Fix Buffer and then were permeabilized using Permeabilizing Solution (eBioscience). Permeabilized cells are then stained with intracellular cytokine flow antibody. Finally, the level of cytokine producing in the cells was analyzed using FACS.

Statistical Analysis:

Data analysis was performed using GraphPad prism version 6.0e. Normally distributed data were analyzed using parametric tests (Anova or unpaired t-test). Statistical test differences were considered significant if p values were <0.05.

Example 4—Additional VCX/Y Family Peptides

Additional studies were performed to identify VCX/Y family candidate HLA-A2 restricted peptides. The results of the studies are shown in Table 2.

TABLE 2

Candidate HLA-A2 restricted peptides from VCX/Y family.

| Name | HLA restrict | Sequence | Shared in VCX/Y family | NetMHC score (nM) |
|---|---|---|---|---|
| VCX-37 | HLA-A0201 | KVAKKGKAV (SEQ ID NO: 8) | VCX1, VCX2, VCX3A, VCX3B | 15189.81 |
| VCY-37 | HLA-A0201 | KVAEKGEAV (SEQ ID NO: 12) | VCY | 875.17 |
| VCX-54 | HLA-A0201 | GAATKMAAV (SEQ ID NO: 1) | All VCX/Y members | 2621.46 |
| VCX-58 | HLA-A0201 | KMAAVEAPEA (SEQ ID NO: 13) | All VCX/Y members | 77.16 |
| VCX-59 | HLA-A0201 | MAAVEAPEA (SEQ ID NO: 14) | All VCX/Y members | 6850.65 |
| VCX-178 | HLA-A0201 | SEMEELPSV (SEQ ID NO: 9) | VCX1, VCX3A, VCX3B | 688.68 |

Figure 17A:
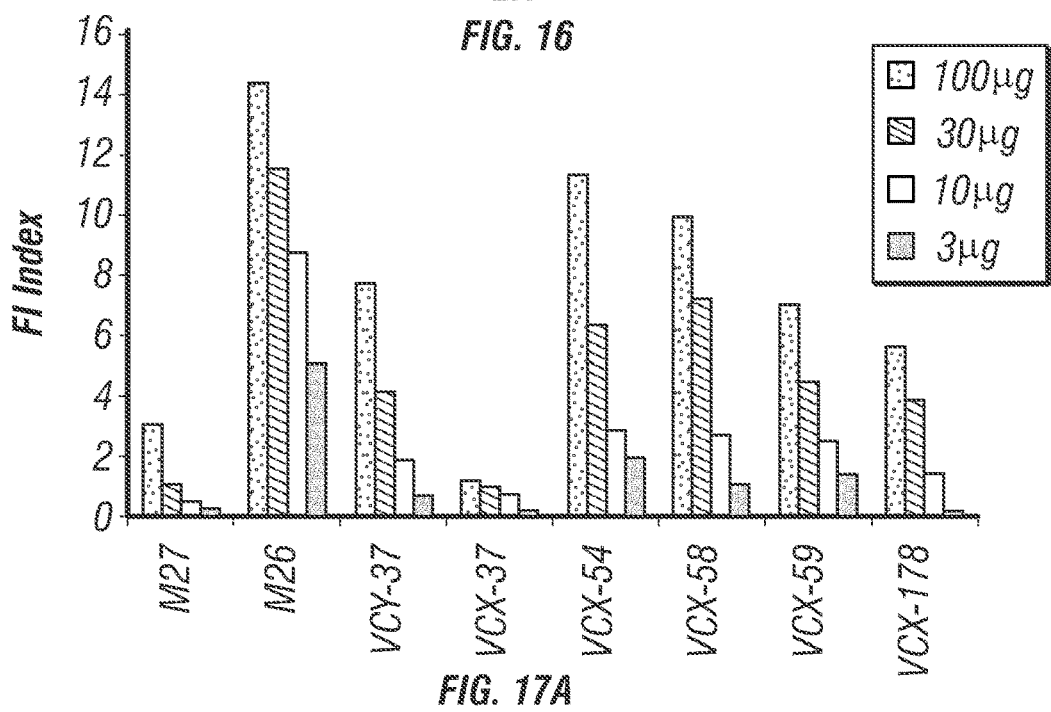
FIGS. 17A-17C: HLA-A2 restricted peptides from VCX/Y family (A) HLA binding assay of peptide (HLA-A2 stabilization detection). (B) VCY-37 tetramer detections of CTLs. (C) Chromium release assay of VCY-37 CTLs to lung tumor or normal lung cell line.

The peptides were synthesized and pulsed with T2 cells with a series of diluted concentrations for 18 hours. After incubation, the HLA-A2 expression level of T2 was detected by flow cytometry and the FI index was calculated. The M27 peptide was used as a weak binding peptide control and the M26 peptide was used as a strong binding peptide control. From the binding assay, it was found that the VCX-54 peptide showed the strongest binding to the HLA-A2 allele (FIG. 17A). The VCX-58 and VCY-37 peptides also showed strong binding ability to the HLA-A2 allele.

Figure 17B:
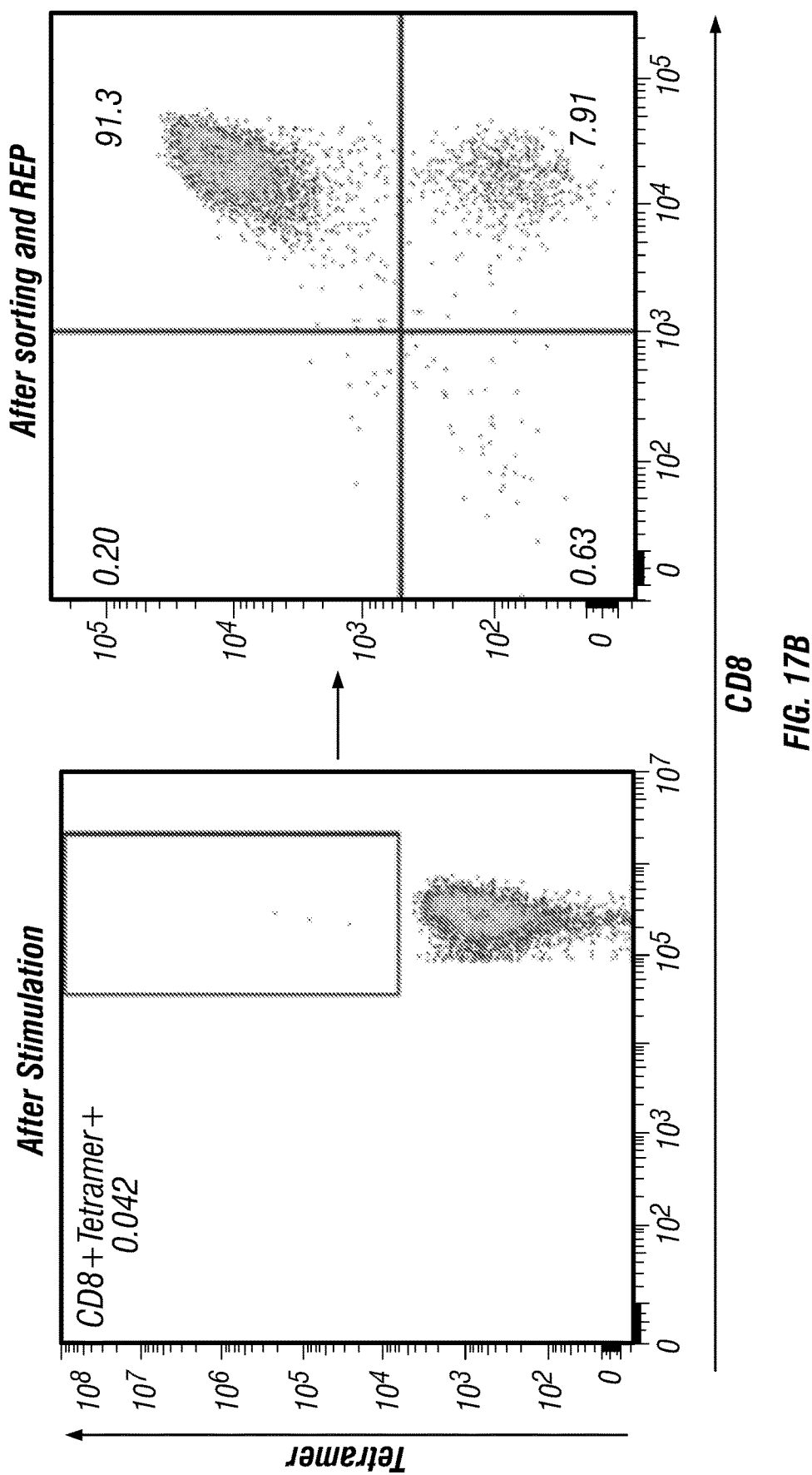

Next, dendritic cells were pulsed with VCY whole length RNA and HLA-A2+ cells were stimulated. After 2 rounds of stimulation, the T cells were stained with VCY-37 tetramer and anti-CD8 antibody. The tetramer⁺CD8⁺ population was sorted and subjected to rapid expansion. After rapid expansion, the CTLs were re-stained with VCY-37 tetramers and anti-CD8 antibody. It was found that over 90% of the cell population was tetramer⁺CD8⁺ (FIG. 17B).

Figure 17C:
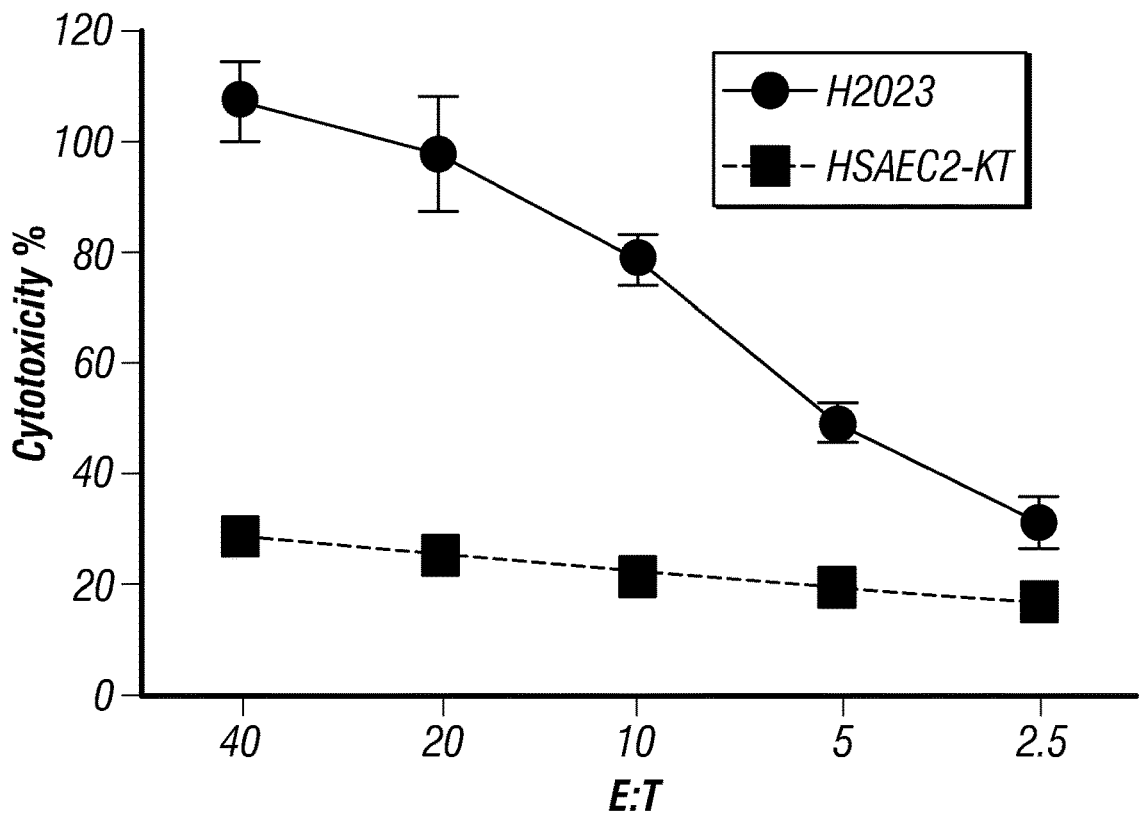
Figure 17C:
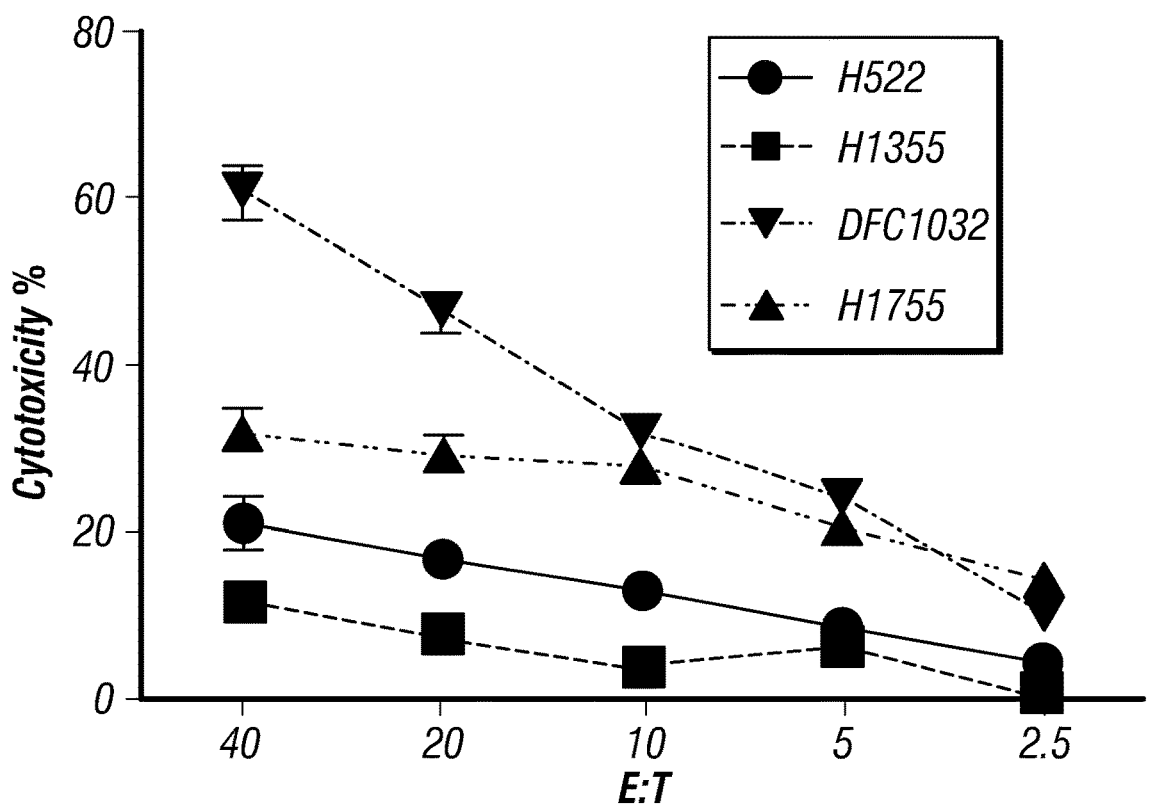

Further, the VCY-37 CTL cell line was co-cultured with VCX1 positive expression human lung cancer cell line H2023 (HLA-A*0201⁺) or the immortalized normal small air epithelial cell line HSAEC2-KT (HLA-A*0201⁺) at various E:T ratios. The cytotoxicity lysis was detected with the standard 51Cr release assay (CRA) (FIG. 17C). Furthermore, several HLA-A0201⁺ lung cancer cell lines were used as targets to test the VCY-37 CTL killing ability. The data showed that a high level of cytotoxicity was observed in lung cancer cells H2023 but not in the normal lung cells HSAEC2-KT. This was validated in other lung cancer cell lines.

The TCR of the VCY-37 cells was sequenced and found to have the sequence below. The signal peptide is underlined, the CDRs are bold, and the variable region is italicized.

VCY-37 Alpha Chain
(SEQ ID NO: 15)
<u>ATGCTGACTGCCAGCCTGTTGAGGGCAGTCATAGCCTCCATCTGTGTTG</u>

<u>TATCCAGCATG</u>*GCTCAGAAGGTAACTCAAGCGCAGACTGAAATTTCTGT*

*GGTGGAGAAGGAGGATGTGACCTTGGACTGTGTGTATGAA**ACCCGTGATA*

*CTACTTATTAC**TTATTCTGGTACAAGCAACCACCAAGTGGAGAATTGG*

*TTTTCCTTATTCGT**CGGAACTCTTTTGATGAGCAAAAT**GAAATAAGT*

*GGTCGGTATTCTTGGAACTTCCAGAAATCCACCAGTTCCTTCAACTTCA*

*CCATCACAGCCTCACAAGTCGTGGACTCAGCAGTATACTTCTGT*

*GCTCTGAGCTTACTATCTTATAACACCGACAAGCTCATC**TTTG*

*GGACTGGGACCAGATTACAAGTCTTTCCAAATATCCAGAACCCTGACCC*

*TGCCGTGTACCAGCTGAGAGACTCTAAATCCAGTGACAAGTCTGTCTGCC*

*TATTCACCGATTTTGATTCTCAAACAAATGTGTCACAAAGTAAGGATTC*

*TGATGTGTATATCACAGACAAAACTGTGCTAGACATGAGGTCTATGGAC*

*TTCAAGAGCAACAGTGCTGTGGCCTGGAGCAACAAATCTGACTTTGCAT*

*GTGCAAACGCCTTCAACAACAGCATTATTCCAGAAGACACCTTCTTCCC*

*CAGCCCAGAAAGTTCCTGTGATGTCAAGCTGGTCGAGAAAAGCTTTGAA*

*ACAGATACGAACCTAAACTTTCAAAACCTGTCAGTGATTGGGTTCCGAA*

*TCCTCCTCCTGAAAGTGGCCGGGTTTAATCTGCTCATGACGCTGCGGCT*

*GTGGTCCAGCTGA*

VCY-37 Alpha Chain
(SEQ ID NO: 16)
<u>MLTASLLRAV IASICVVSSM</u> *AQKVTQAQTE ISVVEKEDVT*

```
                                                -continued
LDCVYETRDT  TYYLFWYKQP  PSGELVFLIR  RNSFDEQNEI

SGRYSWNFQK  STSSFNFTIT  ASQVVDSAVY  FCALSLLSYN

TDKLIFGTGT  RLQVFPNIQN  PDPAVYQLRD  SKSSDKSVCL

FTDFDSQTNV  SQSKDSDVYI  TDKTVLDMRS  MDFKSNSAVA

WSNKSDFACA  NAFNNSIIPE  DTFFPSPESS  CDVKLVEKSF

ETDTNLNFQN  LSVIGFRILL  LKVAGFNLLM  TLRLWSS

VCY-37 TCR Beta Chain
                                            (SEQ ID NO:17)
ATGGGCACCAGCCTCCTCTGCTGGATGGCCCTGTGTCTCCTGGGGGCAG

ATCACGCAGATACTGGAGTCTCCCAGGACCCCAGACACAAGATCACAAA

GAGGGGACAGAATGTAACTTTCAGGTGTGATCCAATTTCTGAACA

CAACCGCCTTTATTGGTACCGACAGACCCTGGGGCAGGGCCCAGAGTTT

CTGACTTACTTCCAGAATGAAGCTCAACTAGAAAAATCAAGGCTGCTCA

GTGATCGGTTCTCTGCAGAGAGGCCTAAGGGATCTTTCTCCACCTTGGA

GATCCAGCGCACAGAGCAGGGGGACTCGGCCATGTATCTCTGT

GCCAGCAGCACCCCCGGGCCCTCTGGGGCCAACGTCCTGACTTTCGG

GGGCCGGCAGCAGGCTGACCGTGCTGGAGGACCTGAAAAACGTGTTCCC

ACCCGAGGTCGCTGTGTTTGAGCCATCAGAAGCAGAGATCTCCCACACC

CAAAAGGCCACACTGGTGTGCCTGGCCACAGGCTTCTTCCCTGACCACG

TGGAGCTGAGCTGGTGGGTGAATGGGAAGGAGGTGCACAGTGGGGTCAG

CACGGACCCGCAGCCCCTCAAGGAGCAGCCCGCCCTCAATGACTCCAGA

TACTGCCTGAGCAGCCGCCTGAGGGTCTCGGCCACCTTCTGGCAGAACC

CCCGCAACCACTTCCGCTGTCAAGTCCAGTTCTACGGGCTCTCGGAGAA

TGACGAGTGGACCCAGGATAGGGCCAAACCCGTCACCCAGATCGTCAGC

GCCGAGGCCTGGGGTAGAGCAGACTGTGGCTTTACCTCGGTGTCCTACC

AGCAAGGGGTCCTGTCTGCCACCATCCTCTATGAGATCCTGCTAGGGAA

GGCCACCCTGTATGCTGTGCTGGTCAGCGCCCTTGTGTTGATGGCCATG

GTCAAGAGAAAGGATTTCTGA

VCY-37 TCR Beta Chain
                                            (SEQ ID NO:18)
MGTSLLCWMA  LCLLGADHAD  TGVSQDPRHK  ITKRGQNVTF

RCDPISEHNR  LYWYRQTLGQ  GPEFLTYFQN  EAQLEKSRLL

SDRFSAERPK  GSFSTLEIQR  TEQGDSAMYL  CASSTPGPSG

ANVLTFGAGS  RLTVLEDLKN  VFPPEVAVFE  PSEAEISHTQ

KATLVCLATG  FFPDHVELSW  WVNGKEVHSG  VSTDPQPLKE

QPALNDSRYC  LSSRLRVSAT  FWQNPRNHFR  CQVQFYGLSE

NDEWTQDRAK  PVTQIVSAEA  WGRADCGFTS  VSYQQGVLSA

TILYEILLGK  ATLYAVLVSA  LVLMAMVKRK  DF
```

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Austin-Ward and Villaseca, Revista Medica de Chile, 126(7):838-845, 1998.
Ausubel et al., Current Protocols in Molecular Biology, Greene Publishing Associates and John
Baird et al., Scand. J. Immunol., 60(4):363-71, 2004.
Baraldo et al., Infect. Immun., 73(9):5835-41, 2005.
Bijker et al., J. Immunol., 179:5033-5040, 2007. Biology Publications, p. 433, 1997.
Blanchard and Shastri, Curr. Opin. Immunol., 20:82-88, 2008.
Bukowski et al., Clinical Cancer Res., 4(10):2337-2347, 1998.
Burrows et al., Trends Immunol., 27:11-16, 2006.
Camacho et al. (2004) J Clin Oncology 22(145): Abstract No. 2505, 2004.
Celluzzi et al., J. Exp. Med., 183 283-287, 1996.
Chothia et al., EMBO J. 7:3745, 1988.
Christodoulides et al., Microbiology, 144(Pt 11):3027-3037, 1998.
Cohen et al. J Immunol. 175:5799-5808, 2005. Cold Spring Harbor, N.Y. 2001.
Collins et al., Nature, 371:626-629, 1994.
Davidson et al., J. Immunother., 21(5):389-398, 1998.
Davila et al. PLoS ONE 8(4): e61338, 2013.
Drin et al., AAPS Pharm. Sci., 4(4):E26, 2002.
Du et al., J. Pept. Res., 51:235-243, 1998.
Dudley et al., J. Immunol., 26(4):332-342, 2003.
Elliott and O'Hare, Cell, 88:23-233, 1997.
European Patent Application No. EP2537416
Fedorov et al., Sci. Transl. Medicine, 5(215) 2013.
Janeway et al, Immunobiology: The Immune System in Health and Disease, 3$^{rd}$ Ed., Current Frankel and Pabo, Cell, 55:189-1193, 1988.
Goeddel, Methods Enzymol., 185:3-7, 1990.
Guo et al., Nature, 360:364-366, 1992.
Gupta et al., Biomaterials, 26:3995-4021, 2005.
Hanibuchi et al., Int. J. Cancer, 78(4):480-485, 1998.
Heemskerk et al. Hum Gene Ther. 19:496-510, 2008.
Hellstrand et al., Acta Oncologica, 37(4):347-353, 1998.
Hollander, Front. Immun., 3:3, 2012.
Hui and Hashimoto, Infection Immun., 66(11):5329-5336, 1998.
Hurwitz et al. (1998) Proc Natl Acad Sci USA 95(17): 10067-10071
International Patent Publication No. WO 00/37504
International Patent Publication No. WO 01/14424
International Patent Publication No. WO 98/42752
International Patent Publication No. WO 99/60120
International Patent Publication No. WO1995001994
International Patent Publication No. WO1998042752
International Patent Publication No. WO2000037504
International Patent Publication No. WO200014257

International Patent Publication No. WO2001014424
International Patent Publication No. WO2006/121168
International Patent Publication No. WO2007/103009
International Patent Publication No. WO2009/101611
International Patent Publication No. WO2010/027827
International Patent Publication No. WO2011/066342
International Patent Publication No. WO2012/129514
International Patent Publication No. WO2013/071154
International Patent Publication No. WO2013/123061
International Patent Publication No. WO2013/166321
International Patent Publication No. WO2013126726
International Patent Publication No. WO2014/055668
International Patent Publication No. WO2014031687
International Patent Publication No. WO2015016718
Janeway et al, Immunobiology: The Immune System in Health and Disease, 3' Ed., Current Biology Publications, p. 433, 1997.
Johnson et al. Blood 114:535-46, 2009.
Jores et al., PNAS U.S.A. 87:9138, 1990.
Kabat et al., "Sequences of Proteins of Immunological Interest, US Dept. Health and Human Services, Public Health Service National Institutes of Health, 5$^{th}$ ed, 1991.
Leal, M., Ann NY Acad Sci 1321, 41-54, 2014.
Lefranc et al., Dev. Comp. Immunol. 27:55, 2003.
Li, Nat Biotechnol. 23:349-354, 2005.
Lin et al., J. Biol. Chem., 270:4255-14258, 1995.
Melief and van der Burg, Nat. Rev. Cancer, 8:351-360, 2008.
Mellman et aL, Nature 480:480-489, 2011.
Mokyr et al. Cancer Res 58:5301-5304, 1998.
Moorthy et al., PLoS Med., 1(2):e33, 2004.
Neelapu et al., Blood, 15:109(12):5160-5163, 2007.
Pardoll, Nature Rev Cancer 12:252-264, 2012.
Parkhurst et al. Clin Cancer Res. 15: 169-180, 2009.
Popescu et al. Blood, 15:109(12):5407-5410, 2007.
Qin et al., Proc. Natl. Acad. Sci. USA, 95(24):14411-14416, 1998.
Quintarelli et aL, Blood, 117:3353-3362, 2011.
Rojas et al., J. Biol. Chem., 271:27456-27461, 1996.
Rojas et al., Proc. West. Pharmacol. Soc., 41:55-56, 1998.
Sadelain et al., Cancer Discov. 3(4): 388-398, 2013.
Sambrook et al., Molecular Cloning: A Laboratory Manual, 3$^{rd}$ ed., Cold Spring Harbor Press, 2001.
Samino et al., J. Biol. Chem., 281:6358-6365, 2006.
Schwarze et al., Trends in Cell Biol., 10:290-295, 2000.
Stryhn et al., Eur. J. Immunol., 30:3089-3099, 2000.
Terakura et al. Blood. 1:72-82, 2012.
Turtle et al., Curr. Opin. Immunol., 24(5): 633-39, 2012.
U.S. Pat. No. 4,373,071
U.S. Pat. No. 4,401,796
U.S. Pat. No. 4,458,066
U.S. Pat. No. 4,598,049
U.S. Pat. No. 4,870,287
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,844,905
U.S. Pat. No. 5,846,945
U.S. Pat. No. 5,885,796
U.S. Pat. No. 6,207,156
U.S. Pat. No. 6,225,042
U.S. Pat. No. 6,355,479
U.S. Pat. No. 6,362,001
U.S. Pat. No. 6,410,319
U.S. Pat. No. 6,451,995
U.S. Pat. No. 6,790,662
U.S. Pat. No. 7,070,995
U.S. Pat. No. 7,265,209
U.S. Pat. No. 7,354,762
U.S. Pat. No. 7,446,179
U.S. Pat. No. 7,446,190
U.S. Pat. No. 7,446,191
U.S. Pat. No. 7,666,604
U.S. Pat. No. 8,008,449
U.S. Pat. No. 8,017,114
U.S. Pat. No. 8,119,129
U.S. Pat. No. 8,252,592
U.S. Pat. No. 8,324,353
U.S. Pat. No. 8,329,867
U.S. Pat. No. 8,339,645
U.S. Pat. No. 8,354,509
U.S. Pat. No. 8,398,282
U.S. Pat. No. 8,479,118
U.S. Pat. No. 8,735,553
U.S. Patent Publication No. 2002/131960
U.S. Patent Publication No. 2005/0260186
U.S. Patent Publication No. 2006/0104968
U.S. Patent Publication No. 2009/0004142
U.S. Patent Publication No. 2009/0017000
U.S. Patent Publication No. 2011/0008369
U.S. Patent Publication No. 2013/0149337
U.S. Patent Publication No. 2013/287748
U.S. Patent Publication No. 2014/022021
U.S. Patent Publication No. 2014/0294898
Varela-Rohena et al. Nat Med. 14: 1390-1395, 2008.
Wang and Wang, Nat. Biotechnol., 20:149-154, 2002.
Wang et al. J Immunother. 35(9):689-701, 2012.
Wu et al., Cancer, 18(2): 160-75, 2012.
Yee et al. Immunological reviews 257: 250-263. 2014.
Yee et al., J. Immunol. Methods, 261(1-2):1-20, 2002.
Young et al., J. Exp. Med., 183:-11, 1996.
Zwaveling et al., J. Immunol., 169:350-358, 2002.

What is claimed is:

1. An engineered T cell receptor (TCR) comprising an alpha chain CDR3 of SEQ ID NO:2 and a beta chain CDR3 of SEQ ID NO:3 or an alpha chain CDR3 of SEQ ID NO: 19 and a beta chain CDR3 of SEQ ID NO:20.

2. The TCR of claim 1, wherein the engineered TCR binds HLA-A2.

3. The TCR of claim 1, wherein the engineered TCR binds HLA-A*0201.

4. The TCR of claim 1, wherein the TCR comprises an alpha chain having at least 90% identity to the amino acid sequence of SEQ ID NO: 5 or 16 and/or a beta chain having at least 90% identity to the amino acid sequence of SEQ ID NO:7 or 18.

5. The TCR of claim 1, wherein the TCR comprises an alpha chain having at least 95% identity to the amino acid sequence of SEQ ID NO: 5 or 16 and/or a beta chain having at least 95% identity to the amino acid sequence of SEQ ID NO:7 or 18.

6. The TCR of claim 1, wherein the TCR comprises an alpha chain having at least 99% identity to the amino acid sequence of SEQ ID NO: 5 or 16 and/or a beta chain having at least 99% identity to the amino acid sequence of SEQ ID NO:7 or 18.

7. The TCR of claim 1, wherein the TCR comprises an alpha chain of SEQ ID NO:5 or 16 and/or a beta chain of SEQ ID NO:7 or 18.

8. The TCR of claim 1, wherein the TCR is further defined as a soluble TCR, wherein the soluble TCR does not comprise a transmembrane domain.

9. The TCR of any one of claims 1-8, further comprising a detectable label.

10. The TCR of any one of claims 1-8, further comprising a therapeutic agent.

11. A multivalent TCR complex comprising a plurality of TCRs according to any one of claims 1-8.

12. The complex of claim 11, wherein the multivalent TCR comprises 2, 3, 4 or more TCRs associated with one another.

13. The complex of claim 12, wherein the multivalent TCR is present in a lipid bilayer or is attached to a particle.

14. The complex of claim 12, wherein the TCRs are associated with one another via a linker molecule.

15. A polypeptide encoding the TCR of any one of claims 1-8.

16. A polynucleotide encoding the polypeptide of claim 15.

17. An expression vector comprising the TCR of any one of claims 1-8.

18. The expression vector of claim 17, wherein the expression vector is a viral vector.

19. The expression vector of claim 18, wherein the viral vector is a retroviral vector.

20. The expression vector of claim 17, further comprising a linker domain.

21. The expression vector of claim 20, wherein the linker domain is between the alpha chain and beta chain.

22. The expression vector of claim 20, wherein the linker domain comprises one or more cleavage sites.

23. The expression vector of claim 22, wherein the one or more cleavage sites are a Furin cleavage site and/or a P2A cleavage site.

24. The expression vector of claim 22, wherein the one or more cleavage sites are separated by a spacer.

25. The expression vector of claim 24, wherein the spacer is SGSG or GSG.

26. A host cell engineered to express the TCR of any one of claims 1-8.

27. The host cell of claim 26, wherein the cell is an immune cell.

28. The host cell of claim 26, wherein the cell is an NK cell, invariant NK cell, NKT cell, mesenchymal stem cell (MSC), or induced pluripotent stem (iPS) cell.

29. The host cell of claim 26, wherein the cell is isolated from the umbilical cord.

30. The host cell of claim 27, wherein the immune cell is a T cell or peripheral blood lymphocyte.

31. The host cell of claim 30, wherein the T cell is a CD8+ T cell, CD4+ T cell, or γδ T cell.

32. The host cell of claim 30, wherein the T cell is a regulatory T cell (Treg).

33. The host cell of claim 26, wherein the cell is allogeneic or autologous.

34. A composition comprising the TCR-engineered host cell of claim 26 for the treatment of cancer in a subject.

* * * * *